(12) United States Patent
Kehat et al.

(10) Patent No.: US 11,060,092 B2
(45) Date of Patent: Jul. 13, 2021

(54) INHIBITORS OF CYTOPLASMIC HISTONE DEACETYLASE 4 COMPLEX FOR TREATING OR PREVENTING VASCULAR OR VALVE CALCIFICATION

(71) Applicants: TECHNION RESEARCH AND DEVELOPMENT FOUNDATION LTD., Haifa (IL); RAMBAM MED-TECH LTD., Haifa (IL)

(72) Inventors: Izhak Kehat, Haifa (IL); Alon Abend, Ramat Gan (IL); Omer Shkedi, Haifa (IL); Lilac Caspi, Aloney Abba (IL)

(73) Assignees: TECHNION RESEARCH & DEVELOPMENT FOUNDATION LIMITED, Haifa (IL); RAMBAM MED-TECH LTD., Haifa (IL)

( * ) Notice: Subject to any disclaimer, the term of this patent is extended or adjusted under 35 U.S.C. 154(b) by 0 days.

(21) Appl. No.: 16/316,677

(22) PCT Filed: Jul. 13, 2017

(86) PCT No.: PCT/IL2017/050797
§ 371 (c)(1),
(2) Date: Jan. 10, 2019

(87) PCT Pub. No.: WO2018/011811
PCT Pub. Date: Jan. 18, 2018

(65) Prior Publication Data
US 2019/0309300 A1 Oct. 10, 2019

Related U.S. Application Data

(60) Provisional application No. 62/361,516, filed on Jul. 13, 2016, provisional application No. 62/507,841, filed on May 18, 2017.

(51) Int. Cl.
| | | |
|---|---|---|
| *A61K 48/00* | (2006.01) |
| *C07H 21/04* | (2006.01) |
| *C12N 15/113* | (2010.01) |
| *A61P 9/10* | (2006.01) |
| *A61K 31/506* | (2006.01) |
| *A61K 31/5377* | (2006.01) |
| *A61K 31/713* | (2006.01) |
| *A61K 45/06* | (2006.01) |
| *A61K 38/15* | (2006.01) |
| *A61K 38/12* | (2006.01) |

(52) U.S. Cl.
CPC ........ *C12N 15/1137* (2013.01); *A61K 31/506* (2013.01); *A61K 31/5377* (2013.01); *A61K 31/713* (2013.01); *A61K 38/12* (2013.01); *A61K 38/15* (2013.01); *A61K 45/06* (2013.01); *A61P 9/10* (2018.01); *C12N 15/113* (2013.01); *C12N 2310/14* (2013.01)

(58) Field of Classification Search
CPC .......................... A61K 31/713; C12N 15/113
See application file for complete search history.

(56) References Cited

U.S. PATENT DOCUMENTS

| | | | |
|---|---|---|---|
| 5,877,022 A | 3/1999 | Stinchcomb et al. |
| 6,013,487 A | 1/2000 | Mitchell et al. |
| 6,083,702 A | 7/2000 | Mitchell et al. |
| 2008/0132575 A1 | 6/2008 | Wong et al. |
| 2015/0290168 A1* | 10/2015 | Montminy ........... A61K 31/137 424/133.1 |

OTHER PUBLICATIONS

Chen (Cardiovasc Diabetol, 2015, 14:99, pp. 1-13).*
Leopold (Circ Cardiovasc Interv, 2012, 5(4), 605-614).*
Search Report dated Jan. 11, 2018 for corresponding PCT Application No. PCT/IL2017/050797.
Search Report dated Jan. 29, 2020 for corresponding EP Application No. EP17827131.8.
Al-Hakim et al. "14-3-3 cooperates with LKB1 to regulate the activity and localization of QSK and SIK" J Cell Sci. Dec. 1, 2005;118(Pt 23):5661-73.
Allison et al. "Patterns and risk factors for systemic calcified atherosclerosis" Arterioscler Thromb Vasc Biol. 2004;24(2):331-336.
Arnold et al. "MEF2C transcription factor controls chondrocyte hypertrophy and bone development" Developmental cell. 2007;12(3):377-89.
Azechi et al. "Trichostatin A, an HDAC Class I/II inhibitor, promotes Pi-induced vascular calcification via up-regulation of the expression of alkaline phosphatase" J Atheroscler Thromb. 2013;20(6):538-47. Epub Mar. 22, 2013.
Backs et al. "CaM kinase II selectively signals to histone deacetylase 4 during cardiomyocyte hypertrophy" J Clin Invest. 2006;116(7):1853-1864.
Baker et al. "Use of the mouse aortic ring assay to study angiogenesis.—PubMed—NCBI" Nature protocols. 2012;7(1):89-104.

(Continued)

*Primary Examiner* — Amy H Bowman
(74) *Attorney, Agent, or Firm* — Pearl Cohen Zedek Latzer Baratz LLP

(57) ABSTRACT

A pharmaceutical composition and a method of treating, reducing or preventing vascular, cardiovascular arterial or valve calcification in a subject in need comprising administering to the subject an effective amount of an agent that prevents or reduces the expression of HDAC4, an agent that modulates the location of HDAC4, an agent that binds to HDAC4 or an inhibitor of HDAC4 or any combination thereof is provided. In some embodiments, there is provided a pharmaceutical composition comprising: an agent that prevents or reduces the expression of HDAC4, an agent that modulates the location of HDAC4, an agent that binds to HDAC4 or an inhibitor of HDAC4 or any combination thereof; an agent that prevents or reduces the expression of SIK or is an inhibitor of SIK; and/or an agent that prevents or reduces the expression of ENIGMA (Pdlim7) or is an inhibitor of ENIGMA.

5 Claims, 32 Drawing Sheets

Specification includes a Sequence Listing.

(56) References Cited

OTHER PUBLICATIONS

Berdeaux et al. "SIK1 is a class II HDAC kinase that promotes survival of skeletal myocytes" Nature medicine. 2007;13(5):597-603.
Broder et al. "The ras recruitment system, a novel approach to the study of protein-protein interactions" Curr Biol. Oct. 8, 1998;8(20):1121-4.
Carpenter et al. "CellProfiler—image analysis software for identifying and quantifying cell phenotypes" Genome biology. 2006;7(10):R100.
Chakraborty et al. "Alpha-actinin 4 potentiates myocyte enhancer factor-2 transcription activity by antagonizing histone deacetylase 7" J Biol Chem. Nov. 17, 2006;281(46):35070-80. Epub Sep. 15, 2006.
Chen & Cepko "HDAC4 regulates neuronal survival in normal and diseased retinas" Science. 2009;323(5911):256-259.
Chen et al. "Histone deacetylase (HDAC) inhibition improves myocardial function and prevents cardiac remodeling in diabetic mice" Cardiovasc Diabetol; 2015; 14:99.
Choudhary et al. "Lysine acetylation targets protein complexes and co-regulates major cellular functions" Science. 2009;325(5942):834-840.
Clark et al. "Phosphorylation of CRTC3 by the salt-inducible kinases controls the interconversion of classically activated and regulatory macrophages" Proceedings of the National Academy of Sciences. 2012;109(42)16986-16991.
Clocchiatti et al. "Beside the MEF2 axis—unconventional functions of HDAC4" Cellular signaling. 2013;25(1):269-76.
Cohen et al. "The histone deacetylase HDAC4 connects neural activity to muscle transcriptional reprogramming" The Journal of biological chemistry. 2007;282(46):33752-9.
Di Giorgio et al. "Selective class IIa HDAC inhibitors—myth or reality" Cellular and molecular life sciences—CMLS. 2015;72(1):73-86.
Eom & Cook "Posttranslational modifications of histone deacetylases: implications for cardiovascular diseases" Pharmacol Ther. Aug. 2014;143(2):168-80.
Fitzsimons The Class IIa histone deacetylase HDAC4 and neuronal function—Nuclear nuisance and cytoplasmic stalwart? Neurobiology of learning and memory. 2015;123-149-58.
Gary et al. "Lim mineralization protein-1 knockout mice have reduced spine trabecular bone density on microcomputed tomography due to decreased bone morphogenetic protein responsiveness" Neurosurgery 2014, 61 Suppl 1, 182-186.
Giachelli et al. "Regulation of vascular calcification: roles of phosphate and osteopontin" Circ Res 2005, 96, 717-722.
Goldbarg et al. "Insights into degenerative aortic valve disease" Journal of the American College of Cardiology. 2007;50(13):1205-13.
Gorman et al. "Stable alteration of pre-mRNA splicing patterns by modified U7 small nuclear RNAs" Proc Natl Acad Sci U S A. Apr. 28, 1998;95(9):4929-34.
Haberland et al. "The many roles of histone deacetylases in development and physiology—implications for disease and therapy" Nat Rev Genet. 2009;10(1):32-42.
Idelevich et al. "Bone Gla protein increases HIF-1alpha-dependent glucose metabolism and induces cartilage and vascular calcification" Arterioscler Thromb Vasc Biol. Sep. 2011;31(9):e55-71.
Jung et al. "Enigma negatively regulates p53 through MDM2 and promotes tumor cell survival in mice" J Clin Invest. 2010;120(12):4493-4506.
Kawaguchi et al. "The deacetylase HDAC6 regulates aggresome formation and cell viability in response to misfolded protein stress" Cell. Dec. 12, 2003;115(6):727-38.
Kehat et al. "Modulation of chromatin position and gene expression by HDAC4 interaction with nucleoporins" J Cell Biol 2011, 193, 21-29.
Kinsey et al. "Class II histone deacetylases confer signal responsiveness to the ankyrin-repeat proteins ANKRA2 and RFXANK" Mol Biol Cell 2006, 17, 438-447.
Krcmery et al. "Nucleocytoplasmic functions of the PDZ-LIM protein family—new insights into organ development" Bioessays. 2011;32(2):100-108.
Krcmery et al. "Loss of the cytoskeletal protein Pdlim7 predisposes mice to heart defects and hemostatic dysfunction" PLoS One. 2013;8(11):e80809.
Lahm et al. "Unraveling the hidden catalytic activity of vertebrate class IIa histone deacetylases" Proc Natl Acad Sci U S A. 2007;104(44):17335-17340.
Leopold "Vascular calcification—Mechanisms of vascular smooth muscle cell calcification" Trends in Cardiovascular Medicine. 2015;25(4):267-274.
Liu et al. "Osteoinductive LIM mineralization protein-1 suppresses activation of NF-kappaB and selectively regulates MAPK pathways in pre-osteoclasts" Bone 2010, 46, 1328-1335.
Ludivine et al. "HDACs regulate miR-133a expression in pressure overload-induced cardiac fibrosis" Circ Heart Fail. Nov. 2015;8(6):1094-104.
Mackenzie et al. "MOVAS-1 cell line: a new in vitro model of vascular calcification" Int J Mol Med 2011, 27, 663-668.
Makinistoglu & Karsenty "The class II histone deacetylase HDAC4 regulates cognitive, metabolic and endocrine functions through its expression in osteoblasts" Molecular metabolism. 2015;4(1):64-9.
McKinsey et al. "Class II histone deacetylases confer signal responsiveness to the ankyrin-repeat proteins ANKRA2 and RFXANK" Mol Biol Cell. 2006;17(1):438-447.
Mielcarek et al. "SAHA decreases HDAC 2 and 4 levels in vivo and improves molecular phenotypes in the R6/2 mouse model of Huntington's disease" PLoS One. 2011;6(11):e27746.
Monovich et al. "A novel kinase inhibitor establishes a predominant role for protein kinase D as a cardiac class IIa histone deacetylase kinase" FEBS letters. 2010;584(3):631-7.
Obri et al. "HDAC4 integrates PTH and sympathetic signaling in osteoblasts" The Journal of cell biology. 2014;205(6):771-80.
Paloian & Giachelli "A current understanding of vascular calcification in CKD" Am J Physiol Renal Physiol. 2014;307(8):F891-900.
Panizo et al. "MicroRNAs 29b, 133b, and 211 regulate vascular smooth muscle calcification mediated by high phosphorus" J Am Soc Nephrol. Mar. 2016;27(3):824-34.
Parra & Verdin "Regulatory signal transduction pathways for class IIa histone deacetylases" Current opinion in pharmacology. 2010;10(4):454-60.
Parra "Class IIa HDACs—new insights into their functions in physiology and pathology" The FEBS Journal. 2015;282(9):1736-44.
Patel et al. "The LKB1-salt-inducible kinase pathway functions as a key gluconeogenic suppressor in the liver" Nat Commun. Aug. 4, 2014;5:4535.
Pellicena & Schulman "CaMKII inhibitors—from research tools to therapeutic agents" Frontiers in pharmacology. 2014;5-21.
Puttaraju et al. "Spliceosome-mediated RNA trans-splicing as a tool for gene therapy" Nat Biotechnol. Mar. 1999;17(3):246-52.
Qiao et al. "Cartilaginous metaplasia in calcified diabetic peripheral vascular disease-morphologic evidence of enchondral ossification" Human pathology. 2003;34(4):402-7.
Rennenberg et al. "Vascular calcifications as a marker of increased cardiovascular risk—a meta-analysis" Vasc Health Risk Manag. 2009;5(1):185-197.
Sage et al. "Regulatory mechanisms in vascular calcification" Nat Rev Cardiol. 2010;7(9):528-536.
Sangadala et al. "Characterization of a unique motif in LIM mineralization protein-1 that interacts with jun activation-domain-binding protein 1" Molecular and cellular biochemistry. 2014;385(1-2):1 45-57.
Sasagawa et al. "SIK3 is essential for chondrocyte hypertrophy during skeletal development in mice" Development (Cambridge, England). 2012;139(6):1153-63.

(56) References Cited

OTHER PUBLICATIONS

Shao et al. "Inflammation and the osteogenic regulation of vascular calcification—a review and perspective" Hypertension. 2010;55(3):579-92.

Sharlow et al. "Discovery of diverse small molecule chemotypes with cell-based PKD1 inhibitory activity" PLoS One 2011, 6, e25134.

Sharp & Zamore "Molecular biology. RNA interference." Science. Mar. 31, 2000;287(5462):2431-3.

Speer et al. "Smooth muscle cells give rise to osteochondrogenic precursors and chondrocytes in calcifying arteries" Circ Res. 2009;104(6):733-741.

Stephens et al. "Internal control genes for quantitative RT-PCR expression analysis in mouse osteoblasts, osteoclasts and macrophages" BMC Res Notes. Oct. 14, 2011;4:410.

Sun & Beier "Chondrocyte hypertrophy in skeletal development, growth, and disease" Birth defects research. Part C, Embryo today—reviews. 2014;102(1):74-82.

Vega et al. "Protein kinases C and D mediate agonist-dependent cardiac hypertrophy through nuclear export of histone deacetylase 5" Molecular and cellular biology. 2004;24(19):8374-85.

et al. "Histone deacetylase 4 controls chondrocyte hypertrophy during skeletogenesis" Cell. 2004;119(4):555-566.

Walkinshaw et al. "The Tumor Suppressor Kinase LKB1 Activates the Downstream Kinases SIK2 and SIK3 to Stimulate Nuclear Export of Class IIa Histone Deacetylases" Journal of Biological Chemistry. 2013;288(13):9345-9362.

Xie et al. "Histone deacetylase inhibition blunts ischemia/reperfusion injury by inducing cardiomyocyte autophagy" Circulation. Mar. 11, 2014;129(10)1139-51.

Bing R, Cavalcante JL, Everett RJ, Clavel MA, Newby DE, Dweck MR. Imaging and Impact of Myocardial Fibrosis in Aortic Stenosis. *JACC Cardiovasc Imaging*.2019;12(2):283-296.

De Ruijter AJ, van Gennip AH, Caron HN, Kemp S, van Kuilenburg AB. Histone deacetylases (HDACs): characterization of the classical HDAC family. *Biochem J*. 2003;370(Pt 3):737-749.

European Search Report of Application No. EP17827131.8 dated Jan. 29, 2020.

Maliken BD, Molkentin JD. Undeniable evidence that the adult mammalian heart lacks an endogenous regenerative stem cell. *Circulation*. 2018;138(8):806-808.

Oransky and Marcus; Harvard and the Brigham call for more than 30 retractions of cardiac stem cell research; Oct. 14, 2018; https://www.statnews.com/2018/10/14/harvard-brigham-retractions-stem-cell.

Sakamoto KM, Kim KB, Kumagai A, Mercurio F, Crews CM, Deshaies RJ. Protacs: chimeric molecules that target proteins to the Skp1-Cullin-F box complex for ubiquitination and degradation. Proc Natl Acad Sci U S A. 2001;98(15):8554-8559.

Steliou K, Boosalis MS, Perrine SP, Sangerman J, Faller DV. Butyrate histone deacetylase inhibitors. Biores Open Access. 2012;1(4):192-198.

Walsh ME, Bhattacharya A, Liu Y, Van Remmen H. Butyrate prevents muscle atrophy after sciatic nerve crush. Muscle Nerve. 2015;52(5):859-868.

Zhang L, Chen B, Zhao Y, et al. Inhibition of histone deacetylase-induced myocardial repair is mediated by c-kit in infarcted hearts. J Biol Chem. 2012;287(47):39338-39348.

Zhang LX, DeNicola M, Qin X, et al. Specific inhibition of HDAC4 in cardiac progenitor cells enhances myocardial repairs. Am J Physiol Cell Physiol. 2014;307(4):C358-C372.

\* cited by examiner

INHIBITORS OF CYTOPLASMIC HISTONE DEACETYLASE 4 COMPLEX FOR TREATING OR PREVENTING VASCULAR OR VALVE CALCIFICATION

CROSS-REFERENCE TO RELATED APPLICATIONS

This application is a National Phase Application of PCT International Application No. PCT/IL2017/050797, International Filing Date Jul. 13, 2017, claiming priority to U.S. Patent Application No. 62/361,516, filed Jul. 13, 2016, and to U.S. Patent Application No. 62/507,841, filed May 18, 2017, which are hereby incorporated by reference in their entirety.

BACKGROUND OF THE INVENTION

Vascular and valve calcification is a pathologic deposition of hydroxyapatite in the extracellular matrix of arterial walls or valve leaflets. These calcifications can occur in both the intima and the media layers of the arteries, are characteristic of aging, and are often related to different arterial diseases. Atherosclerosis is associated with intimal or neointimal calcification and an inflammatory milieu, while diabetic vasculopathy and metabolic factors, such as, hyperphosphatemia are often associated with medial calcification, and are usually not accompanied by inflammation. Similar calcification can also occur in aortic valve leaflets. The calcifications reduce the compliance and impair hemodynamics, and a meta-analysis showed that the presence of calcifications in any arterial wall is associated with a 3-4-fold higher risk of mortality and cardiovascular events. Currently, there is no specific treatment for vascular or valve calcification.

Vascular calcification is an active process driven by cells in the artery wall or valve. A lineage tracing study identified vascular smooth muscle cells (VSMCs) as the predominant drivers in medial arterial calcification. These cells upregulate the expression of several osteochondrogenic markers including Runx2, Sox9, Osterix, Osteopontin, Osteocalcin, and Alkaline phosphatase, and differentiate or 'transdifferentiate' to osteoblast-chondroblast like cells. Functionally these osteoblast-chondroblast like cells generate nucleating structures in the matrix for calcium hydroxyapatite deposition. Vascular calcification bear resemblance to bone formation, but there are some notable differences. For example, calcium phosphate in the arteries is not predominantly deposited on type I collagen as in bone, but rather on the amorphous elastin that comprises the elastic lamellae. Interestingly, vascular calcification is more pronounced in patients with bone loss, but it is not clear to what degree these two processes truly oppose or just coincide with each other. The molecular signals leading to the initiation and maintenance of vascular calcification have not been completely elucidated.

Histone deacetylases (HDACs) are eighteen proteins, grouped into four classes based on their structure and primary homology to *S. cerevisiae* HDACs. Among them, HDAC4, 5, 7, and 9 are classified as class IIa HDACs as they all have a long N-terminal domain in addition to their C-terminal deacetylase domain. This N-terminal domain was shown to contain interacting binding sites to a diverse group of proteins such as the myocyte enhancer factor 2 (MEF2) transcription factors, calmodulin binding transcription activator, chaperone protein 14-3-3, and alpha actinin. The N-terminal domain also contains three conserved Serine residues that can undergo phosphorylation by several kinases including calcium/calmodulin-dependent kinase II (CamK II), Protein Kinase D (PKD), and salt inducible kinase 1,2 and 3 (SIK1, SIK2, and SIK3). The phosphorylation of class IIa HDACs at these serine residues is a crucial event that determines their nuclear export and cytoplasmic retention through binding to cytoplasmic 14-3-3 proteins. The currently accepted paradigm for class IIa HDACs regulation explains function in the nucleus through binding to transcription factors, and a phosphorylation dependent nuclear export with cytoplasmic retention as a signal induced inhibitory mechanism. Despite having a large catalytic domain, class IIa HDACs exhibit minimal deacetylase activity. It has been proposed that class IIa HDACs may not be real enzymes, and that they act as adaptors of protein complexes or 'readers'.

Class IIa HDACs appear to be expressed in a tissue-specific manner, and have been shown to exert their activity in skeletal, cardiac and smooth muscle, brain, cartilage, and bone. Among the class IIa HDACs, HDAC4 was shown to have important function in bone and cartilage development. Global deletion of HDAC4 in mice results in precocious and ectopic hypertrophy of chondrocytes. Deletion of HDAC4 in osteoblasts, achieved by crossing Hdac4fl/fl mice with Runx2-Cre transgenic mice, resulted in low bone mass, suggesting that HDAC4 may be a positive regulator of bone formation.

SUMMARY OF THE INVENTION

This invention shows that the class IIa HDAC4 is upregulated during vascular and valve calcification and is a positive regulator, promoting the process of calcification. While the current paradigm suggests that class IIa HDACs are shuttled to the cytoplasm to inhibit their nuclear function, the invention further shows that cytoplasmic HDAC4 promotes vascular calcification through binding to the cytoplasmic protein ENIGMA (Pdlim7). The cytoplasmic retention of HDAC4 in VSMCs is mediated by SIK kinase (hereinafter "SIK"), and inhibition of SIK promotes nuclear accumulation of HDAC4, and blunts the calcification process.

According to an embodiment of the invention, there is provided a method of treating, reducing or preventing vascular, cardiovascular arterial or valve calcification in a subject in need comprising administering to the subject an effective amount of an agent that prevents or reduces the expression of HDAC4, an agent that modulates the location of HDAC4, an agent that binds to HDAC4 or an inhibitor of HDAC4; or any combination thereof.

In some embodiments, the vascular, cardiovascular arterial or valve calcification is associated with diabetes, aging, hyperphosphatemia, renal disease, and atherosclerosis.

In some embodiments, the inhibitor of HDAC4 is selected from the group consisting of hydroxamic acid based HDAC inhibitors, Suberoylanilide hydroxamic acid (SAHA), NVP-LAQS24, LBH589, Trichostatin A, Scriptaid, m-Carboxycinnamic acid bishydroxamic acid (CBHA), ABHA, Pyroxamide, Propenamides, Oxamflatin, 6-(3-Chlorophenylureido)caproic bydroxarn ic acid (3-CI-UCHA), A-161906, jnj16241199, tubacin, small interfering RNA (siRNA), short chain fatty acid HDAC inhibitors, butyrate, phenylbutyrate, vaiproate, hydroxamic acid, trichostatins, epoxyketone-containing cyclic tetrapeptides, HC-toxin, Chiamydocin, Diheteropeptide, WF-3161, Cyl-1, Cyl-2, non-epoxyketone-containing cyclic tetrapeptides, Apicidin, cyclic-hydroxamic-acid-containing peptides (CHAPS), benzamides, CI-994, trapoxin, deprudecin, organosulfur compounds, MS275, depsipeptide (FK228), trifluoromethyloxadiazole (TFMO) moiety containing molecules such as TMP 269, TMP 195 and any combination thereof.

In some embodiments of the invention, the agent that modulates the location of HDAC4 is an agent that prevents or reduces the expression of SIK or is an inhibitor of SIK, such as HG-9-91-01, WH-4-023, MRT67307, or YKL-05-099

In some embodiments of the invention, the agent that binds to HDAC4 is an agent that prevents or reduces the expression of ENIGMA (Pdlim7) or is an inhibitor of ENIGMA.

In some embodiments of the invention, the SIK is one or more of SIK isoforms SIK1, SIK2 or SIK 3.

In some embodiments of the invention, the agent that reduces SIK expression is an siRNA.

In some embodiments of the invention, the agent that reduces SIK expression is an agent that blocks upstream activator of SIK or an agent that induces a degradation of SIK or controls posttranslational modification of SIK.

In some embodiments of the invention, the agent that blocks upstream activator of SIK is LKB1 inhibitor.

In some embodiments of the invention, the agent that prevents or reduces the expression of ENIGMA (Pdlim7) is an siRNA of ENIGMA or an agent that induces a degradation of ENIGMA or controls posttranslational modification of ENIGMA.

In some embodiments of the invention, the agent that modulates the location of HDAC4 acts by shuttling the HDAC4 from the cytoplasm.

In some embodiments of the invention, there is provided a method of treating, reducing or preventing vascular, cardiovascular arterial or valve calcification in a subject in need comprising administering to the subject an effective amount of:

an agent that prevents or reduces the expression of HDAC4, an agent that modulates the location of HDAC4, an agent that binds to HDAC4 or an inhibitor of HDAC4 or any combination thereof;

an agent that prevents or reduces the expression of SIK or is an inhibitor of SIK; and/or an agent that prevents or reduces the expression of ENIGMA (Pdlim7) or is an inhibitor of ENIGMA.

In some embodiments of the invention, the agent that prevents or reduces the expression of HDAC4, the agent that modulates the location of HDAC4, the agent that binds to HDAC4 or the inhibitor of HDAC4 or any combination thereof; the agent that prevents or reduces the expression of SIK or is the inhibitor of SIK; and/or the agent that prevents or reduces the expression of ENIGMA (Pdlim7) or is the inhibitor of ENIGMA; are administered consecutively or simultaneously.

In some embodiments of the invention, there is provided a pharmaceutical composition comprising:

an agent that prevents or reduces the expression of HDAC4, an agent that modulates the location of HDAC4, an agent that binds to HDAC4 or an inhibitor of HDAC4 or any combination thereof;

an agent that prevents or reduces the expression of SIK or is an inhibitor of SIK; and/or an agent that prevents or reduces the expression of ENIGMA (Pdlim7) or is an inhibitor of ENIGMA.

In some embodiments of the invention, the pharmaceutical composition comprising an agent that prevents or reduces the expression of HDAC4, an agent that modulates the location of HDAC4, an agent that binds to HDAC4 or an inhibitor of HDAC4 or any combination thereof; an agent that prevents or reduces the expression of SIK or is an inhibitor of SIK; and/or an agent that prevents or reduces the expression of ENIGMA (Pdlim7) or is an inhibitor of ENIGMA; is used for treating, reducing or preventing vascular, cardiovascular arterial or valve calcification in a subject in need.

In some embodiments of the invention, there is provided a pharmaceutical composition comprising an effective amount of an agent that prevents or reduces the expression of HDAC4, an agent that modulates the location of HDAC4, an agent that binds to HDAC4 or an inhibitor of HDAC4, or any combination thereof wherein the pharmaceutical composition is used for treating, reducing or preventing vascular, cardiovascular arterial or valve calcification in a subject in need.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A: qRT-PCR gene expression analysis of osteochondrogenic markers in VSMCs following 7-day treatment with high phosphate media (HPM) (grey) or control media (white). Data are shown as means±SEM (n=6), normalized to control. Two tailed unpaired Student's t-test, *$P<0.05$.

FIG. 1B: O-cresolphthalein calcium colorimetric assay, normalized to protein concentration, of VSMCs after two weeks in HPM (grey) or control media (white). Data are shown as means±SEM (n=9). Two tailed unpaired Student's t-test, *$P<0.05$.

FIG. 1C: qRT-PCR gene expression analysis of HDACs in VSMCs following 7-day treatment with high phosphate media (HPM) (grey) or control media (white). Data are shown as means±SEM (n=6), normalized to control. Two tailed unpaired Student's t-test, *$P<0.05$.

FIG. 1D: Western blot analysis and quantification of HDAC4 protein levels in VSMCs after 4 or 6 days of HPM treatment. HDAC4 levels were normalized to GAPDH levels in arbitrary density units (AU). Data are shown as means±SEM (n=3). Two tailed unpaired Student's t-test, *$P<0.05$.

FIG. 1E: qRT-PCR gene expression analysis of osteochondrogenic markers and HDAC4 in the mouse aortic rings assay treated for 14 days with (grey) or without (white) HPM. Data are shown as means±SEM (n=4), relative to zero. Two tailed unpaired Student's t-test, *$P<0.05$.

FIG. 1F: Representative images of histological sections of aortic rings grown for 14 days in control medium or HPM, stained black for calcium using Von Kossa stain. Scale bar=10 μm.

FIG. 1G: qRT-PCR gene expression analysis of osteochondrogenic markers and HDAC4 in calcified human aortic valves compared to controls. Data are shown as means±SEM (n=3), normalized to control. Two tailed unpaired Student's t-test, *$P<0.05$.

FIG. 1H: Gene expression qRT-PCR analysis of HDAC5 and HDAC9 in VSMCs following treatment with high phosphate media (HPM) (grey) or control media (white).

Data are shown as means±SEM (n=6), normalized to control, with two tailed unpaired Student's t-test. *P<0.05.

Figure 1A:
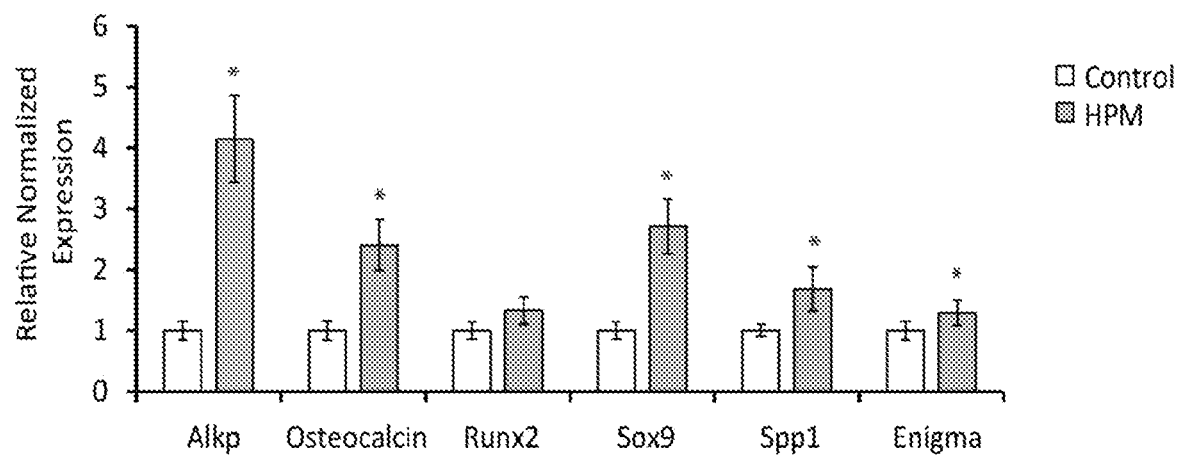
FIGS. 1A-1G: Histone deacetylase 4 (HDAC4) is upregulated during vascular and valve calcification.
Figure 1B:
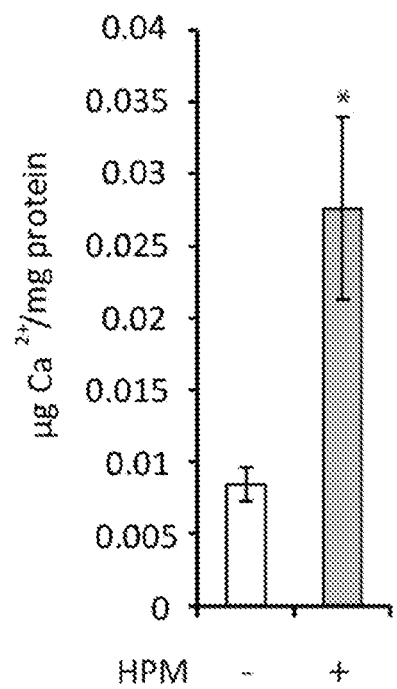
Figure 1C:
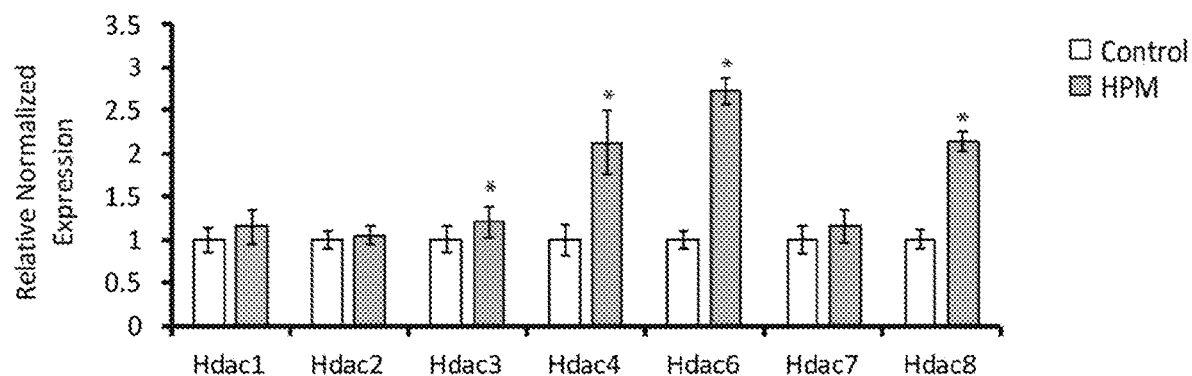
Figure 1D:
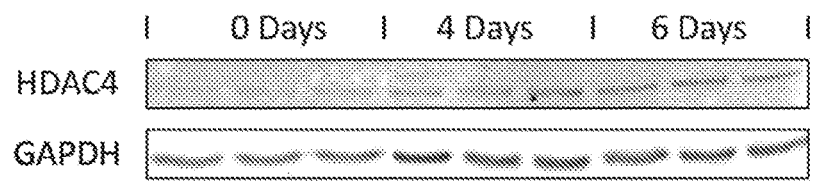
Figure 1D:
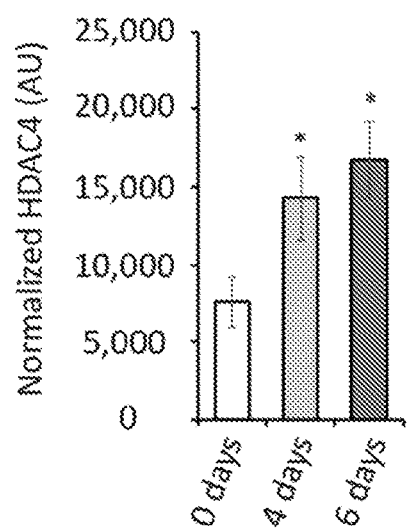
Figure 1E:
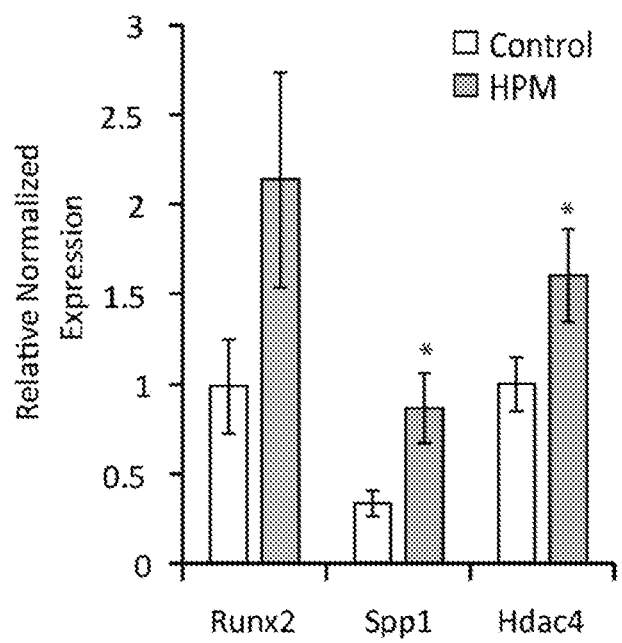
Figure 1F:
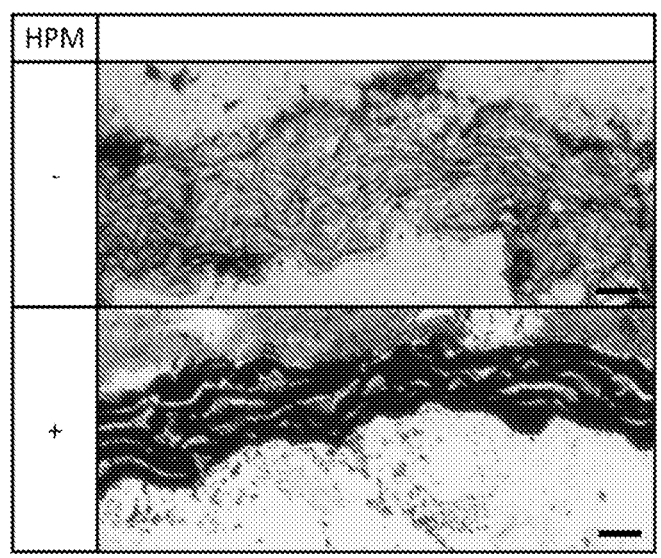
Figure 1G:
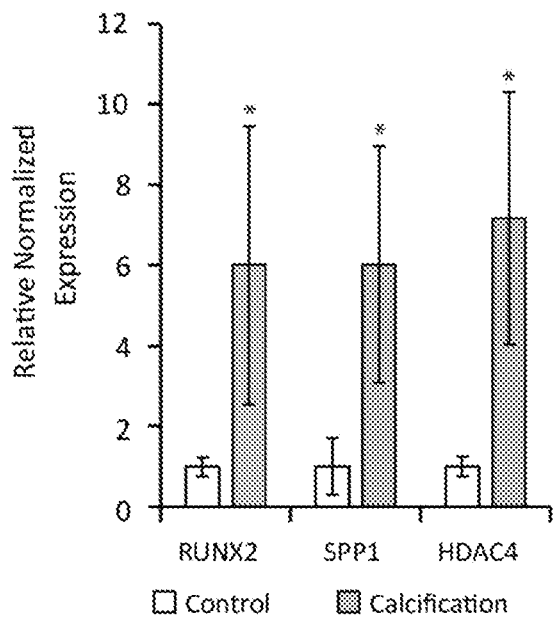
Figure 1H:
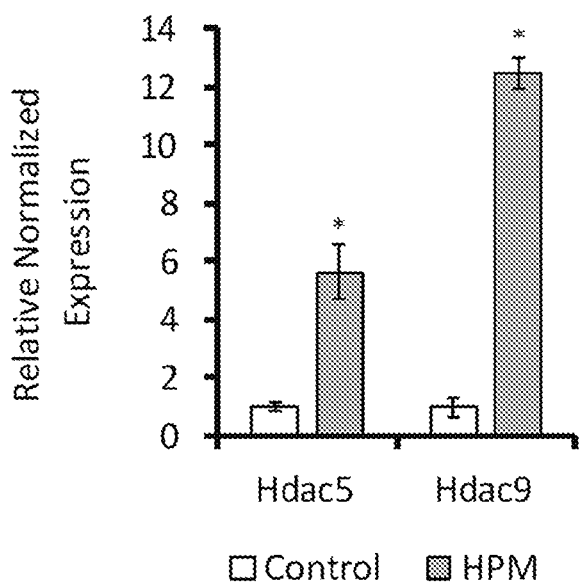
FIGS. 1H-1I: HDACs expression levels in VSMCs
Figure 1I:
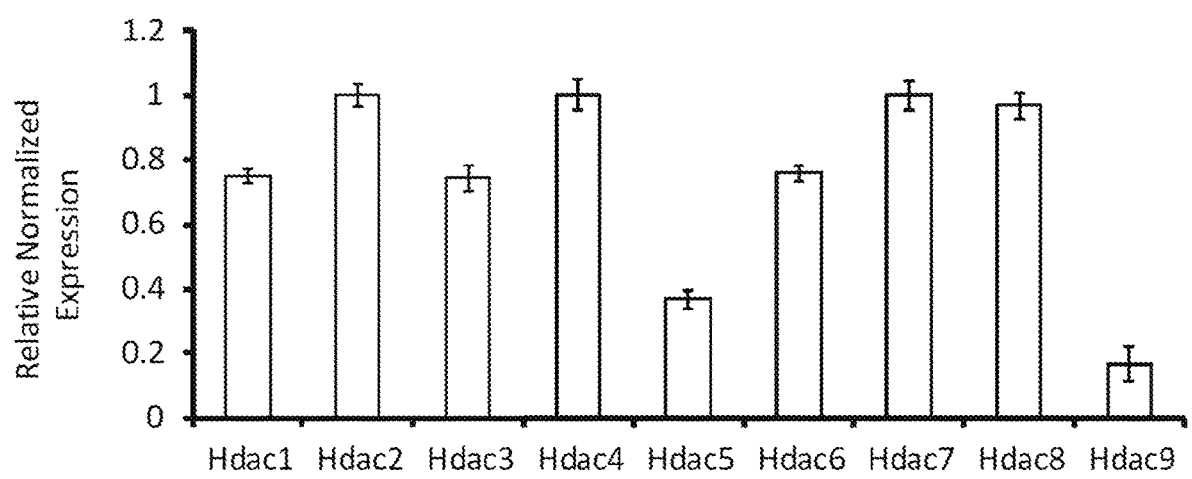

FIG. 1I: Expression levels of HDACs 1-9 in VSMCs grown in control media analyzed using qRT-PCR.). Data are shown as means±SEM (n=6), relative to zero.

FIGS. 2A-2F: Effects of overexpression and knockdown of HDAC4 on calcification.

Figure 2A:
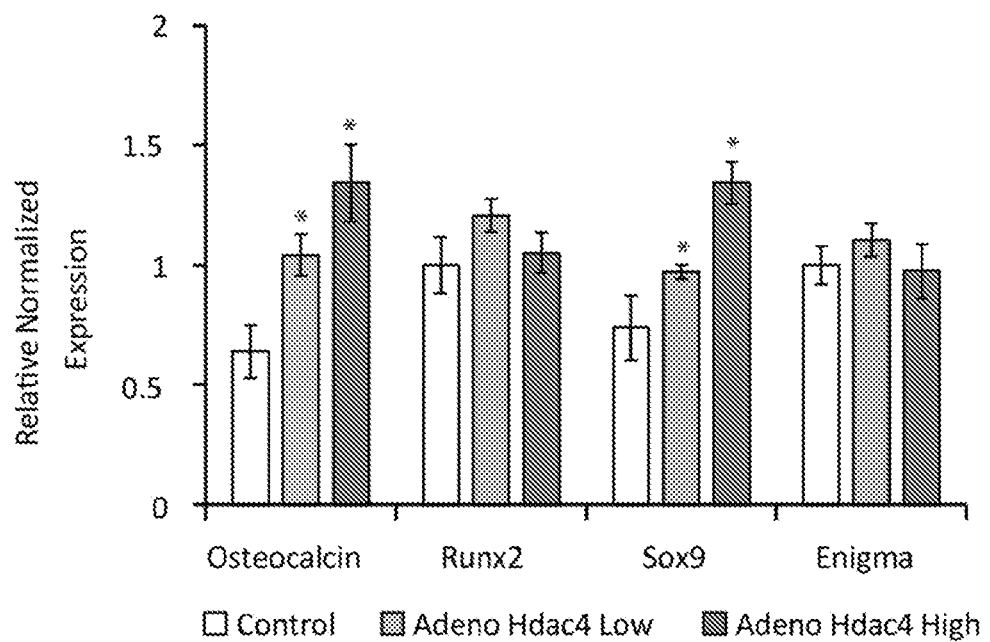

FIG. 2A: VSMCs were transduced with two different concentrations of adenoviral vector encoding for flag tagged HDAC4 or control beta-gal virus. Gene expression qRT-PCR analysis of calcification markers was performed. Data are shown as means±SEM (n=6), relative to zero. Two tailed unpaired Student's t-test, *P<0.05 vs. control.

Figure 2B:
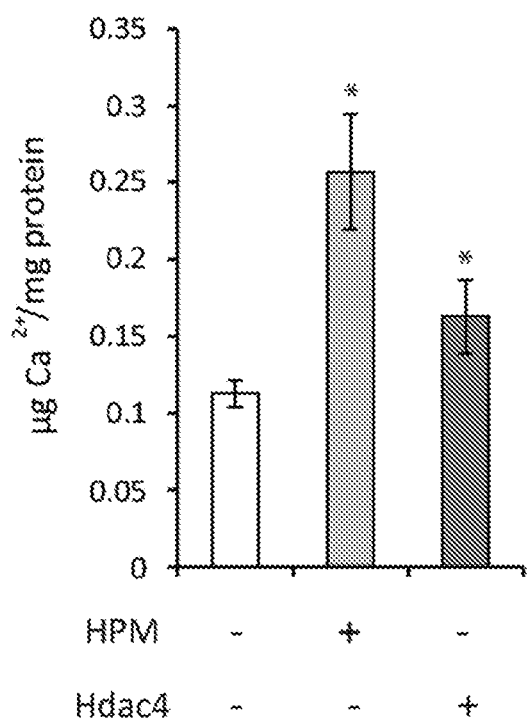

FIG. 2B: O-cresolphthalein calcium colorimetric assay of VSMCs after two weeks of control media (white) or HPM (light grey), or VSMCs transfected with HDAC4 in control media (dark grey). Data are shown as means±SEM (n=6), normalized to protein concentration. Two tailed unpaired Student's t-test, *P<0.05 vs. control.

Figure 2C:
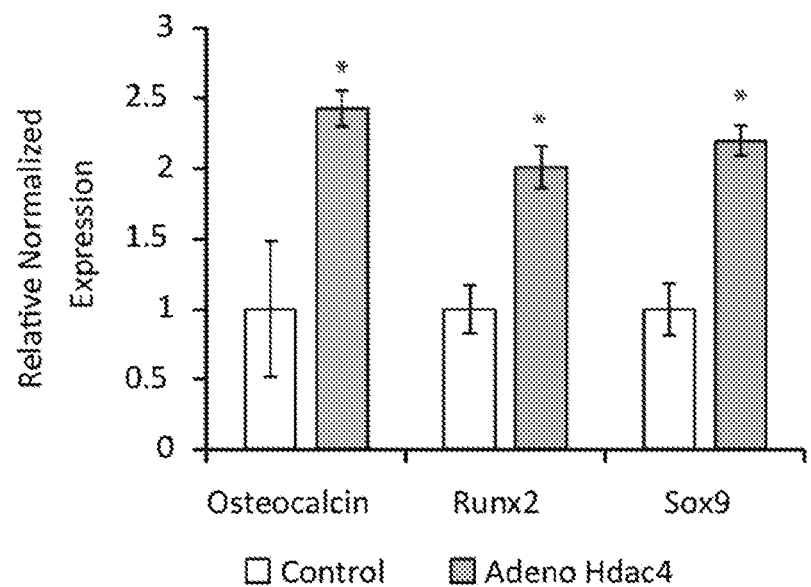

FIG. 2C: Aortic rings were transduced with adenoviral vector encoding for flag tagged HDAC4 or control betal-gal and were grown for 14 days in control media. Osteochondrogenic markers were analyzed using qRT-PCR Gene expression. Data are shown as means±SEM (n=6), normalized to control. Two tailed unpaired Student's t-test, *P<0.05.

Figure 2D:
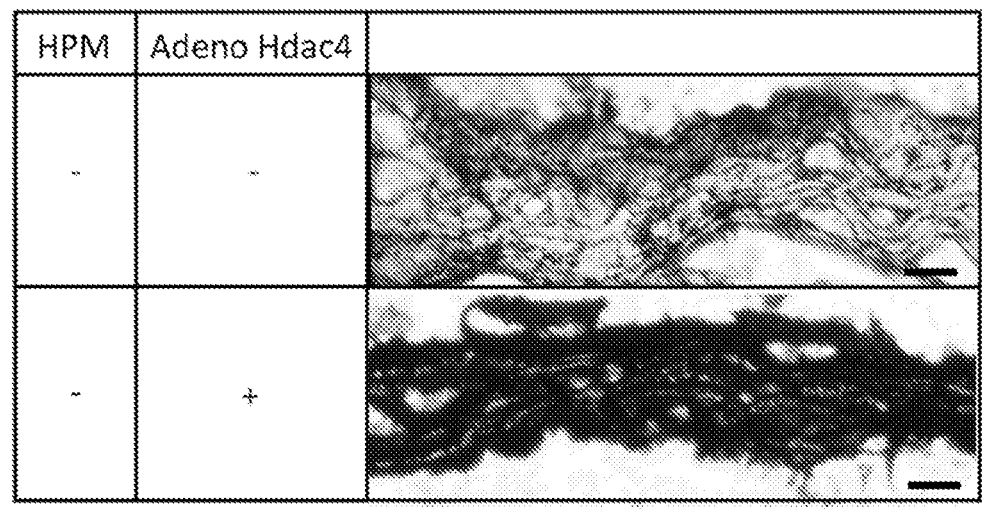

FIG. 2D: Histological sections of control beta-gal or HDAC4 transduced aortic rings in control medium after 14 day, stained black for calcium with Von Kossa stain. Representative images are shown. Scale bar=20 μm.

Figure 2E:
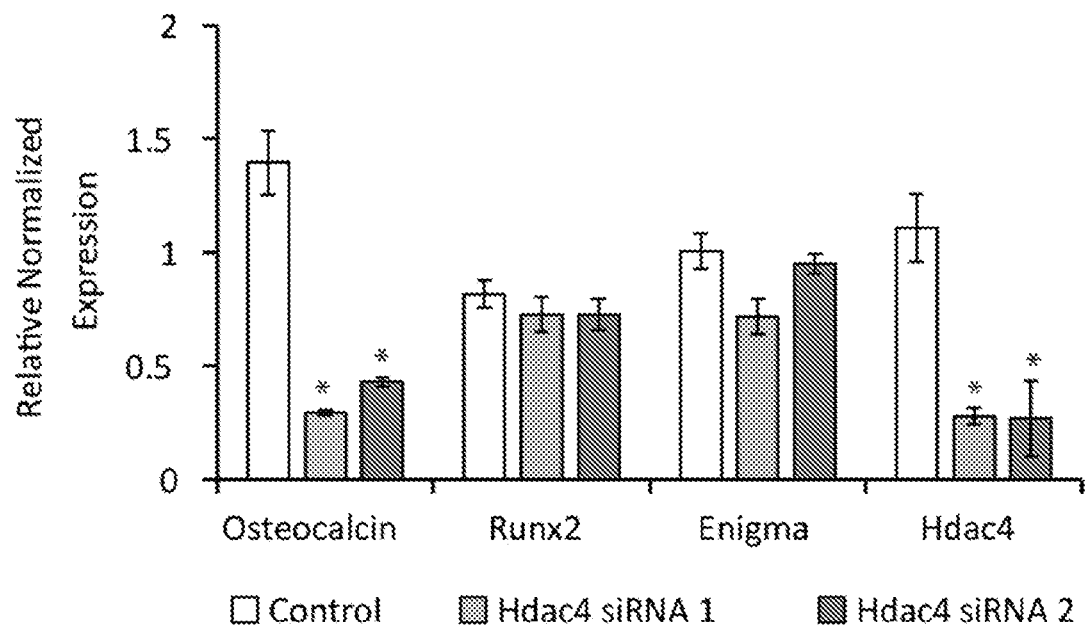

FIG. 2E: VSMCs were transfected with two different siRNAs for HDAC4 or with control siRNA. Gene expression qRT-PCR analysis shows similar level of knockdown of HDAC4 for the two siRNAs and inhibition of the osteochondrogenic marker Osteocalcin. Data are shown as means±SEM (n=5), relative to zero. Two tailed unpaired Student's t-test, *P<0.05 vs. control.

Figure 2F:
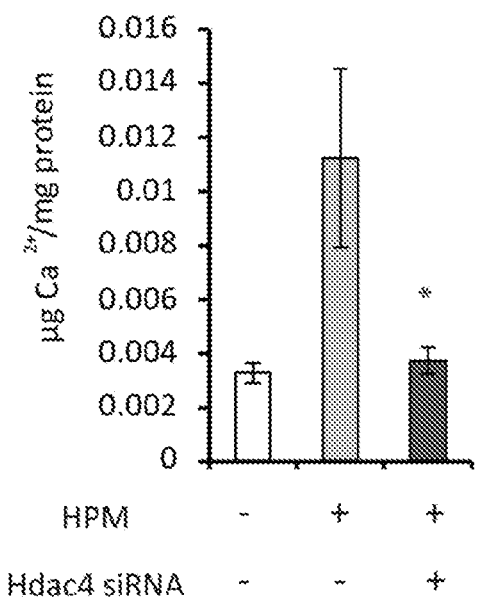

FIG. 2F: O-cresolphthalein calcium colorimetric assay of VSMCs transfected with scrambled siRNA after two weeks treatment with control media (white) or HPM (light grey), or VSMCs transfected with HDAC4 siRNA in HPM (dark grey). Data are shown as means±SEM (n=8), normalized to protein concentration. Two tailed unpaired Student's t-test, *P<0.05 vs. control siRNA.

FIGS. 2G-2J. Expanded view FIG. 2: degree of HDAC4 knock down and over expression FIG. 2G: Western blot analysis and quantification showing the degree of HDAC4 protein over expression after viral transduction in VSMCs. Data are shown as single data points and mean (n=2).

Figure 2G:
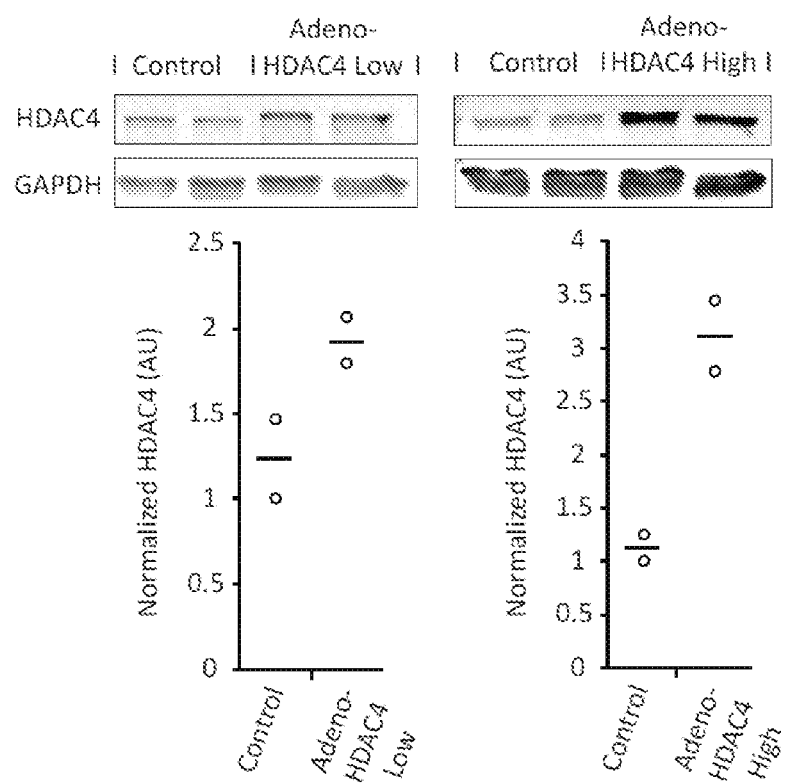
Figure 2H:
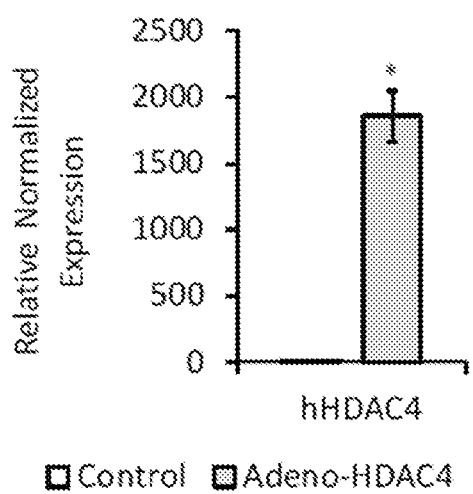

FIG. 2H: qRT-PCR with human specific HDAC4 primers in aortic rings showing effective viral transduction of Ad-HDAC4. This analysis however cannot be used to quantify the degree (fold-ratio) of HDAC4 overexpression over endogenous mouse HDAC4, since the level of human HDAC4 in control rings is zero.

Figure 2I:
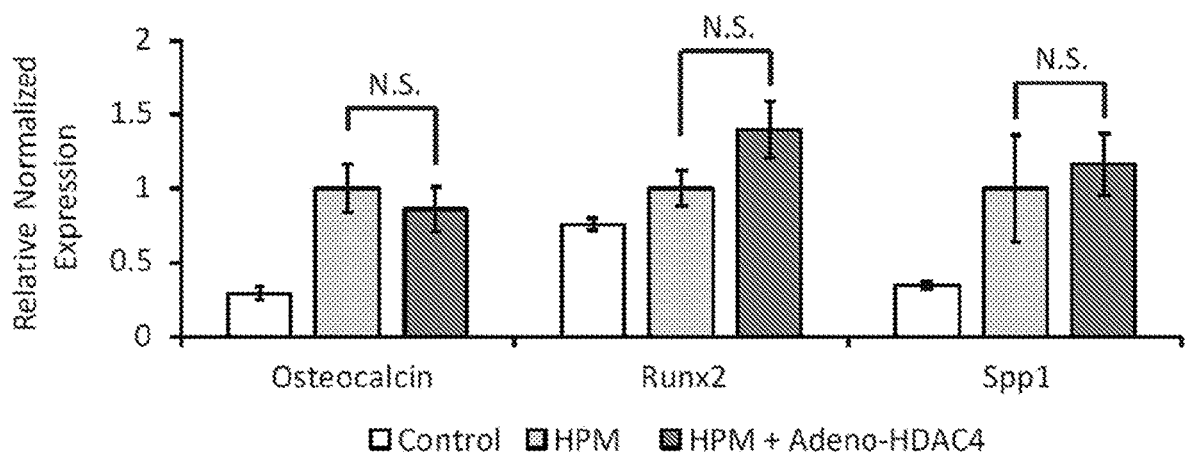

FIG. 2I: Aortic rings were transduced with adenoviral vector encoding for flag tagged HDAC4 or control betal-gal and were grown in HPM or control media. Gene expression qRT-PCR analysis for osteochondrogenic markers was performed. Data are shown as means±SEM (n=4), relative to zero. Two tailed unpaired Student's t-test. N.S. P>0.05.

Figure 2J:
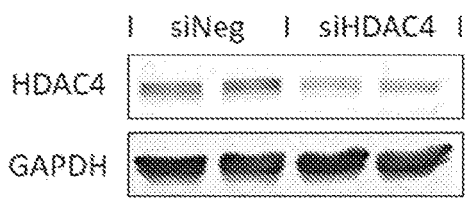
Figure 2J:
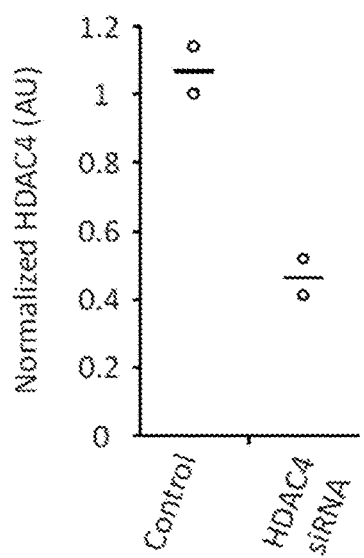

FIG. 2J: Western blot analysis and quantification showing the degree of HDAC4 protein knock-down in VSMCs in response to HDAC4 siRNA transfection. Data are shown as single data points and mean (n=2).

FIGS. 3A-3D: HDAC4 shows exclusive cytoplasmic localization in VSMCs.

Figure 3A:
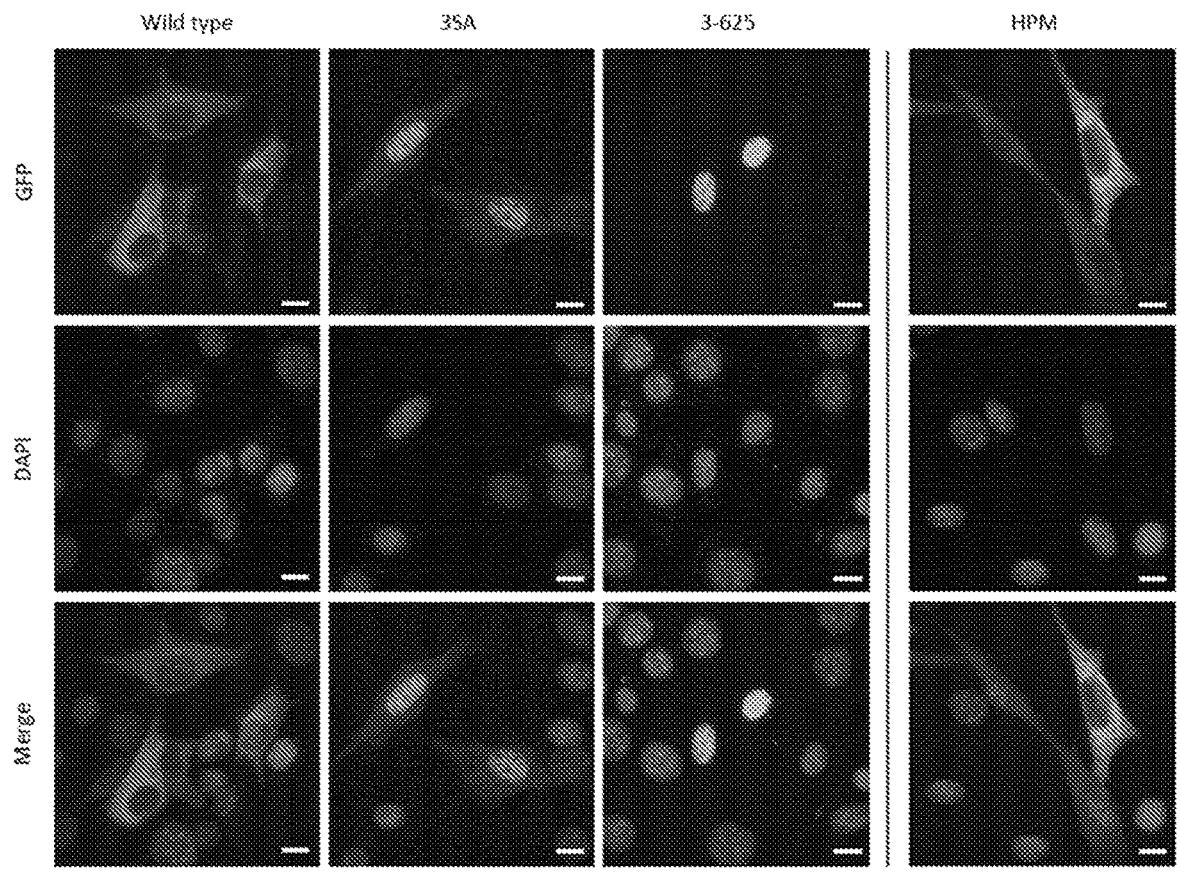

FIG. 3A: VSMCs were transfected with the indicated HDAC4 constructs (expanded view FIG. 3A) to examine their intra-cellular localization. The wild type HDAC4 transfected VSMCs were also grown in HPM to observe its effect on HDAC4 localization. Nuclei were counterstained with Dapi. High magnification representative images are shown, demonstrating that wild type HDAC4 was exclusively cytoplasmic in control and HPM media and the 3SA and 3-625 HDAC4 constructs are entirely nuclear. Scale bar=10 μm.

Figure 3B:
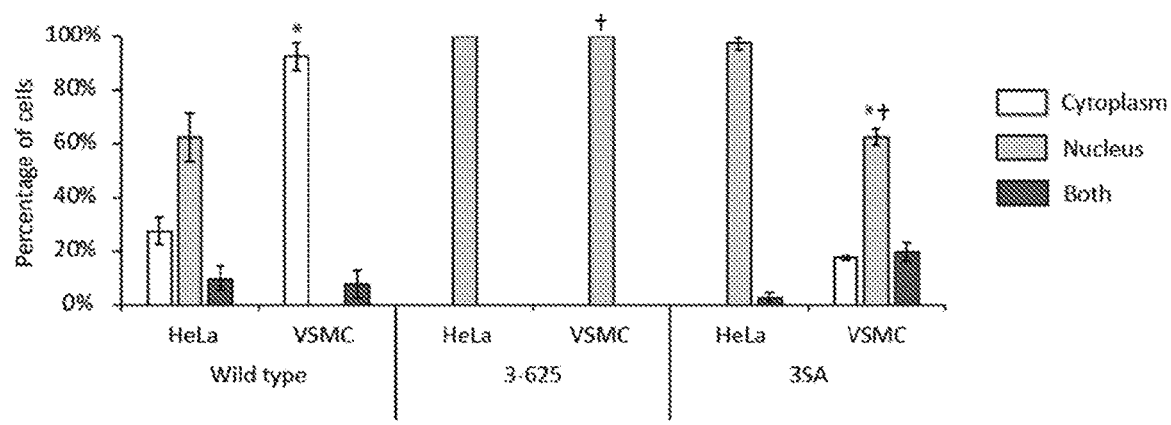

FIG. 3B: VSMCs or control HeLa epithelial cells were transfected with the indicated HDAC4 GFP constructs. Dapi staining was used to mark the nucleus. HDAC4 localization was scored automatically using CellProfiler analysis software as being exclusively cytoplasmic (white), exclusively nuclear (light grey) or as occupying both a cytoplasmic and nuclear localization (dark grey). Data are shown as means±SD (n=80 cells at least in each group). Chi square proportion test, *p<0.001 between VSMCs and HeLa cells for each construct, tp<0.001 between indicated construct distribution and wild type HDAC4 in VSMCs.

Figure 3C:
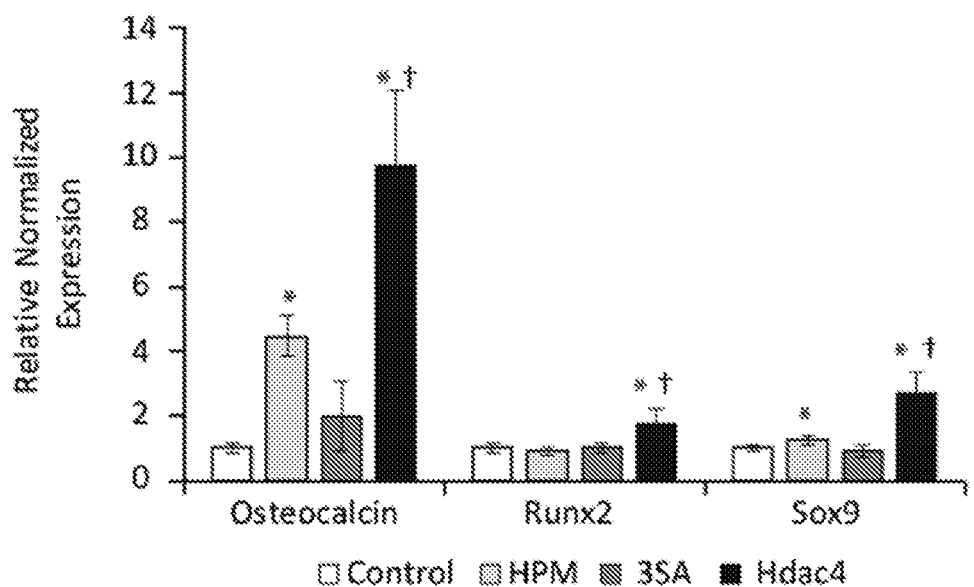

FIG. 3C: VSMCs were transfected with wild type HDAC4 or 3SA HDAC4 and grown in normal media for 7 days. qRT-PCR analysis of osteochondrogenic markers is shown. Data are shown as means±SEM (n=9), normalized to control. Two tailed unpaired Student's t-test, *P<0.05 vs. control, tp<0.05 vs. 3SA HDAC4.

Figure 3D:
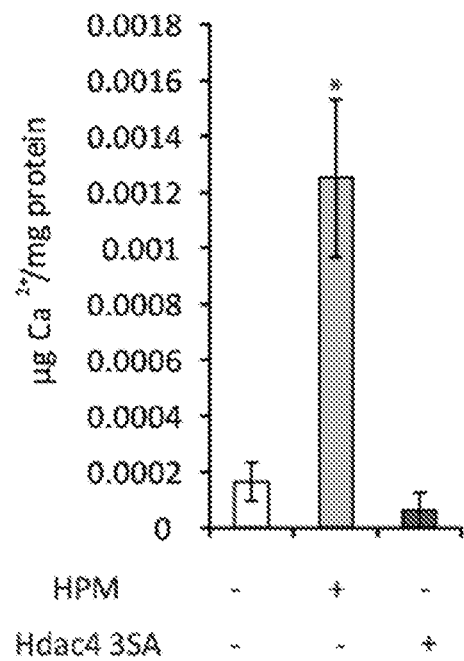

FIG. 3D: O-cresolphthalein calcium colorimetric assay of VSMCs transfected with lacZ in control media (white) or HPM (light grey), or VSMCs transfected with 3SA HDAC4 in control media (dark grey). Data are shown as means±SEM (n=8), normalized to protein concentration. Two tailed unpaired Student's t-test, *P<0.05.

Figure 3E:
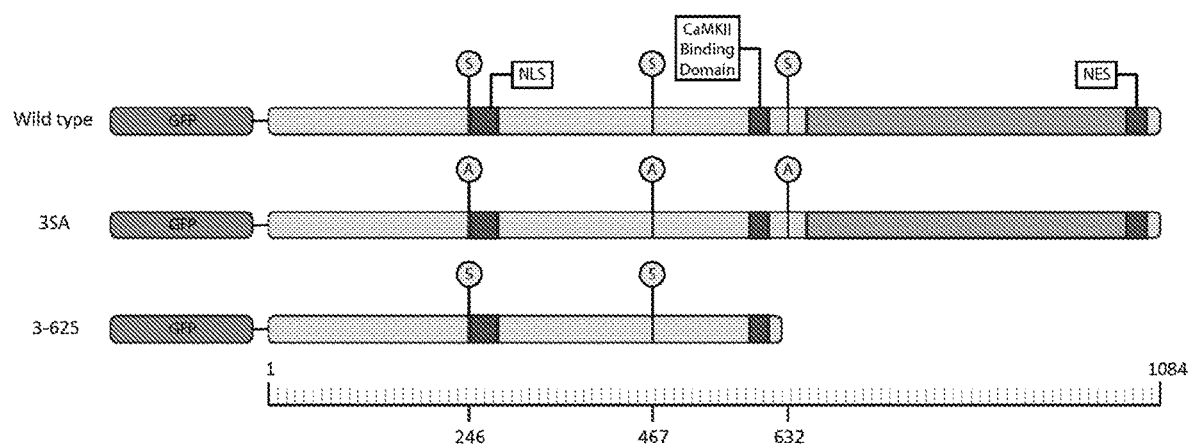
Figure 3F:
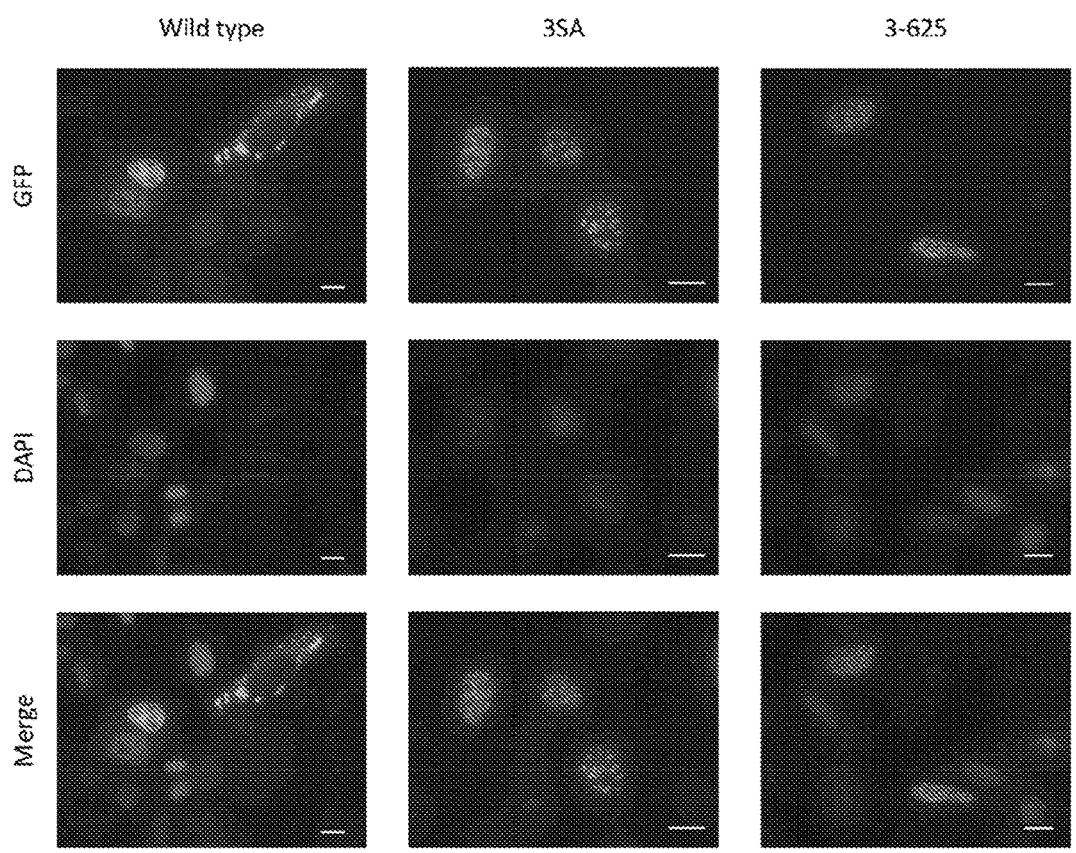
Figure 3G:
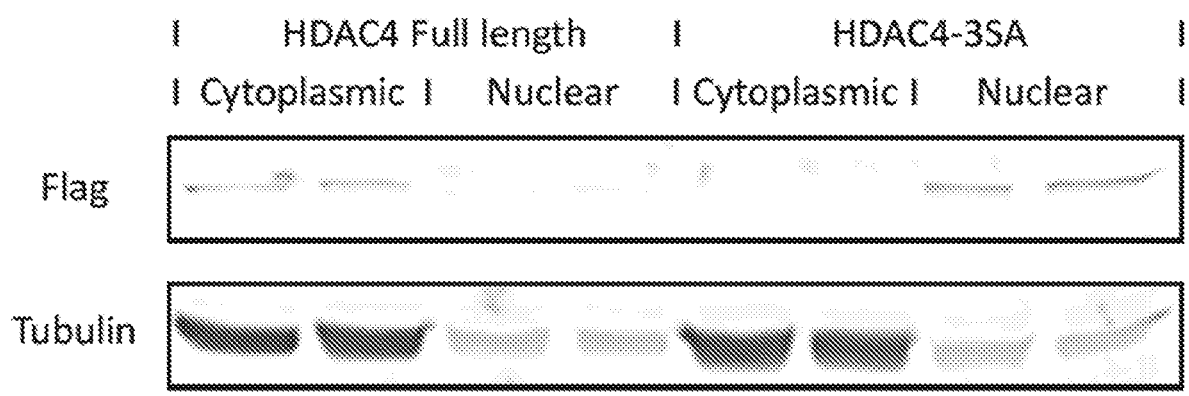

FIGS. 3E-3G: HDAC4 constructs and localization in HeLa cells.

FIG. 3E: GFP tagged constructs of HDAC4: Wild type—full length HDAC4 protein. 3SA—full length HDAC4 protein, in which 3 amino acids: $Ser^{246}$, $Ser^{467}$, and $Ser^{632}$ were mutated to Alanine. 3-625—The N-terminal fragment of HDAC4 containing the first 3-625 amino acids of the protein that includes the NLS but not the NES.

FIG. 3F: HeLa cells were transfected with the different HDAC4 constructs to examine their intra-cellular localization. Cells were fixed with formaldehyde and nuclei were counterstained with Dapi. High magnification representative images are shown. Scale bar=10 μm.

FIG. 3G: VSMCs were transduced with adenoviral vector encoding for flag tagged HDAC4 or flag tagged 3SA HDAC4. Cytoplasmic and nuclear protein extracts were obtained and western blot was performed using anti-flag antibody. Anti-Tubulin immunoblot was used as loading control, and to mark the cytoplasmic fraction.

Figure 4A:
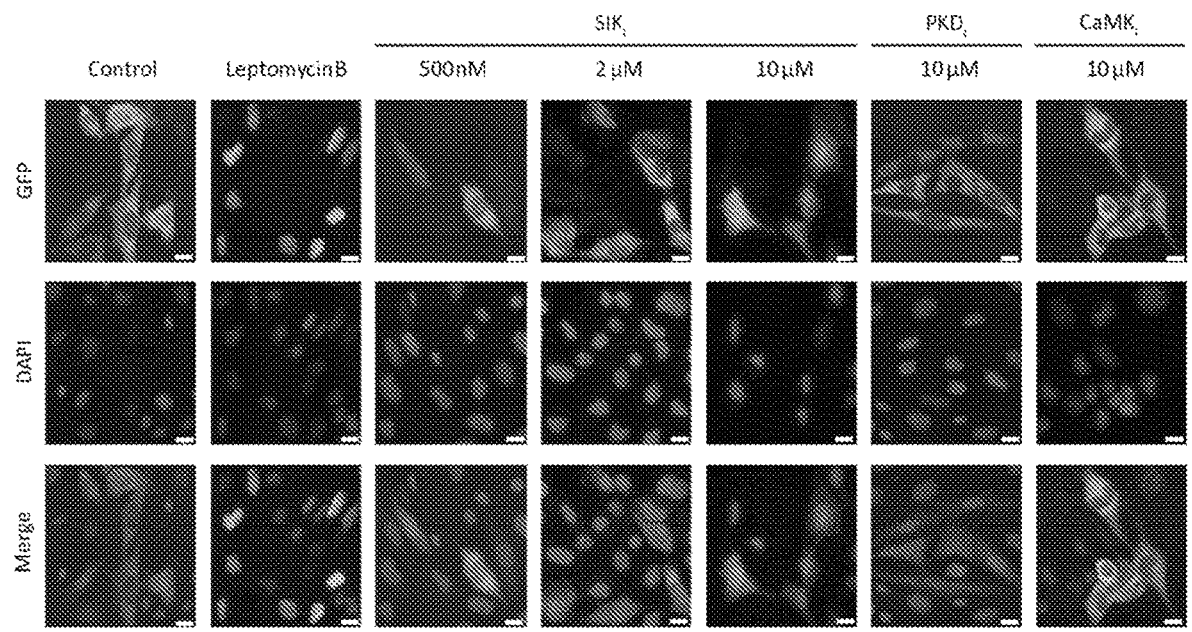
Figure 4B:
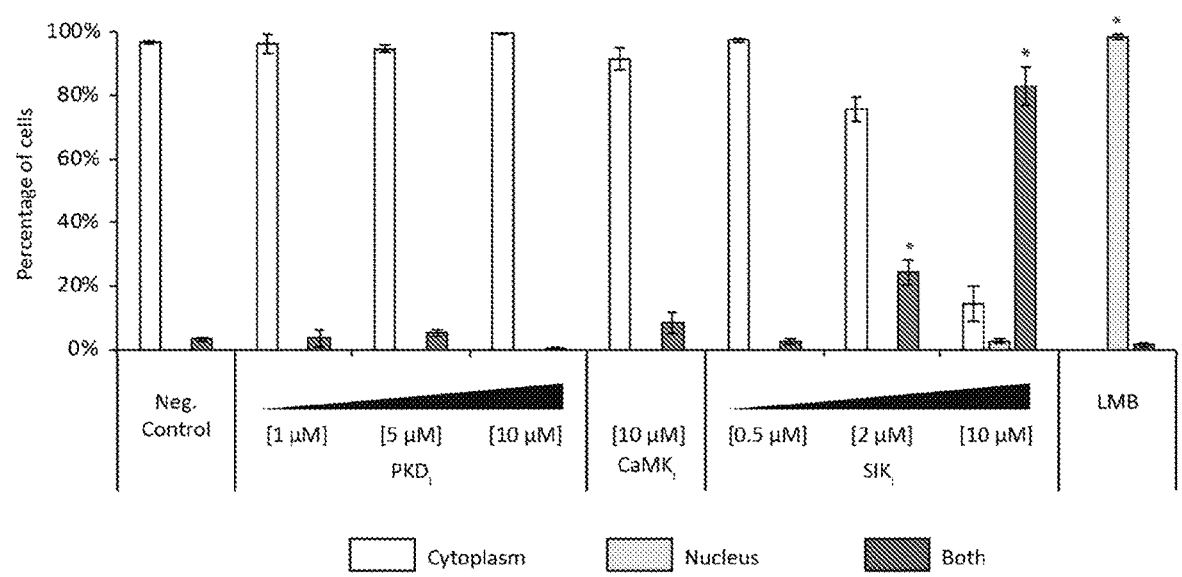

FIGS. 4A-4B: HDAC4 cytoplasmic localization is controlled by the activity of Salt inducible kinase (SIK).

FIG. 4A: Representative images of VSMCs transfected with wild type GFP-HDAC4 and treated with the indicated inhibitor and concentration: LMB-leptomycin B, PKDi-CID 2011756, CaMKi-KN-93, SIKi-HG-9-91-01. DAPI staining was used to mark the nucleus. The nuclear export inhibitor Leptomycin B was used as a positive control and induced nuclear accumulation of GFP-HDAC4. The pan-SIK inhibitor induced dose dependent nuclear accumulation of GFP-HDAC4. Scale bar=10 μm.

FIG. 4B: HDAC4 localization was scored automatically as being exclusively cytoplasmic (white), exclusively nuclear (light grey) or as occupying both a cytoplasmic and nuclear localization (dark grey). Data are shown as means±SD (n=250 cells at least in each group). Chi square proportion test *p<0.001 vs negative control.

Figure 4C:
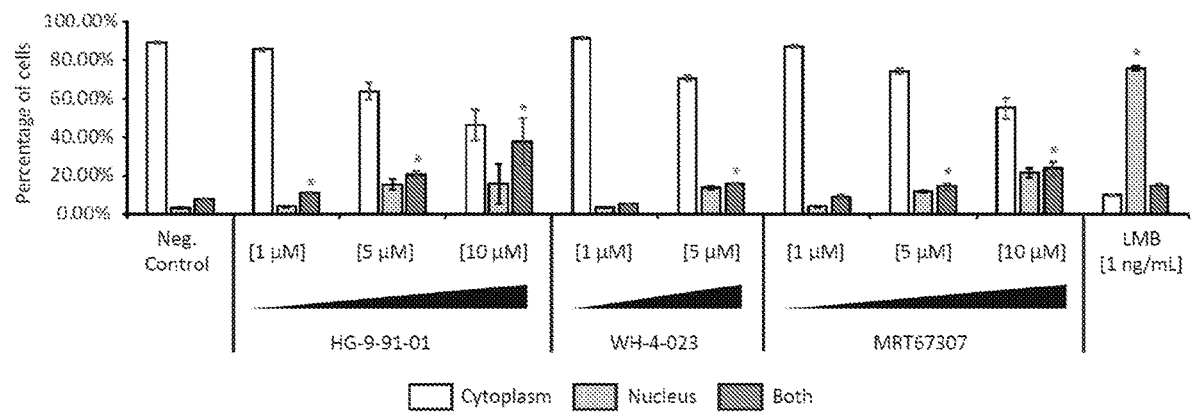
Figure 4D:
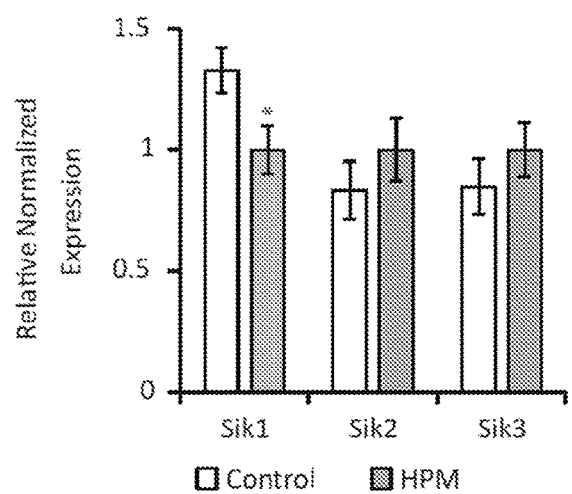
Figure 4E:
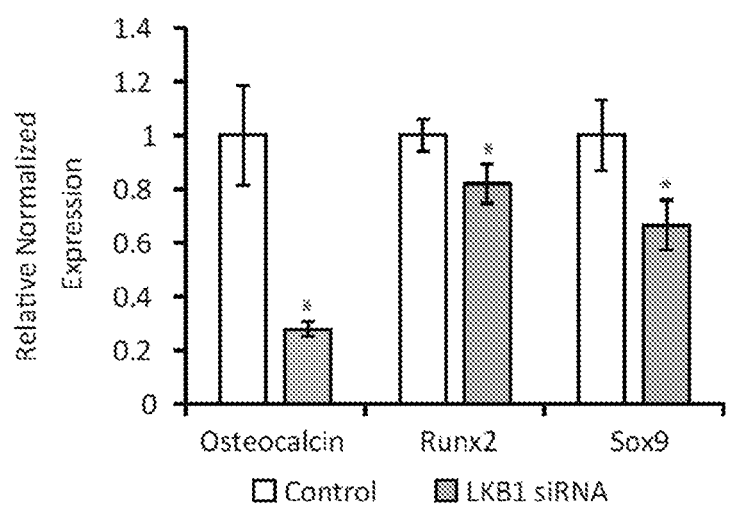

FIGS. 4C-4E: Different SIK inhibitors control HDAC4 localization

FIG. 4C: GFP-HDAC4 localization after treatment with the indicated SIK inhibitors and concentration was scored automatically as being exclusively cytoplasmic (white), exclusively nuclear (light grey) or as occupying both a cytoplasmic and nuclear localization (dark grey) using CellProfiler cell image and analysis software[26]. All three pan-SIK inhibitors induced dose dependent nuclear accumulation of HDAC4. Data are shown as means±SD (n=275 cells at least in each group). Chi square proportion test, * p<0.001.

FIG. 4D: Gene expression qRT-PCR analysis of the three SIK isoforms in VSMCs shows modest downregulation of SIK1 and modest upregulation of SIK2 and SIK3 following treatment with HPM (grey). Data are shown as means±SEM (n=4), relative to control. Two tailed unpaired Student's t-test, *P<0.05.

FIG. 4E: Gene expression qRT-PCR analysis of VSMCs transfected with control or LKB1 siRNA and grown in HPM for 7 days. Data are shown as means±SEM (n=4), normalized to control. Two tailed unpaired Student's t-test, *P<0.05.

FIGS. 5A-5D: SIK inhibition blunts the calcification process in vitro and ex-vivo.

Figure 5A:
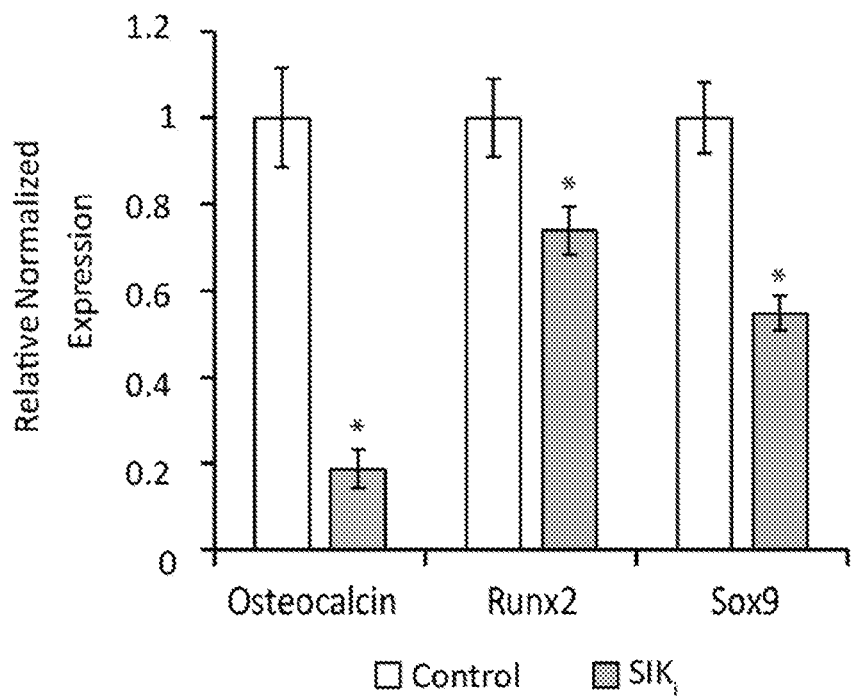

FIG. 5A: VSMCs were grown for 7 days in HPM with control (DMSO) or 1 µM HG-9-91-01 (SIKi). Osteochondrogenic markers expression was analyzed using qRT-PCR. Data are shown as means±SEM (n=4), normalized to control. Two tailed unpaired Student's t-test, *P<0.05.

Figure 5B:
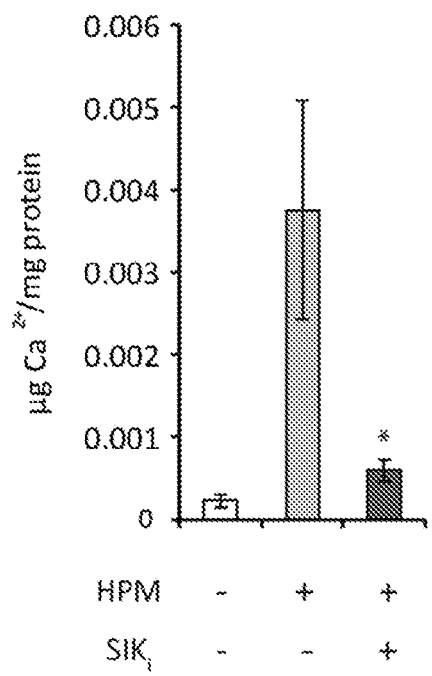

FIG. 5B: O-cresolphthalein calcium colorimetric assay of VSMCs grown in HPM in the presence of HG-9-91-01 for 14 days. Data are shown as means±SEM (n=7), normalized to protein concentration. Two tailed unpaired Student's t-test, *P<0.05 vs. HPM control treatment.

Figure 5C:
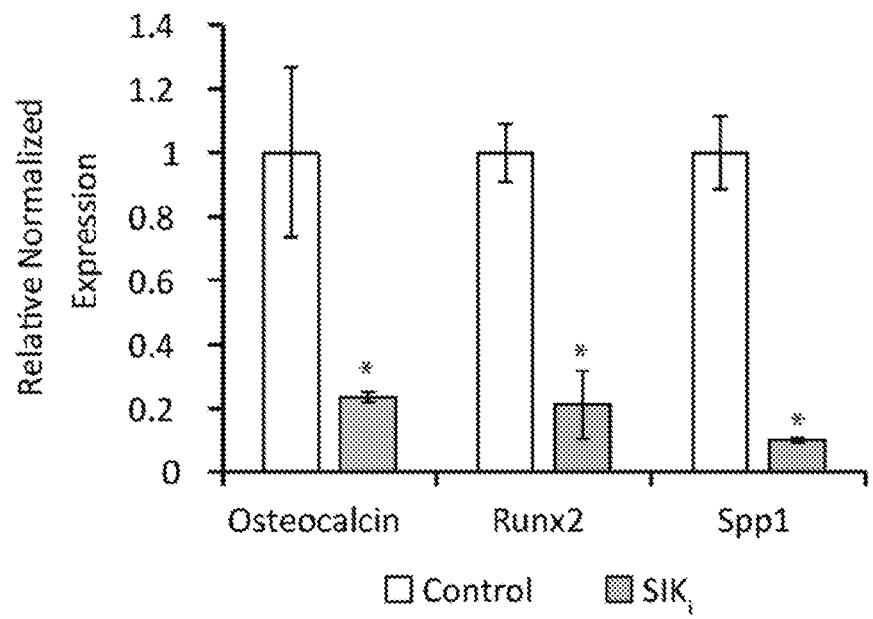

FIG. 5C: Aortic rings were grown for 14 days in HPM with control (DMSO) or 1 µM HG-9-91-01 (SIKi). Osteochondrogenic markers expression was analyzed using qRT-PCR. Data are shown as means±SEM (n=6), normalized to control. Two tailed unpaired Student's t-test, *P<0.05.

Figure 5D:
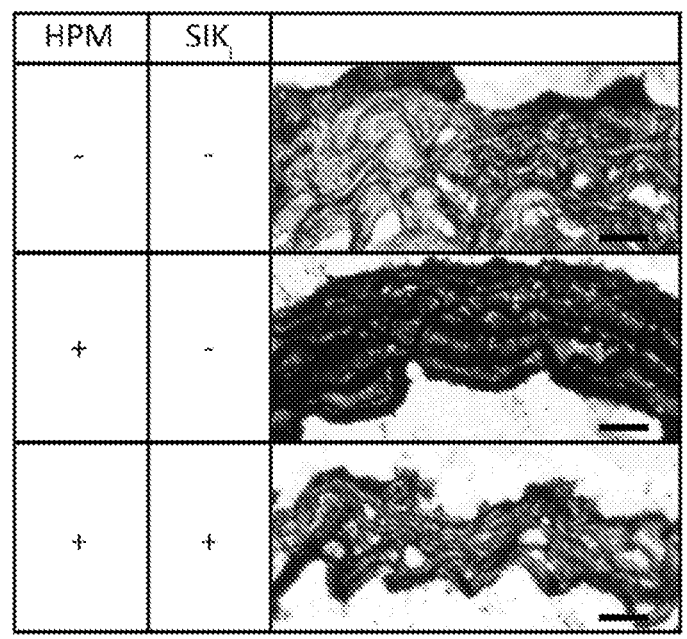

FIG. 5D: Representative images of aortic rings histological sections in control, HPM and HPM with HG-9-91-01 media, stained black for calcium with Von Kossa stain.

Figure 5E:
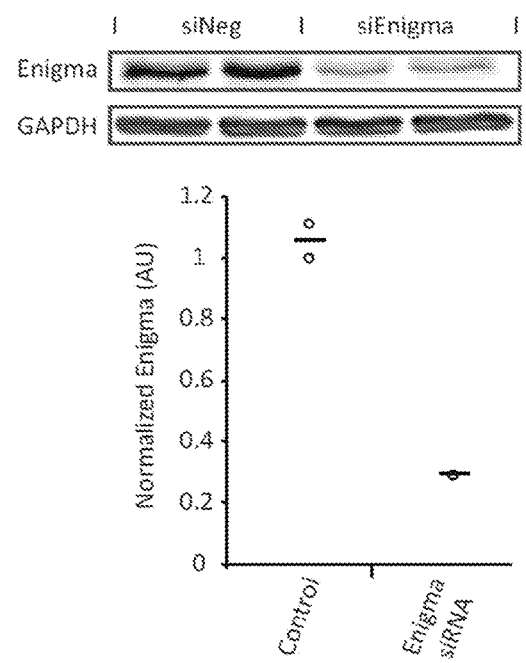
Figure 5F:
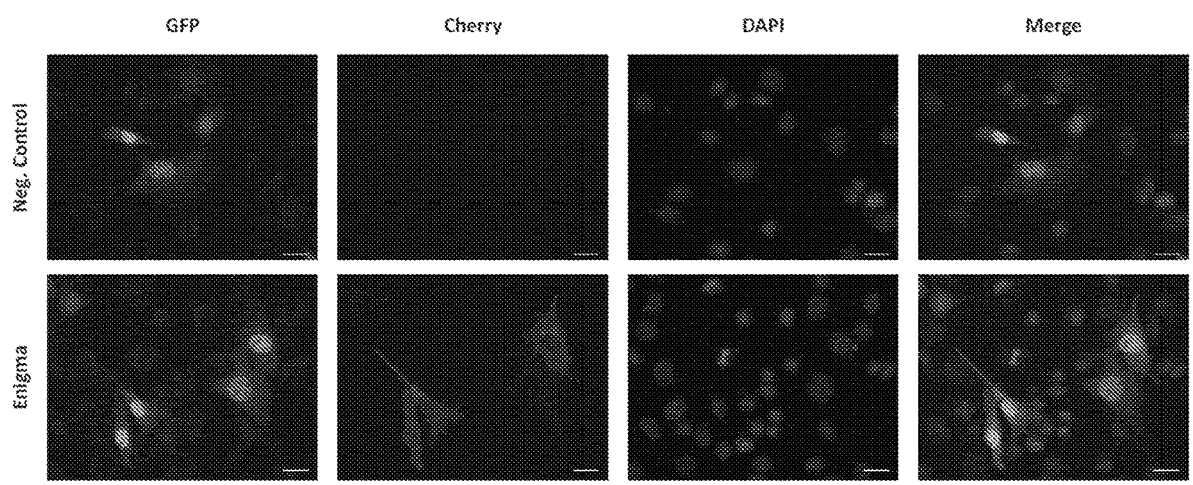

FIGS. 5E-5F: Enigma knock down and over expression

FIG. 5E: Western blot analysis and quantification showing the degree of ENIGMA protein knock-down in VSMCs in response to ENIGMA siRNA transfection. Data are shown as single data points and mean (n=2).

FIG. 5F: VSMCs were co-transfected with GFP-3SA HDAC4 and Cherry-ENIGMA plasmids to observe if ENIGMA over expression can force cytoplasmic localization of 3SA HDAC4. Representative images are shown. Scale bar=10 µm.

Figure 6A:
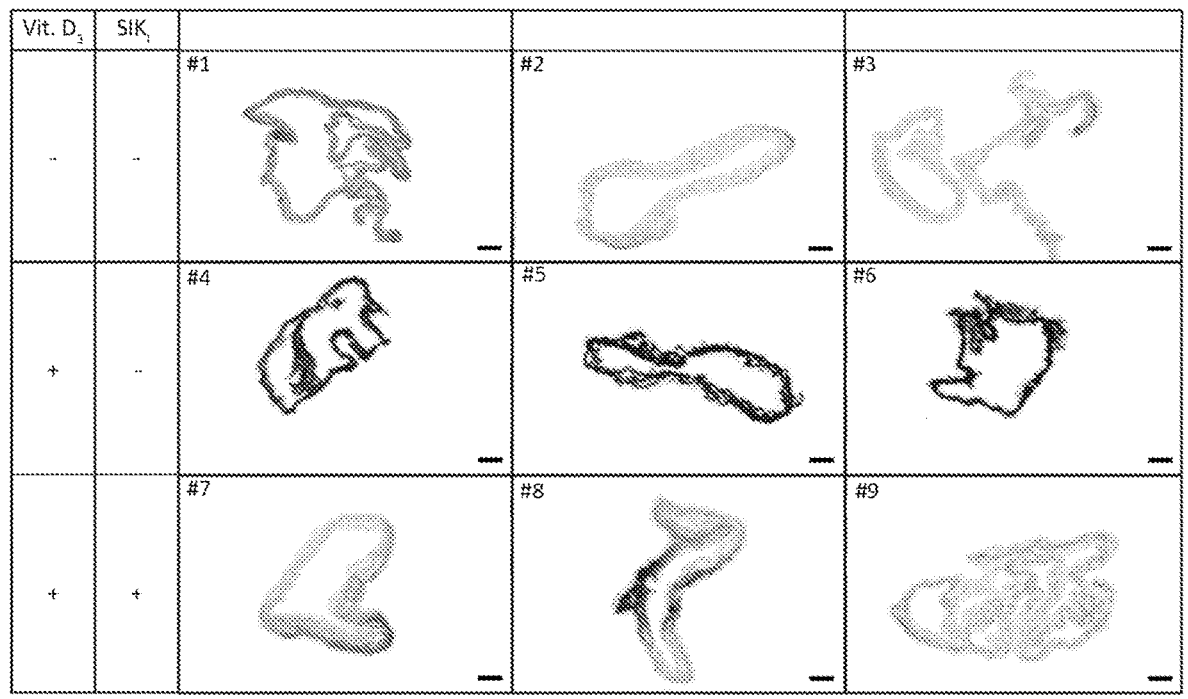
Figure 6B:
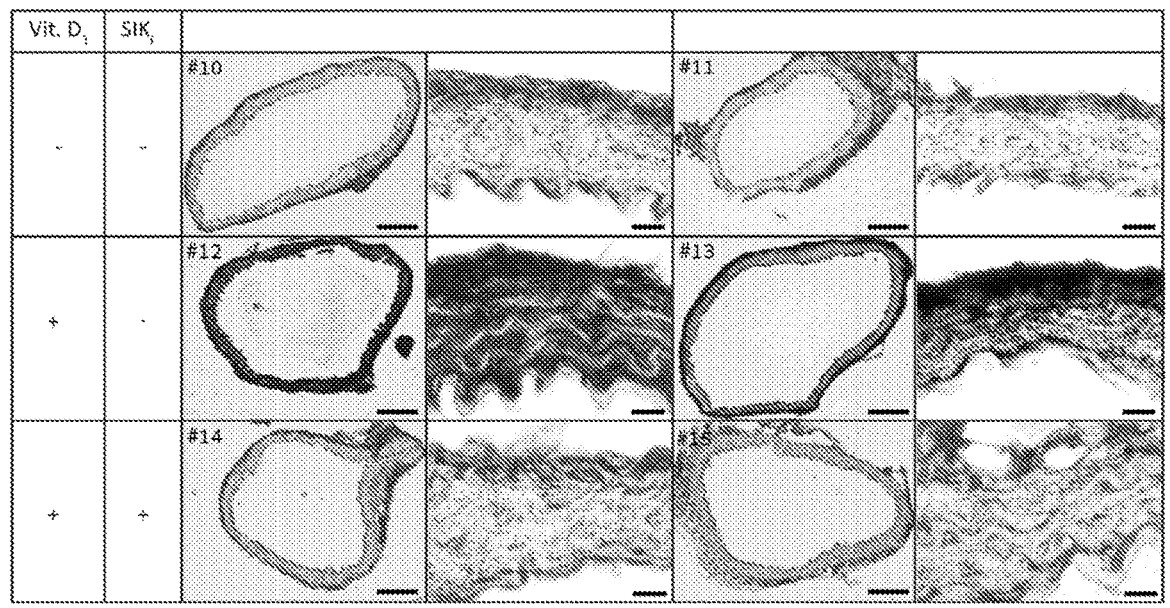
Figure 6C:
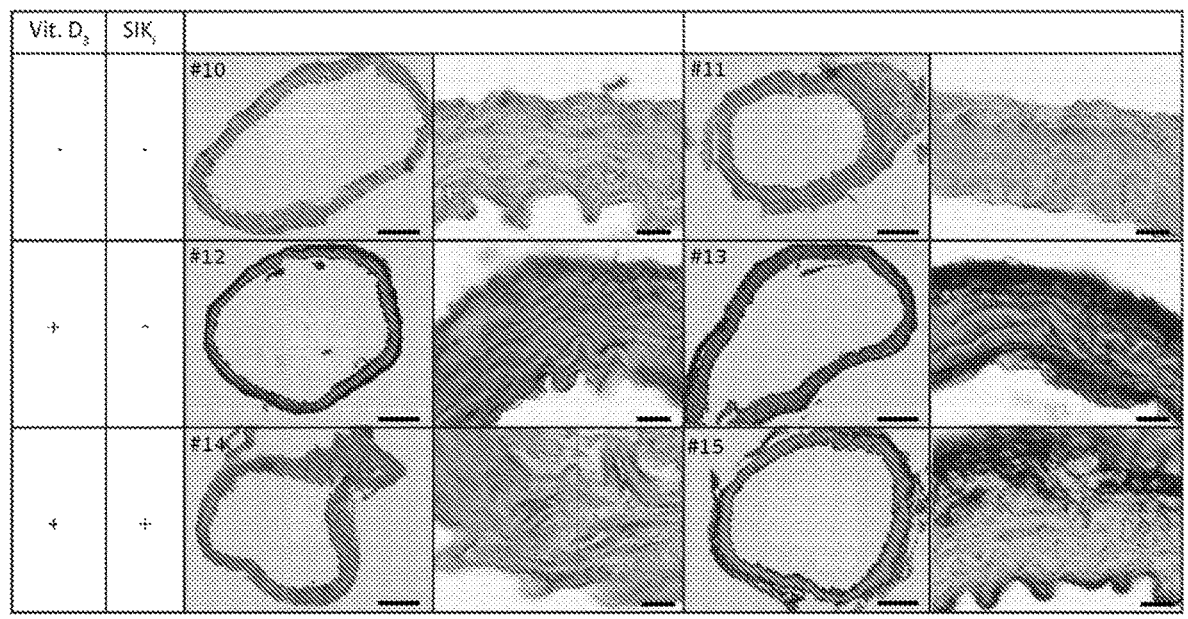
Figure 6D:
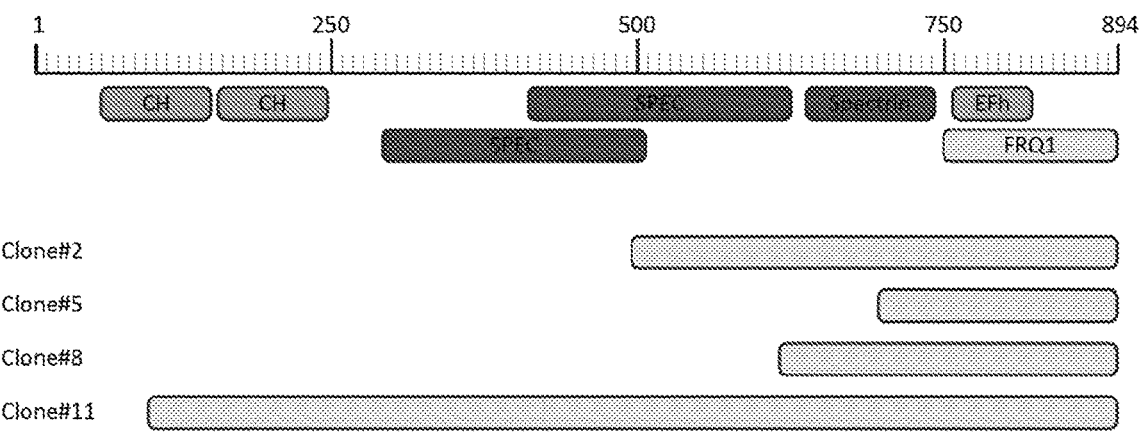

FIGS. 6A-6C: SIK inhibition blunts the calcification process in vivo.

FIG. 6A: Mice aortic cryosections of 3 groups: (1) control (top, mice #1-3), (2) vitamin $D_3$ (middle, mice #4-6), (3) vitamin $D_3$ and SIK inhibitor (bottom, mice #7-9) stained black for calcium with Von Kossa stain. Vitamin $D_3$ causes excessive aortic calcification which is blunted by SIK inhibitor treatment. Scale bar=100 µm.

FIG. 6B: Representative mice aortic paraffin thin sections of 3 groups: (1) control (top, mice #10-11), (2) vitamin $D_3$ (middle, mice #12-13), (3) vitamin $D_3$ and SIK inhibitor (bottom, mice #14-15) stained black for calcium with Von Kossa stain in low and high magnifications (Scale bars are 100 µm and 10 µm respectively).

FIG. 6C: Same mice aortic paraffin sections shown in B of 3 groups: (1) control (top, mice #10-11), (2) vitamin $D_3$ (middle, mice #12-13), (3) vitamin $D_3$ and SIK inhibitor (bottom, mice #14-15) stained red for calcium with Alizarin red calcium staining, in low and high magnifications (Scale bars are 100 µm and 10 µm respectively).

FIGS. 6D-6H: ENIGMA binds the cyto-skeletal proteins α-actinin and palladin and affect gene expression through the LINC complex FIG. 6D: Cartoon of the α-actinin protein with its known structural domains. Four independent α-actinin clones B1, B5, B8, B11 (grey) were found to bind ENIGMA PDZ domain using the yeast Ras recruitment system (RRS). All clones contained the c-terminal domain of α-actinin.

Figure 6E:
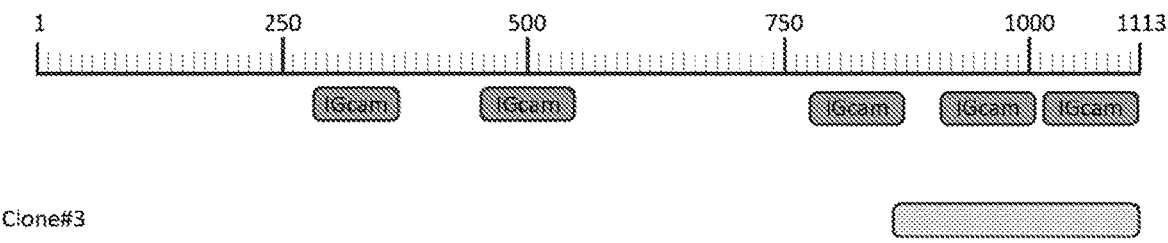

FIG. 6E: Cartoon of the Palladin protein with its known structural domains. One clone—B2 (grey) was found to bind ENIGMA through its c-terminal domain, using the yeast Ras recruitment system (RRS).

Figure 6F:
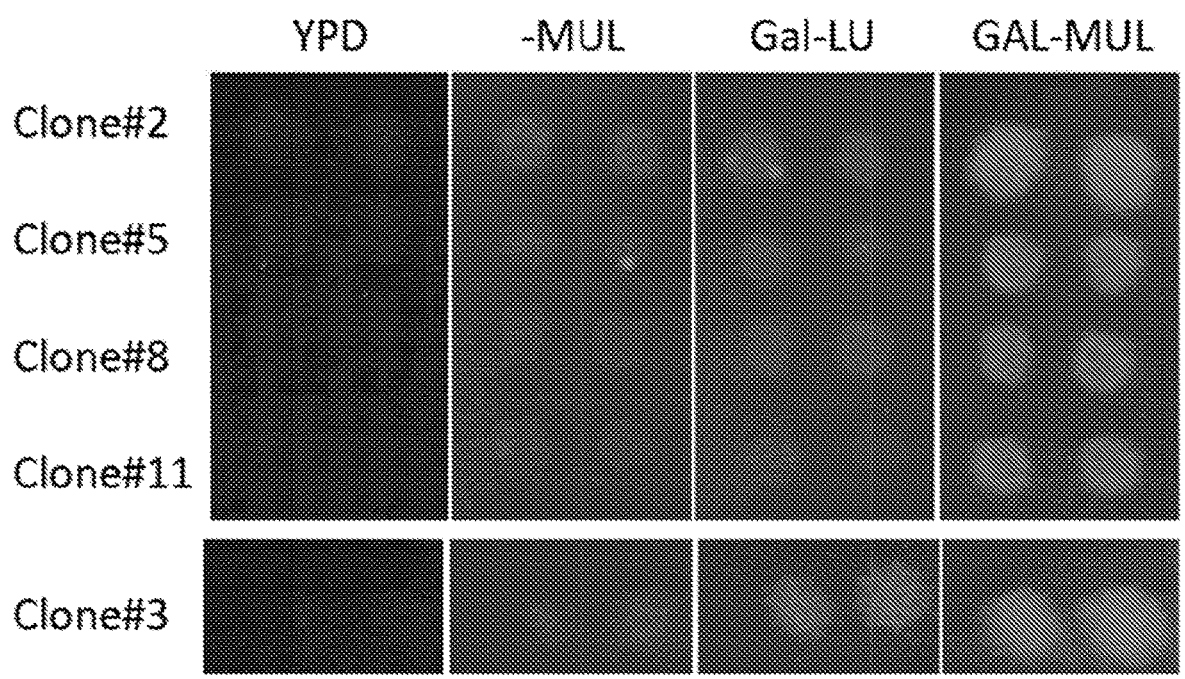

FIG. 6F: Expression from the bait plasmid is induced in media without Methionine (-M), while expression from the prey plasmid is induced by galactose containing media (GAL). All 5 positive clones conferred growth at 36° C., only when the expression from both bait and prey plasmid was turned on (GAL-MUL media), indicating true interaction.

Figure 6G:
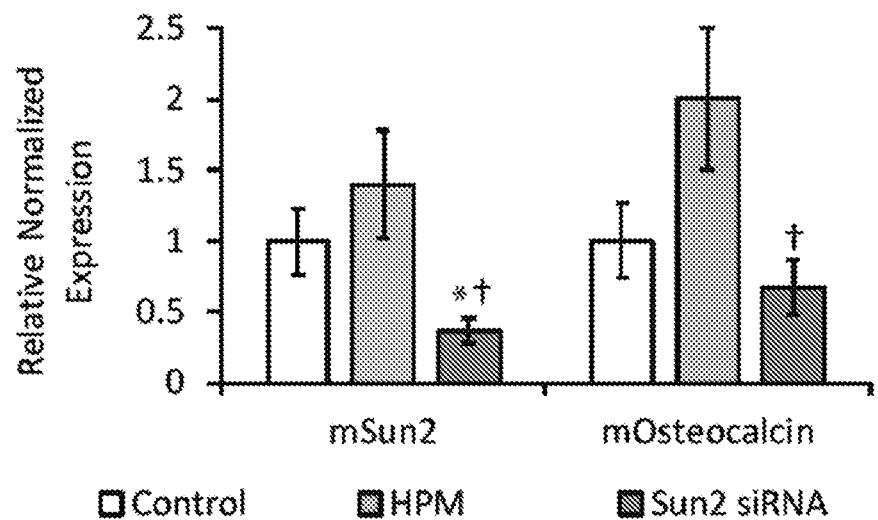

FIG. 6G: VSMCs were transfected with SUN2 siRNA or control scrambled siRNA, and Osteocalcin levels were analyzed by qRT-PCR. Data are shown as means±SEM (n=4), normalized to control. Two tailed unpair Student's t-test, *P<0.05.

Figure 6H:
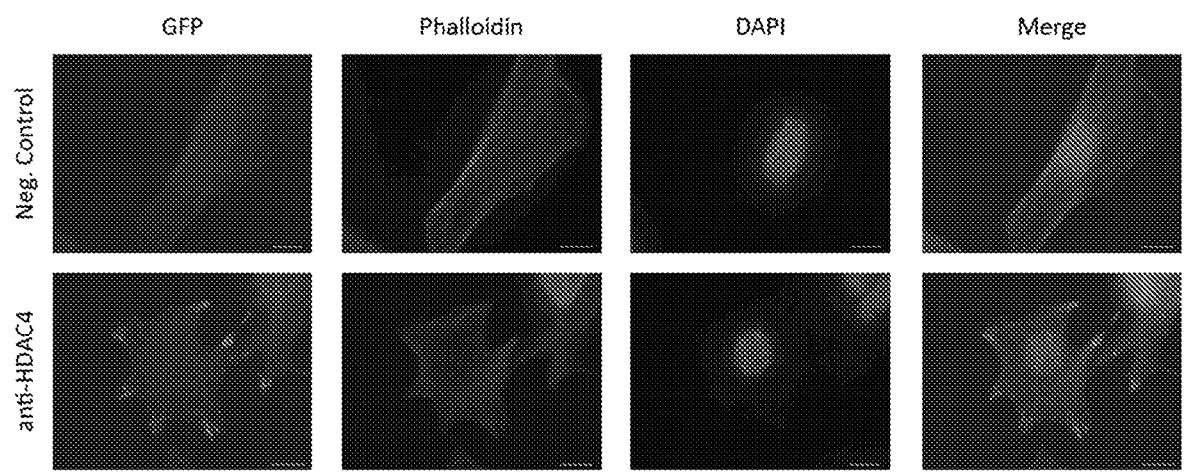

FIG. 6H: Wildtype VSMCs were fixed with formaldehyde, immune-stained with an anti-HDAC4 antibody (green), phalloidin (red) and nuclei were counterstained with Dapi (blue). Representative images are shown. Scale bar=10 µm FIGS. 7A-7E: HDAC4 N-terminal binds ENIGMA LIM domains.

Figure 7A:
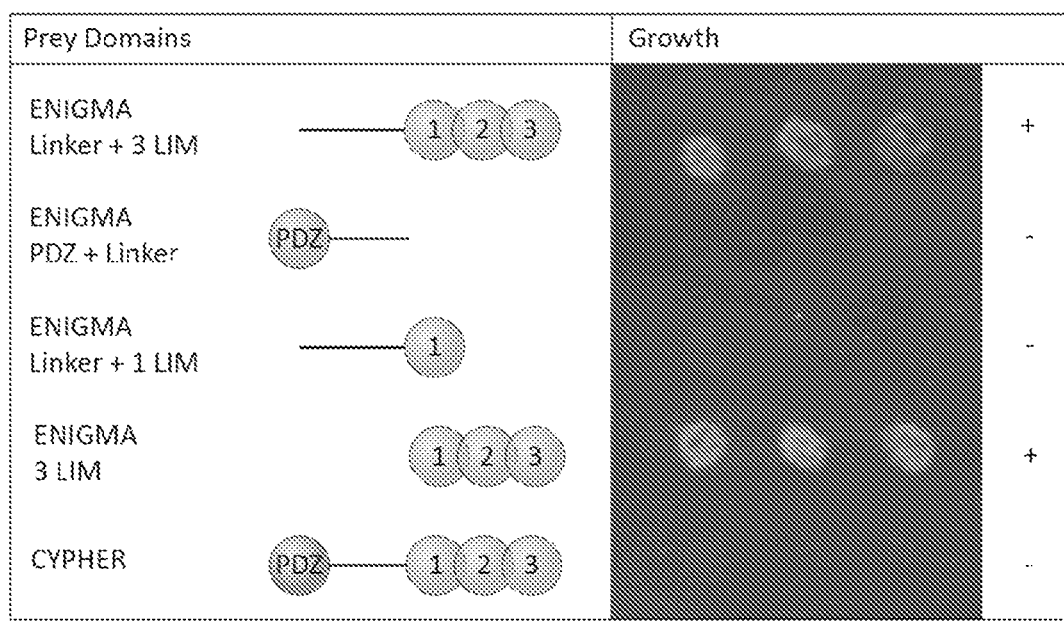

FIG. 7A: The yeast Ras recruitment system (RRS) was used to discover HDAC4 binding partners. Interaction between the bait and prey proteins allows the Cdc25-2 temperature sensitive yeast strain to grow at 36° C. Cdc25-2 yeast cells were co-transfected with HDAC4 N-terminus (AA 3-625) and the indicated myristolated ENIGMA constructs or CYPHER and grown at 36° C. Only constructs containing the three LIM domains of ENIGMA conferred growth.

Figure 7B:
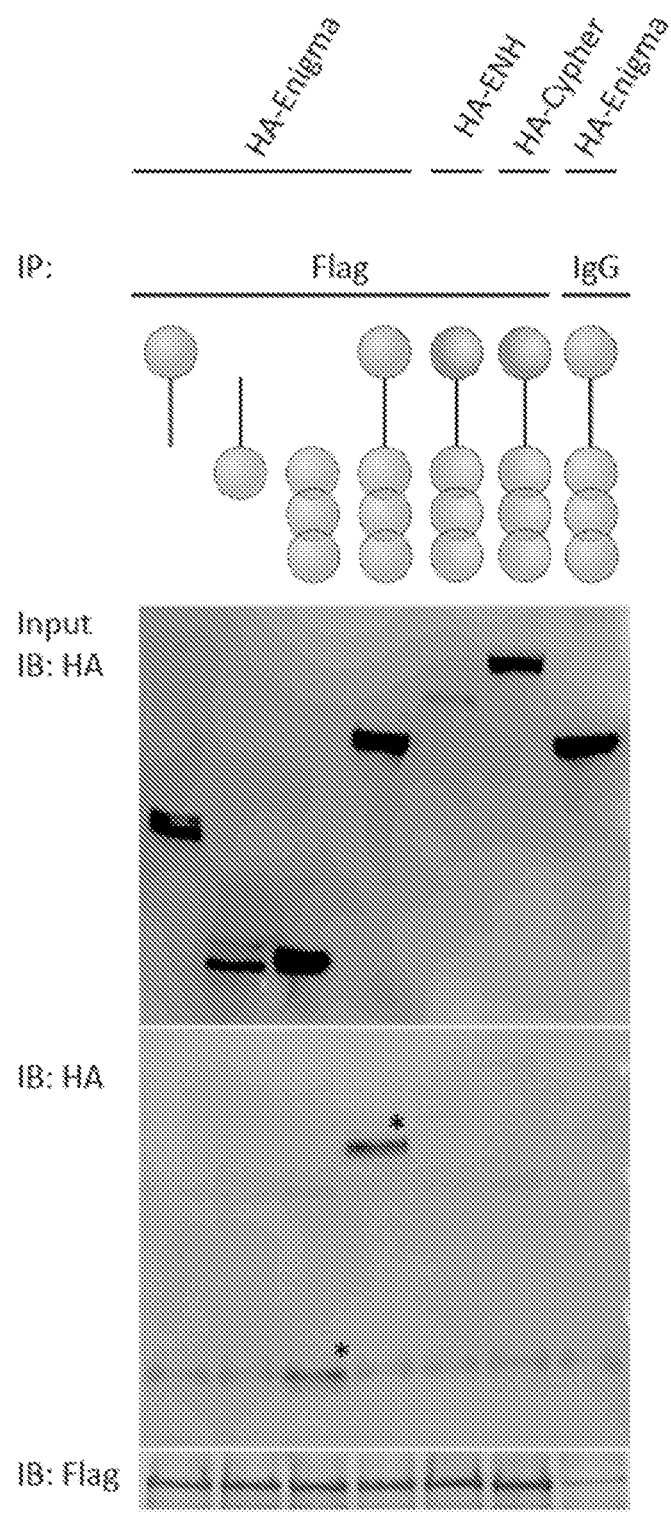
Figure 7C:
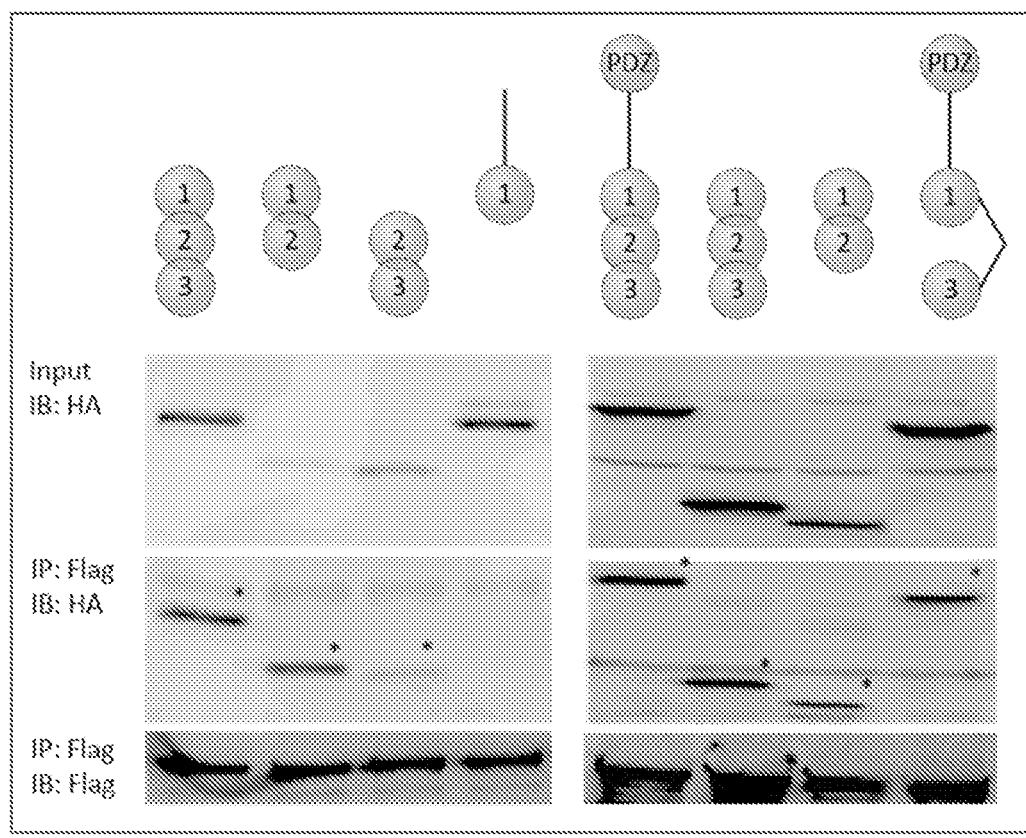

FIGS. 7B and 7C: Cells were co-transfected with Flag-HDAC4 and the indicated 3HA tagged ENIGMA constructs, 3HA tagged Enigma Homologue (ENH) or 3HA tagged CYPHER. Protein lysate was immunoprecipitated (IP) with an antibody recognizing Flag or IgG (negative control). Proteins were separated on SDS-page gel and immunoblotted (IB) with an antibody recognizing HA or Flag. Total protein extract (input, 10% of lysate) is also shown. The analysis shows that any combinations of two of the three LIM domains of ENIGMA, or all three LIM domains are sufficient for the interaction (C).

Figure 7D:
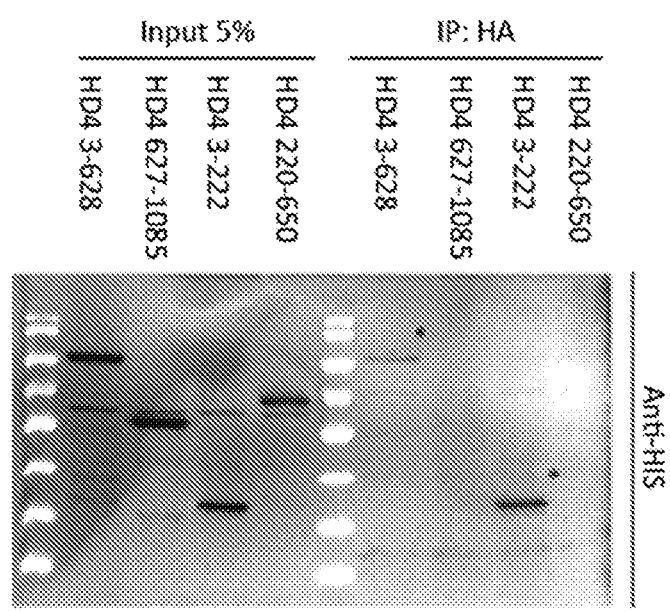
Figure 7E:
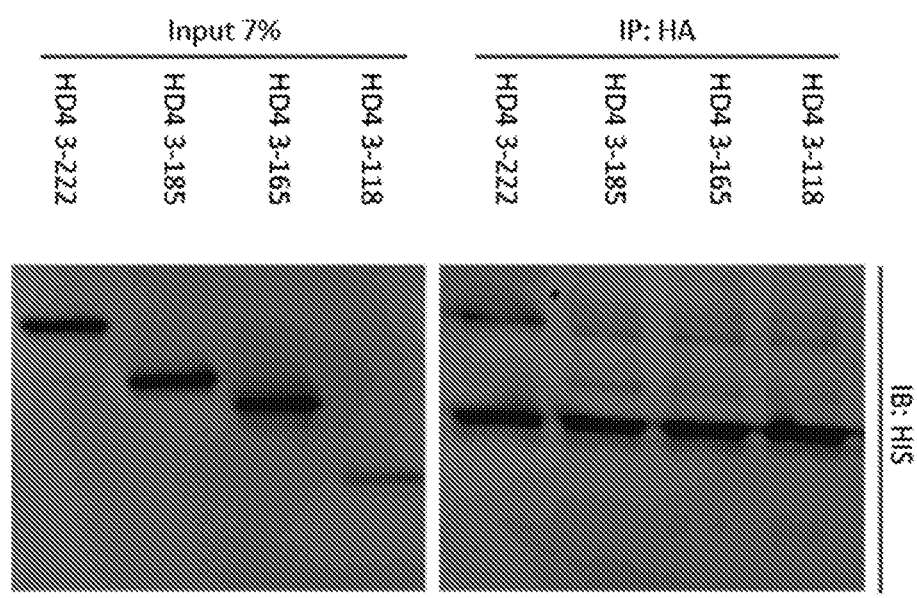

FIGS. 7D and 7E: Cells were co-transfected with HA-Enigma and the indicated 6×HIS tagged HDAC4 N-terminal construct. Protein lysate was immunoprecipitated (IP) with an antibody recognizing HA. Proteins were separated on SDS-page gel and immunoblotted (IB) with an antibody recognizing HIS. Total protein extract (input, 5% and 7% of lysate) is also shown. The analysis shows that ENIGMA binds the N-terminus of HDAC4, specifically the interaction requires amino acids 185-222.

FIGS. 8A-8E: ENIGMA co-localize with HDAC4 in the cytoplasm and promotes calcification in VSMCs.

Figure 8A:
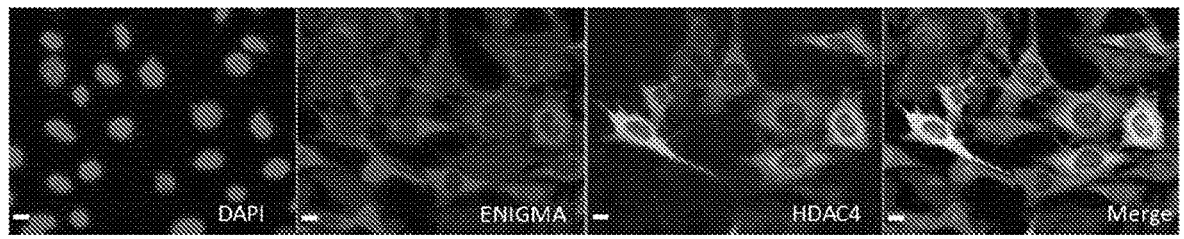

FIG. 8A: VSMCs were transfected with GFP-HDAC4, cells were immune-stained with an anti-ENIGMA antibody (red), and nuclei were counterstained with Dapi (blue). Representative images show cytoplasmic co-localization of ENIGMA and HDAC4. Scale bar=10 µm.

Figure 8B:
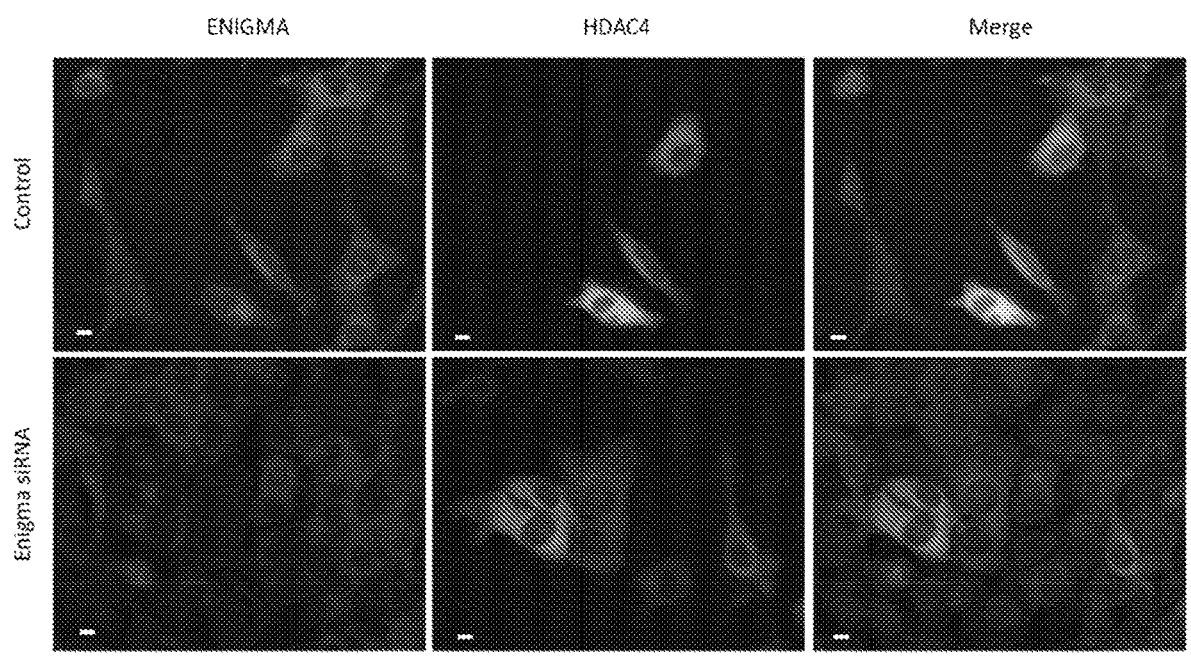

FIG. 8B: VSMCs were transfected with GFP-HDAC4 and ENIGMA siRNA or control scrambled siRNA and immune-stained with an antibody recognizing ENIGMA. Nuclei were counterstained with Dapi. Knockdown of ENGIMA did not change the cytoplasmic localization of HDAC4. Scale bar=10 µm.

Figure 8C:
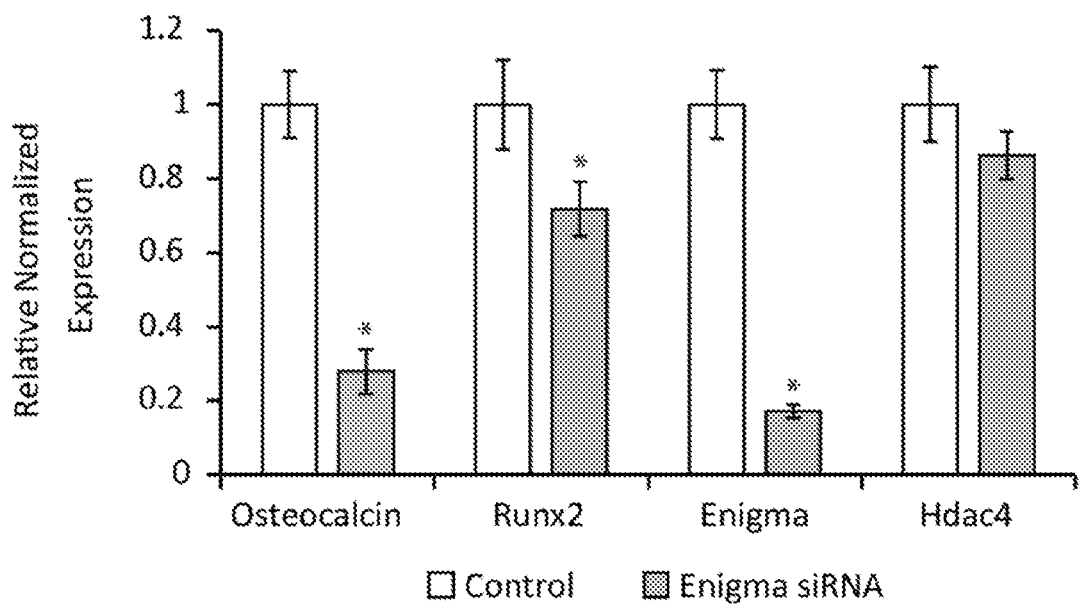

FIG. 8C: VSMCs were transfected with ENIGMA siRNA or control scrambled siRNA, and osteochondrogenic markers were analyzed by Data are shown as means±SEM (n=8), normalized to control. Two tailed unpaired Student's t-test, *P<0.05.

Figure 8D:
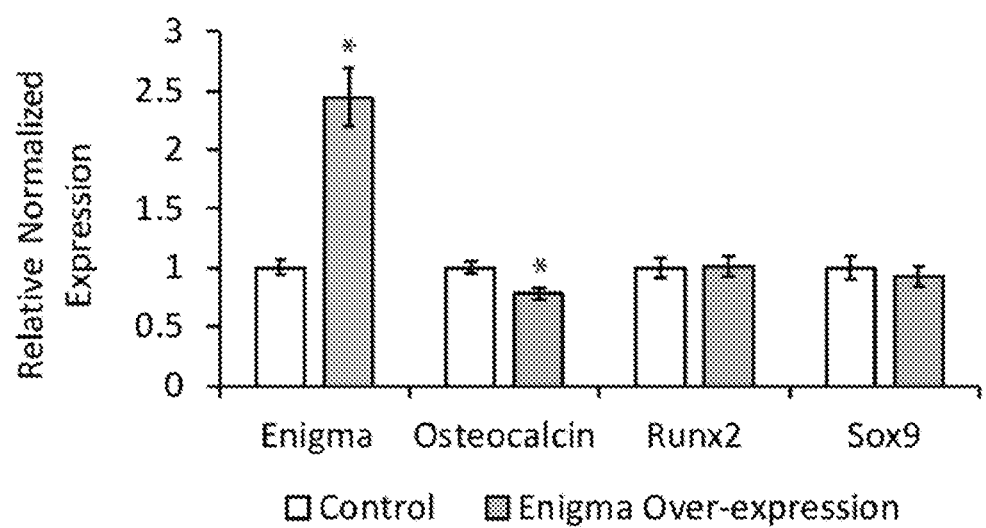

FIG. 8D: VSMCs were transfected with an ENIGMA encoding plasmid or control lacZ plasmid and grown in control media. Osteochondrogenic markers were analyzed using qRT-PCR. Data are shown as means±SEM (n=4), normalized to control. Two tailed unpaired Student's t-test, *P<0.05.

Figure 8E:
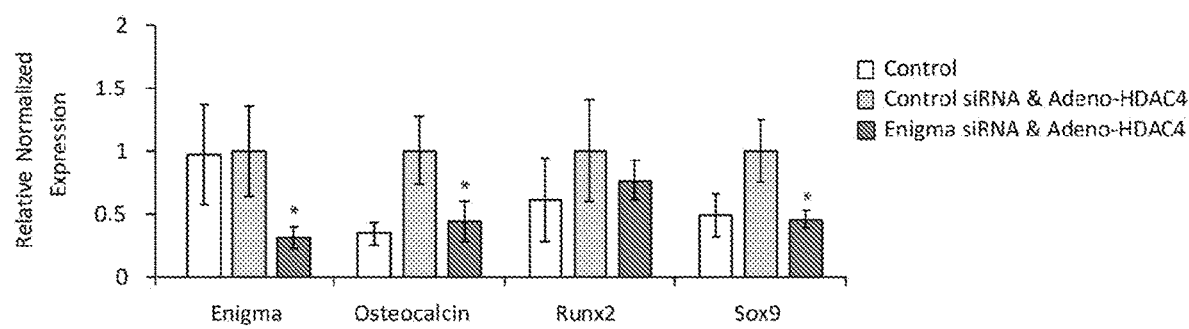

FIG. 8E: VSMCs were transduced with adenoviral vector encoding for flag tagged HDAC4 or control beta-gal virus, and then transfected with ENIGMA or control scrambled siRNA. Osteochondrogenic markers were analyzed using qRT-PCR. Data are shown as means±SEM (n=9), relative to control. Two tailed unpaired Student's t-test, *P<0.05 vs. control siRNA.

Figure 9:
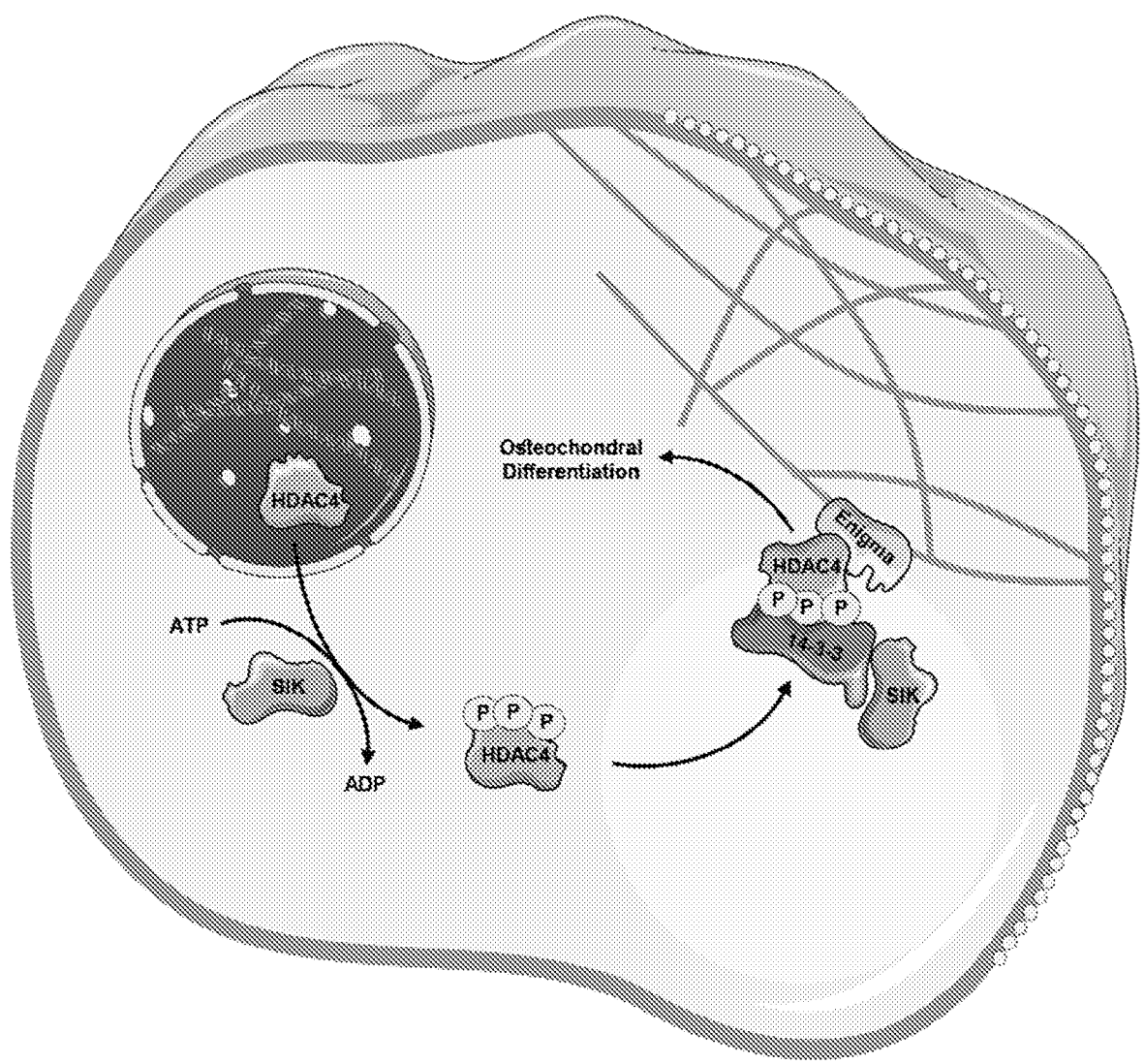

FIG. 9: Model of vascular calcification induction in VSMCs by cytoplasmic HDAC4.

Extracellular stimuli such as high extra-cellular phosphate induce the upregulation of HDAC4 expression. HDAC4 can shuttle between the nucleus and cytoplasm, but phosphorylation by SIK kinase in VSMCs promotes its cytoplasmic accumulation through binding to 14-3-3 proteins. SIK was reported to directly bind 14-3-3 proteins. In the cytoplasm HDAC4 binds the actinin associated protein ENIGMA. All the components of this cytoskeletal complex are required to promote vascular calcification, as knockdown of either HDAC4 or ENIGMA or the inhibition of SIK result in blunted calcification.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Three novel modulators of vascular calcification were unexpectedly identified: cytoplasmic class IIa HDAC4, the cytoplasmic adaptor protein ENIGMA, and the protein kinase SIK.

The experiments provided herein show that HDAC4 is upregulated early in vascular calcification and promotes the process. Vascular calcification shares some similarities with early cartilage and bone formation, and HDAC4 has documented activities in both cartilage and bone development. The global deletion of HDAC4 in mice resulted in premature ossification of developing bones due to early onset chondrocyte hypertrophy with early death. Conversely, overexpression of HDAC4 in proliferating chondrocytes in transgenic mice inhibited chondrocyte hypertrophy. These observations establish the role of HDAC4 as a suppressor of chondrocyte hypertrophy, a late stage in chondrocyte development. In developing bone, an osteoblast specific deletion of HDAC4 resulted in bone loss, suggesting that HDAC4 is a positive regulator of bone formation.

The transcription factor Runx2 is a master gene of skeletogenesis. Reporter assays in cultured cells showed that nuclear HDAC4 can repress the transcriptional activity of Runx2. In fact, the constitutively nuclear mutant HDAC4-3SA was a more potent inhibitor of Runx2 activity than the wild type one. Another study showed that HDAC4 can bind Runx2 and prevent its acetylation. The mechanism of this action is unclear, as HDAC4 has very low deacetylase activity. Despite the ability of HDAC4 to repress Runx2 activity in promoter assays, the role of HDAC4 as suppressor of Runx2 in vivo was called into question. The cartilage phenotype of the HDAC4 knockout mice was initially ascribed to the release of Runx2 from HDAC4 inhibitory activity, but a later study from the same group showed that the effects were mostly mediated through the release from inhibition of Mef2 in chondrocytes. Using an osteoblast specific knockout of HDAC4 it was also shown that HDAC4 does not inhibit Runx2 function in osteoblasts in vivo. Since HDAC4 is almost exclusively cytoplasmic in VSMCs and Runx2 is a nuclear protein, it is not surprising that HDAC4 does not functionally inhibit Runx2 activity in VSMCs.

Runx2 is necessary but not sufficient for the development of vascular calcification. The elimination of Runx2 from smooth muscle cells blunted the development of vascular calcification, but VSMCs specific overexpression of Runx2 in transgenic mice did not induce aortic calcification. Here, high phosphate medium induced a robust calcification in VSMCs with significant upregulation of bone and cartilage marker genes and marked accumulation of matrix calcium. The level of Runx2 however, showed only a non-significant trend for increase in this system (FIG. 1A). In the aortic ring model, induction with HPM did result in a more pronounced increase in Runx2 levels (FIG. 1E). These data suggest that the levels of Runx2 are likely higher at baseline in VSMCs than in aortic rings and show that a significant up-regulation of Runx2 is not required for the development of calcification. Similarly, the overexpression or knockdown of HDAC4 had only modest non-significant effects on the expression level of Runx2 in VSMCs (FIGS. 2A and 2E) and more significant effects in the aortic ring model (FIG. 2C), despite having pronounced effects on the development of calcification in both systems. Together these data imply that other pathways are needed to work in concert with or downstream of Runx2 to promote vascular calcification. The data provided herein suggests that the cytoplasmic HDAC4-ENIGMA containing complex activates such a pathway.

Osteocalcin is upregulated during VSMCs calcification, and the data in here is in agreement with vascular calcification data in patients and rodents that also showed the presence of osteocalcin in calcified plaques. It was shown that Osteocalcin is a major target gene for the cytoplasmic HDAC4-ENIGMA complex. HDAC4 induces the upregulation of Osteocalcin in cultured VSMCs and in aortic rings, and knockdown of HDAC4 suppresses it. This induction depends on the cytoplasmic protein ENIGMA as overexpression of HDAC4 with knockdown of ENIGMA does not result in Osteocalcin upregulation. It was also shown that the nuclear 3SA mutant of HDAC4 does not induce the upregulation of Osteocalcin. Finally, it was shown that disruption of the nuclear mechanosensing LINC complex, prevents HPM induced Osteocalcin upregulation, and that HDAC4 is localized to focal adhesion structures. These findings suggest that the ENIGMA-HDAC4 cytoplasmic complex is involved in a mechanosensing mechanism that can be transmit signals directly to the nucleus to control the expression of genes such as Osteocalcin. In agreement with the results presented herein, Osteocalcin gene expression in bone was decreased nearly 4-fold in mice with osteoblast specific knockout of HDAC4 compared with control mice. This regulation of Osteocalcin expression by class II HDACs appeared to be specific to HDAC4, as mice lacking HDAC5, did not demonstrate a decrease in bone Osteocalcin expression.

Osteocalcin knockout mice develop bones normally, showing that osteocalcin can serve as a marker but is not required for normal bone formation. Surprisingly, it was shown that when overexpressed, osteocalcin functions as a stimulator of VSMCs calcification, upregulating Sox9, Runx2, ALP, proteoglycans, and calcium mineral accumulation. Moreover, in vivo administration of Osteocalcin siRNA, prevented vitamin D induced vascular calcification development. This study shows that in contrast with bone, Osteocalcin is both necessary and sufficient for the induction of vascular calcification, and that the upregulation of Osteocalcin predates, and induces the upregulation of Sox9 and Runx2, rather than result from it. Together these data suggest that Osteocalcin may be the primary target gene of the cytoplasmic HDAC4-ENIGMA complex in VSMCs.

Despite tremendous discoveries about the function, nucleo-cytoplasmic shuttling, structure, and binding partners of class IIa HDACs, several key questions about their mechanism of actions remain unsolved. Depending on the cell type, HDAC4 can be found either in the nucleus or the cytoplasm under basal conditions. In addition to the well documented actions of HDAC4 in the nucleus, indirect evidence suggests that HDAC4 may have additional cytoplasmic functions. For example, the predominant cytoplasmic localization of HDAC4 in neurons, combined with localization to specific cytoplasmic regions such as dendritic spines, suggests a non-nuclear role for HDAC4 in memory formation. The accumulating evidence indicates that HDAC4 function in memory is not through global alteration in histone acetylation, nor through a significant effect on transcription, further suggesting a cytoplasmic role. The inventors conclusively establish a cytoplasmic role for HDAC4. HDAC4 is almost exclusively cytoplasmic in VSMCs at baseline and following osteochondral differentiation. The ability of HDAC4 to promote calcification, despite this exclusive cytoplasmic localization, strongly indicates that HDAC4 functions in the cytoplasm in this context. Importantly, the nuclear 3SA mutant of HDAC4 did not drive calcification. Further, in some embodiments of the invention, inhibition of SIK sends HDAC4 to the nucleus and blocks its ability to promote calcification. In some embodiments, HDAC4 binds a cytoplasmic protein—ENIGMA that is required for its function, further supporting a cytoplasmic function of HDAC4. While a nuclear role for HDAC4 is well established, and is likely the predominant mechanism of action in cardiomyocytes and maturing chondrocytes, it was found that in VSMCs HDAC4 has a cytoplasmic role.

An evolutionary replacement of a class I HDAC catalytic Tyrosine by Histidine in class IIa HDACs catalytic pocket result in almost complete abolition of their catalytic activity. It is hypothesized that class IIa HDACs could function as readers of acetylated proteins, rather than enzymes, acting as molecular scaffolds that recruit additional enzymes and. In some embodiments, the cytoplasmic protein ENIGMA is a binding partner of HDAC4. The PDZ and LIM domains of ENIGMA may act as protein-binding interfaces to facilitate dynamic interactions of signaling molecules. The experiments provided herein show that HDAC4 co-localizes with ENIGMA in the cytoplasm of VSMCs, and that ENIGMA was required for the calcification process. Thousands of proteins are acetylated in different cellular compartments to mediate a wide variety of biological processes. In some embodiments, HDAC4 binds ENIGMA by its N-terminal tail, it may bind or 'read' cytoplasmic acetylated proteins with its C-terminal deacetylase domain to form the ENIGMA pro-calcification protein complex. ENIGMA binds alpha actinin and Palladin with its PDZ domain and in some embodiments the ENIGMA-HDAC4 complex controls a mechanosensing cytoskeletal element that signals the activation of the osteochondrogenic gene program in VSMCs.

SIK1, SIK2, and SIK3 are members of AMPK family. SIK1 was shown to phosphorylate HDAC5 and promote its cytoplasmic accumulation. SIK3 expression was observed in the cytoplasm of prehypertrophic and hypertrophic chondrocytes, and SIK3 knockout mice showed impaired chondrocyte hypertrophy. Mechanistically, SIK3 was shown to bind, phosphorylate and induce the cytoplasmic accumulation of HDAC4. It was shown here that the inhibition of CaMK or PKD did not induce nuclear accumulation of HDAC4 in VSMCs. In contrast, the inhibition of SIK activity resulted in a dose dependent nuclear accumulation of HDAC4, and blunting of the calcification process in cultured VSMCs, in aortic rings, and in vivo. The ability of two other molecules that inhibit SIK or knockdown of an upstream kinase LKB1 to interfere with the process is further evidence for the role of SIK in vascular calcification. The phosphorylation of HDAC4 is required for its binding to proteins such as 14-3-3. This binding likely serves more functions than retaining HDAC4 in the cytoplasm, and is probably required for HDAC4 cytoplasmic activity. SIK was shown to bind 14-3-3 following phosphorylation by LKB1. It was recently shown that parathyroid hormone inhibition of SOST (sclerostin), a WNT antagonist, requires HDAC4 and HDAC5, and is dependent on the inhibition of SIK2 to promote bone growth. In contrast with bone, parathyroid hormone suppresses vascular calcification, and sclerostin is upregulated in the calcification process. The SIKs are expressed in several tissues. The inhibition of SIK was shown to reprogram macrophages to an anti-inflammatory phenotype. HG-9-91-01 was shown to enhanced gluconeogenic gene expression and glucose production in hepatocytes. Once daily treatment with the small molecule SIK inhibitor YKL-05-099 was shown to mimic skeletal effects of PTH and increase bone mass. Therefore, any potential use of SIK inhibitor should include a thorough analysis of off-target effects.

The understanding that vascular calcification is an active process suggests that therapeutic agents may be able to modify its development. However, to date, no such therapies are available. The invention shows three novel modulators—the class IIa HDAC4, the adaptor protein ENIGMA and the protein kinase SIK that together positively regulate this pathological process. The administration of each of these proteins can in some embodiments blunt the calcification process. Importantly, the ability of a small molecule inhibitor of SIK to blunt vascular calcification in vivo suggests that Inhibition of this pathway may be able to target vascular calcification and prevent disease progression, although further studies are needed to assess the efficacy of such an approach.

According to an embodiment of the invention, there is provided a method of treating, reducing or preventing vascular, cardiovascular arterial or valve calcification in a subject in need comprising administering to the subject an effective amount of an agent that prevents or reduces the expression of HDAC4, an agent that modulates the location of HDAC4, an agent that binds to HDAC4 or an inhibitor of HDAC4.

In some embodiments, the vascular, cardiovascular arterial or valve calcification is associated with diabetes, aging, hyperphosphatemia, renal disease, and atherosclerosis.

In some embodiments, the inhibitor of HDAC4 is selected from the group consisting of hydroxamic acid based HDAC inhibitors, Suberoylanilide hydroxamic acid (SAHA), NVP-LAQS24, LBH589, Trichostatin A, Scriptaid, m-Carboxycinnamic acid bishydroxamic acid (CBHA), ABHA, Pyroxamide, Propenamides, Oxamflatin, 6-(3-Chlorophenylureido)caproic bydroxarn ic acid (3-CI-UCHA), A-161906, jnj16241199, tubacin, small interfering RNA (siRNA), short chain fatty acid HDAC inhibitors, butyrate, phenylbutyrate, vaiproate, hydroxamic acid, trichostatins, epoxyketone-containing cyclic tetrapeptides, HC-toxin, Chiamydocin, Diheteropeptide, WF-3161, Cyl-1, Cyl-2, non-epoxyketone-containing cyclic tetrapeptides, Apicidin, cyclic-hydroxamic-acid-containing peptides (CHAPS), benzamides, CI-994, trapoxin, deprudecin, organosulfur compounds, MS275, depsipeptide (FK228), trifluoromethyloxadiazole (TFMO) moiety containing molecules such as TMP 269, TMP 195 and any combination thereof.

In some embodiments of the invention, the agent that modulates the location of HDAC4 is an agent that prevents or reduces the expression of SIK or is an inhibitor of SIK, such as HG-9-91-01, WH-4-023, MRT67307, or YKL-05-099

In some embodiments of the invention, the agent that binds to HDAC4 is an agent that prevents or reduces the expression of ENIGMA (Pdlim7) or is an inhibitor of ENIGMA.

In some embodiments of the invention, the SIK is one or more of SIK isoforms SIK1, SIK2 or SIK 3.

In some embodiments of the invention, the agent that reduces SIK expression is an siRNA.

In some embodiments of the invention, the agent that reduces SIK expression is an agent that blocks upstream activator of SIK or an agent that induces a degradation of SIK or controls posttranslational modification of SIK.

In some embodiments of the invention, the agent that blocks upstream activator of SIK is LKB1 inhibitor.

In some embodiments of the invention, the agent that prevents or reduces the expression of ENIGMA (Pdlim7) is an siRNA of ENIGMA or an agent that induces a degradation of ENIGMA or controls posttranslational modification of ENIGMA.

In some embodiments of the invention, the agent that modulates the location of HDAC4 acts by shuttling the HDAC4 from the cytoplasm.

In some embodiments of the invention, there is provided a method of treating, reducing or preventing vascular, cardiovascular arterial or valve calcification in a subject in need comprising administering to the subject an effective amount of:

an agent that prevents or reduces the expression of HDAC4, an agent that modulates the location of HDAC4, an agent that binds to HDAC4 or an inhibitor of HDAC4 or any combination thereof;

an agent that prevents or reduces the expression of SIK or is an inhibitor of SIK; and/or an agent that prevents or reduces the expression of ENIGMA (Pdlim7) or is an inhibitor of ENIGMA.

In some embodiments of the invention, the agent that prevents or reduces the expression of HDAC4, the agent that modulates the location of HDAC4, the agent that binds to HDAC4 or the inhibitor of HDAC4 or any combination thereof; the agent that prevents or reduces the expression of SIK or is the inhibitor of SIK; and/or the agent that prevents or reduces the expression of ENIGMA (Pdlim7) or is the inhibitor of ENIGMA; are administered consecutively or simultaneously.

In some embodiments of the invention, there is provided a pharmaceutical composition comprising:

an agent that prevents or reduces the expression of HDAC4, an agent that modulates the location of HDAC4, an agent that binds to HDAC4 or an inhibitor of HDAC4 or any combination thereof;

an agent that prevents or reduces the expression of SIK or is an inhibitor of SIK; and/or an agent that prevents or reduces the expression of ENIGMA (Pdlim7) or is an inhibitor of ENIGMA.

In some embodiments of the invention, the pharmaceutical composition comprising an agent that prevents or reduces the expression of HDAC4, an agent that modulates the location of HDAC4, an agent that binds to HDAC4 or an inhibitor of HDAC4 or any combination thereof; an agent that prevents or reduces the expression of SIK or is an inhibitor of SIK; and/or an agent that prevents or reduces the expression of ENIGMA (Pdlim7) or is an inhibitor of ENIGMA; is used for treating, reducing or preventing vascular, cardiovascular arterial or valve calcification in a subject in need.

In some embodiments of the invention, there is provided a pharmaceutical composition comprising an effective amount of an agent that prevents or reduces the expression of HDAC4, an agent that modulates the location of HDAC4, an agent that binds to HDAC4 or an inhibitor of HDAC4, or any combination thereof wherein the pharmaceutical composition is used for treating, reducing or preventing vascular, cardiovascular arterial or valve calcification in a subject in need.

The term "Treat" or "treating" means any treatment, includes, but is not limited to, alleviating symptoms of a disease, disorder, or condition, eliminating the causation of a disease, disorder, or condition on either a temporary or permanent basis wherein this disease, disorder or condition is associated with calcification; or slowing, reducing, or inhibiting an ongoing pathological process of calcification in an asymptomatic individual. In such an asymptomatic individual, the pathological process would likely eventually cause symptoms.

"Preventing" refers to inhibiting the initial onset of a pathologic process of calcification, such that the pathologic process that could eventually lead to development of symptoms never develops (i.e., preventing the development of a disease, disorder, or condition in a prophylactic manner).

"Therapeutically effective amount" means an amount of a compound that is effective in treating or preventing a particular disorder or condition.

"Pharmaceutically acceptable carrier" is a nontoxic solvent, dispersant, excipient, or other material used in formation of a pharmaceutical composition, i.e., a dosage form capable of administration to a subject or patient.

The term "SIK" includes, one or more of its currently known isoforms SIK1, SIK2 and/or SIK3. The inhibitor of the present invention may be specific to one or more isoform of SIK.

The term "inhibitor" includes, but is not limited to, any suitable small molecule, compound, protein or fragment thereof, nucleic acid, formulation or substance that can inhibit SIK/ENIGMA or HDAC4 activity. The inhibitor can exhibit its regulatory effect upstream or downstream of SIK/ENIGMA or HDAC4 or on SIK/ENIGMA or HDAC4 directly. The inhibitor can decrease transcription and/or translation of SIK/ENIGMA or HDAC4, can decrease or inhibit post-translational modification and/or cellular trafficking of SIK/ENIGMA or HDAC4, or can shorten their half life. The inhibitor can also reversibly or irreversibly bind to SIK/ENIGMA or HDAC4, degrade them, inactivate the enzymatic activity of one or more of them, or interfere with the interaction of one or more of them with downstream substrates.

The inhibitor to SIK/ENIGMA or HDAC4 can be, an antisense oligonucleotide to SIK, or an interfering RNA of SIK/ENIGMA or HDAC4. The inhibitor may be selected from the group consisting of antisense oligonucleotide complimentarily binding to mRNA of a SIK/ENIGMA or HDAC4 gene, short interfering RNA, short hairpin RNA, and RNAi, however, the present invention is not limited thereto.

In some embodiments, these are agents that, e.g., alter the interaction of SIK/ENIGMA or HDAC4 with proteins that bind activators, or inhibitors, or receptors, SIK/ENIGMA or HDAC4 inhibitors may include proteins, mimetics, antibodies and fragments thereof, peptides, lipids, carbohydrates, polysaccharides, lipoproteins, glycoproteins, and the like; genetically modified versions of naturally-occurring SIK ligands, e.g., with altered activity, as well as naturally occurring and synthetic ligands, antagonists, small chemical molecules and the like.

In some embodiments, the inhibitor is an antagonist.

"Antagonist" may include any molecule that partially or fully blocks, inhibits, or neutralizes a biological activity of a SIK/ENIGMA or HDAC4. Suitable antagonist molecules may include antibodies or antibody fragments, fragments or amino acid sequence variants of the native polypeptides, peptides, antisense oligonucleotides, small organic molecules, and the like. One of skilled in the art will be able to identify nucleic acid molecules, such as oligonucleotides and siRNA molecules which may inhibit SIK/ENIGMA or HDAC4 gene expression or antibodies (monoclonal and polyclonal antibodies) as well as fragments thereof.

The methods of the present invention employ an inhibitor of HDAC4 activity. An inhibitor of HDAC4 activity is any compound, agent or material that has an inhibitory effect on the activity of HDAC4. An inhibitory effect means that the amount of activity of HDAC4 that is measured in an assay in the absence of an HDAC4 inhibitor is reduced when the inhibitor is added to the assay. Assays to measure HDAC4 activity are known in the art and as described herein. For example, to test HDAC4 activity, one can utilize a luciferase assay, which monitors MEF2-dependent induction of a luciferase reporter gene. Activated MEF2 induces the expression of a luciferase reporter, which can be readily detected in an enzymatic reaction using a luciferase substrate (e.g., luciferin). As an inhibitor of MEF2 activity, elevated levels of HDAC4 activity repress the levels of luciferase produced. In contrast, inhibition of HDAC4 activates MEF2 activity and therefore elevates the luciferase levels produced. This assay therefore provides a convenient method to rapidly and efficiently monitor the activity of HDAC4. An inhibitor of HDAC4 activity of this invention can be but is not limited to hydroxamic acid based HDAC inhibitors, Suberoylanilide hydroxamic acid (SAHA) and its derivatives, NVP-LAQ824, LBH589, Trichostatin A, Scriptaid, m-Carboxycinnamic acid bishydroxamic acid (CBHA), ABHA, Pyroxamide, Propenamides, Oxamflatin, 6-(3-Chlorophenylureido)caproic hydroxamic acid (3-CI-UCHA), A-161906, jnj16241199, tubacin and tubacin analogs, small interfering RNA (siRNA), short chain fatty acid HDAC inhibitors, butyrate, phenylbutyrate, valproate, hydroxamic acid, trichostatins, epoxyketone-containing cyclic tetrapeptides, HC-toxin, Chlamydocin, Diheteropeptide, WF-3161, Cyl-1, Cyl-2, non-epoxyketone-containing cyclic tetrapeptides, Apicidin, cyclic-hydroxamic-acid-containing peptides (CHAPS), benzamides and benzamide analogs, CI-994, trapoxin, deprudecin, organosulfur compounds, MS275, depsipeptide (FK2-28) and any combination thereof. In some embodiments of this invention, one or more than one inhibitor of HDAC4 in any combination can be excluded from the list of inhibitors of HDAC4 of this invention.

An inhibitor of HDAC4 activity that can be employed in the methods of this invention can be an inhibitor that acts at the level of transcription and/or translation of the HDAC4 protein, whereby such an inhibitor alters HDAC4 activity by decreasing the amount of functional HDAC4 protein produced. An inhibitor of HDAC4 activity can be, but is not limited to, an antisense nucleic acid, a ribozyme (e.g., as described in U.S. Pat. No. 5,877,022), RNAs that effect spliceosome-mediated trans-splicing (Puttaraju et al. (1999) Nature Biotech. 17:246; U.S. Pat. No. 6,013,487; U.S. Pat. No. 6,083,702), RNAs that trigger RNA interference mechanisms (RNAi), including small interfering RNAs (siRNA) that mediate gene silencing (Kawaguchi et al., (2003) Cell 115:727-738; Sharp et al. (2000) Science 287:2431) and/or other non-translated RNAs, such as "guide" RNAs (Gorman et al., (1998) Proc. Nat. Acad Sci. USA 95:4929; U.S. Pat. No. 5,869,248 to Yuan et al.), and the like, as are known in the art. These transcription/translation inhibitors can be employed in the methods of this invention individually, in combination with one another and/or in combination with other HDAC4 inhibitors of this invention.

The production and identification of additional siRNA sequences that can be employed in the methods of this invention are well known in the art and thus one of skill in the art would be able to readily produce any number of additional siRNA sequences based on the known nucleotide sequence for HDAC4 and test each such sequence for activity as a silencing RNA of HDAC4, according to standard methods in the art. Thus, the present invention includes any siRNA of HDAC4, the production and characterization of which is known to one skilled in the art.

Another aspect of the present invention relates to a pharmaceutical composition including a pharmaceutically acceptable carrier or excipient and an active siRNA molecule and/or any other inhibitor of SIK, ENIGMA or HDAC4 and/or any other agent (also termed here interchangeably active agent) that modulates the activity of SIK, ENIGMA or HDAC4 according to any of the embodiments of the present invention. The pharmaceutical composition can contain one or more siRNA molecules or inhibitors or active agents of the present invention. Typically, the pharmaceutical composition of the present invention will include an active siRNA molecule or an inhibitor of the of SIK, ENIGMA or HDAC4 of present invention, as well as a pharmaceutically acceptable carrier. The term "active siRNA molecule" or "inhibitor of SIK, ENIGMA or HDAC4" and/or any other "agent that modulates the activity of SIK, ENIGMA or HDAC4" within the pharmaceutical composition is interchangeable with the term "active ingredient". The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of an active ingredient, together with the adjuvants, carriers and/or excipients. While individual needs may vary, determination of optimal ranges of effective amounts of each active ingredient, is within the skill of the art. Typical dosages comprise about 0.01 to about 100 mg/kg body wt. The preferred dosages comprise about 0.1 to about 100 mg/kg body wt. The most preferred dosages comprise about 1 to about 100 mg/kg body wt. Treatment regimen for the administration of the active ingredient thereof of the present invention, can also be determined readily by those with ordinary skill in art. That is, the frequency of administration and size of the dose can be established by routine optimization, preferably while minimizing any side effects.

The solid unit dosage forms can be of the conventional type. The solid form can be a capsule and the like, such as an ordinary gelatin type containing the active ingredient thereof of the present invention, and a carrier, for example, lubricants and inert fillers such as, lactose, sucrose, or cornstarch. In another embodiment, the active ingredient is tabulated with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate. The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, the active ingredient can be incorporated with excipients and used in the form of tablets, capsules, elixirs, suspensions, syrups, and the like. Such compositions and preparations should contain at least 0.1% of active ingredient thereof. The percentage of the compound in these compositions can, of course, be varied and can conveniently be between about 2% to about 60% of the weight of the unit. The amount of active ingredient thereof in such therapeutically useful compositions is such that a suitable dosage will be obtained. Preferred compositions according to the present invention are prepared so that an oral dosage unit contains between about 1 mg and 800 mg of active ingredient thereof.

The active ingredient of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The active ingredient thereof or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

This active ingredient may also be administered parenterally. Solutions or suspensions of these active ingredients thereof can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the active ingredient thereof of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

When administering the active ingredient of the present invention, and pharmaceutical compositions thereof, they can be administered systemically or, alternatively, they can be administered directly to a specific site. Thus, administering can be accomplished in any manner effective for delivering the active ingredients thereof or the pharmaceutical compositions to the specific targeted cells. Exemplary modes of administration include, without limitation, administering the active ingredients thereof or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Determination of a therapeutically effective amount of an active ingredient peptide is well within the capability of those skilled in the art, especially in light of the detailed disclosure provided herein.

Toxicity and therapeutic efficacy of the peptides the siRNA or the inhibitors described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, depend on the subject being treated, the severity of the affliction, the manner of administration, the judgment of the prescribing physician, and all other relevant factors. Determination of the exact dose to be administered is conducted by methods known to a person of skill in the art.

It is further understood that the active ingredient of the invention can be formulated or administered together with additional active ingredients as required to treat the condition of the patient.

EXAMPLES

Materials and Methods

Animal Experiments

ApoE$^{-/-}$ mice were purchased from The Jackson Laboratory. All animals were housed in a temperature-controlled environment with 12 hours light/dark cycles with food and water available ad libitum. Mice were aged 8 weeks when entering the study. Aortic calcification was induced via vitamin D$_3$ overload as previously described [Idelevich A, Rais Y, Monsonego-Ornan E (2011) Bone Gla Protein Increases HIF-1-Dependent Glucose Metabolism and Induces Cartilage and Vascular Calcification. *Arterioscler Thromb Vasc Biol* 31: e55-e71]. 1α,25-Dihydroxyvitamin D$_3$ (Sigma-Aldrich) was dissolved in 100% ethanol and diluted freshly. Mice received IP injections of 1α,25-Dihydroxyvitamin D$_3$ for six consecutive days at a final concentration of 5 µg/Kg in 5% ethanol. SIK inhibition was achieved by daily administration of HG-9-91-01 (ApexBio #B1052) in DMSO at a final concentration of 5 mg/Kg/day. Littermate ApoE−/− mice were arbitrarily divided to receive treatment or control. In the first 4 days HG-9-91-01 was injected IP and on day 5 osmotic pumps (Alzet model 1002) were implanted. Animals were monitored daily and terminated for study at day 18. Specifically, mice were sacrificed in isoflurane and aortas were collected for histology. All mice procedures were performed in accordance with institutional guidelines.

Histochemical Staining

Aortas were either fresh frozen in OCT sliced into section with a cryostat or fixed in 4% formaldehyde, embedded in paraffin and cut into thin sections. Slides were stained to detect calcium depositions with Alizarin red or Von Kossa stains. Alizarin red: slides were incubated in 2% alizarin red (Sigma-Aldrich) for 5 minutes at room temperature, excess stain was washed in DDW. Von Kossa: slides were incubated for 20 minutes in 5% silver nitrate (Sigma-Aldrich), washed twice in DDW, immersed in 0.5% hydroquinone (Sigma-Aldrich) for 2 minutes followed by 2 minutes of 5% sodium thiosulfate (Alfa Aesar).

Cell Culture

Mouse aortic smooth muscle cells were purchased from ATCC (CRL-2797) and grown in DMEM supplemented with 10% FBS. 10 mmol/L beta-glycerophosphate (Sigma-Aldrich) and 0.2 mmol/L 2-Phospho-L-ascorbic acid (Sigma-Aldrich) were added to the growth media for 3-14 days to induce calcification (HPM). All cultured cells were maintained at 37° C. with 5% CO$_2$.

Calcium Quantification Assay

After 14 days of growth cells were washed in PBS and incubated overnight in 0.6N HCl. HCl was collected and calcium content was measured using o-cresolphthalein Calcium colorimetric assay kit (Sigma-Aldrich) according to manufacture instructions. Calcium concentration was then normalized to cells protein concentration.

Aortic Rings Assay

Aortic rings were prepared as described [Nature protocols, Use of the mouse aortic ring assay to study angiogenesis.—PubMed—NCBI, Last updated January 2012, Accessed on January 2012]. In brief, adult C57BL/6 mice were euthanized with isoflurane; thoracic aorta was dissected, cleaned under a microscope and cut into rings. Aortic rings were grown in serum free DMEM media overnight to uniform baseline state, embedded in collagen the next morning and grown for two weeks. Viral transduction was performed in the serum-starvation stage. 10 mmol/L beta-glycerophosphate (Sigma-Aldrich) and 0.2 mmol/L 2-Phospho-L-ascorbic acid (Sigma-Aldrich) were added to the growth media for 14 days to induce calcification (HPM).

Human Aortic Valves

The study was approved by an institutional review committee and subjects gave informed consent. Human aortic valves samples were obtained at Rambam Health Care Campus during aortic valve replacement surgeries. The donors were males and females aged 60-80 years with different degrees of aortic valve calcification. Samples were transported to the laboratory in RNA-later (Thermo-Fisher Scientific); macroscopic healthy parts were used as control.

RNA Extraction RT and qRT-PCR

RNA was extracted from cultured cell using the NucleoSpin RNA kit (MACH EREY-NAGEL). The RNeasy Fibrous Tissue mini and midi kits (Qiagen) were used to extract RNA from aortic rings and human tissue (respectively). All kits were used in accordance with manufacturer protocol. Reverse transcription was done using iScript reagent (Bio-Rad). Quantitative real-time PCR was performed with iTaq universal SYBR green supermix (Bio-Rad) using Bio-Rad CFX96 real time system. Previous study has shown that Actb was among the most stably expressed genes in differentiating osteoblasts [Stephens A. S, et al., Internal control genes for quantitative RT-PCR expression analysis in mouse osteoblasts, osteoclasts and macrophages. BMC Res Notes 2011, 4, 410], and therefore expression data were normalized to the expression of Actb.

For each expression analysis we used at least two different experiments, at least four biological replicates, and two technical replicates for each biological replicates for each gene. We performed a standard curve for each primer pair. All primers and probes were ordered from IDT (see tables 1 and 2):

TABLE 1

| Species | Gene | Forward | Backward |
|---|---|---|---|
| human | HDAC4 | GGC CCA CCG GAA TCT GAA C<br>SEQ ID NO: 1 | GAA CTC TGG TCA AGG GAA CTG<br>SEQ ID NO: 23 |
| mouse | Actb | CTC TGG CTC CTA GCA CCA TGA AGA<br>SEQ ID NO: 2 | GTA AAA CGC AGC TCA GTA ACA GTC CG<br>SEQ ID NO: 24 |
| mouse | Runx2 | CGG CCC TCC CTG AAC TCT<br>SEQ ID NO: 3 | TGC CTG CCT GGG ATC TGT A<br>SEQ ID NO: 25 |
| mouse | Osteocalcin | GCA ATA AGG TAG TGA ACA GAC TCC<br>SEQ ID NO: 4 | GTT TGT AGG CGG TCT TCA AGC<br>SEQ ID NO: 26 |
| mouse | Sox9 | CGA CCC ATG AAC GCC TT<br>SEQ ID NO: 5 | GTC TCT TCT CGC TCT CGT TC<br>SEQ ID NO: 27 |
| mouse | Alkp | GGC TGG AGA TGG ACA AAT TCC<br>SEQ ID NO: 6 | CCG AGT GGT AGT CAC AAT GCC<br>SEQ ID NO: 28 |
| mouse | Spp1 | ATC TCA CCA TTC GGA TGA GTC T<br>SEQ ID NO: 7 | TGT AGG GAC GAT TGG AGT GAA A<br>SEQ ID NO: 29 |
| mouse | Enigma | TGC AAG AAG AAG ATC ACT GGA G<br>SEQ ID NO: 8 | CAT TGA AGT CCT TGC CCC CT<br>SEQ ID NO: 30 |
| mouse | Hdac 1 | AGT CTG TTA CTA CTA CGA CGG G<br>SEQ ID NO: 9 | TGA GCA GCA AAT TGT GAG TCA T<br>SEQ ID NO: 31 |
| mouse | Hdac 2 | GGA GGA GGC TAC ACA ATC CG<br>SEQ ID NO: 10 | TCT GGA GTG TTC TGG TTT GTC A<br>SEQ ID NO: 32 |
| mouse | Hdac 3 | ACC GTG GCG TAT TTC TAC GAC<br>SEQ ID NO: 11 | CAG GCG ATG AGG TTT CAT TGG<br>SEQ ID NO: 33 |
| mouse | Hdac 4 | CAC TGC ATT TCC AGC GAT CC<br>SEQ ID NO: 12 | AAG ACG GGT GGT TTG TAG GA<br>SEQ ID NO: 34 |
| mouse | Hdac 5 | TGC AGC ACG TTT TGC TCC T<br>SEQ ID NO: 13 | GAC AGC TCC CCA GTT TTG GT<br>SEQ ID NO: 35 |
| mouse | Hdac 6 | TCC ACC GGC CAA GAT TCT TC<br>SEQ ID NO: 14 | CAG CAC ACT TCT TTC CAC CAC<br>SEQ ID NO: 36 |
| mouse | Hdac 7 | GAA CTC TTG AGC CCT TGG ACA<br>SEQ ID NO: 15 | GGT GTG CTG CTA CTA CTG GG<br>SEQ ID NO: 37 |
| mouse | Hdac 8 | ACT ATT GC GGA GAT CCA ATG T<br>SEQ ID NO: 16 | CCT CCT AAA ATC AGA GTT GCC AG<br>SEQ ID NO: 38 |
| mouse | Hdac 9 | CAG AAG CAG CAC GAG AAT TTG A<br>SEQ ID NO: 17 | CTC TCT GCG ATG CCT CTC TAC<br>SEQ ID NO: 39 |
| mouse | Sik1 | TCA TGT CGG AGT TCA GTG CG<br>SEQ ID NO: 18 | ACC TGC GTT TTG GTG ACT CG<br>SEQ ID NO: 40 |
| mouse | Sik2 | CTG CTG GCA ACA TGG TGT G<br>SEQ ID NO: 19 | GGG AGA GTT GGT CCA TCA AAA G<br>SEQ ID NO: 41 |
| mouse | Sik3 | GCC ATC CAC ACA TCA TCA GAC<br>SEQ ID NO: 20 | CCA AGT GGT CAA ATA TCT CCC C<br>SEQ ID NO: 42 |
| mouse | Lkb1 | TTG GGC CTT TTC TCC GAG G<br>SEQ ID NO: 21 | CAG GTC CCC CAT CAG GTA CT<br>SEQ ID NO: 43 |
| mouse | Sun2 | ATC CAG ACC TTC TAT TTC CAG GC<br>SEQ ID NO: 22 | CCC GGA AGC GGT AGA TAC AC<br>SEQ ID NO: 44 |

TABLE 2

| Species | Gene | Probe |
|---|---|---|
| Human | ACTB | Hs.PT.39a.22214847 |
| Human | RUNX2 | Hs.PT.58.19252426 |
| Human | SPP1 | Hs.PT.53a.19568141 |
| Human | HDAC4 | Hs.PT.58.19252426 |

Cell Transfection+siRNA

Cell were transfected with pEGFP-HDAC4, pEGFP-HDAC4 3SA, pcDNA HDAC4-flag that were a gift from Tso-Pang Yao (Addgene plasmid #45636, #45637, #30485) [Cohen T. J. et al., The histone deacetylase HDAC4 connects neural activity to muscle transcriptional reprogramming. *J Biol Chem* 2007, 282, 33752-33759] or pEGFP-HDAC4 3-625 plasmid. Mouse ENIGMA (Pdlim7) or truncation mutants were cloned to pcDNA-3HA backbone plasmid. Transfections were performed using polyjet reagent (signaGen) according to manufacturer's instructions. Hdac4 siRNA (IDT), ENIGMA siRNA (GE Healthcare Life Sciences Dharmacon) LKB1 siRNA (IDT) and Sun2 siRNA (IDT) were transfected to the cells using Stemfect RNA Transfection Kit (Stemgent Inc.) according to manufacturer's instructions.

The Ras Recruitment System (RRS)

The RRS screen was performed as described previously [Broder Y. C. et al., The ras recruitment system, a novel approach to the study of protein-protein interactions. *Curr Biol* 1998, 8, 1121-1124]. The bait was a hybrid protein with the mammalian activated Ras protein lacking its farnesylation CAAX box fused to the human HDAC4 N terminus (aa 3-666). The bait plasmid was co-transfected into Cdc25-2 yeast cells with prey plasmids of different myristoylated ENIGMA constructs. The prey plasmids were designed under the control of the Gall-inducible promoter, while the expression of the bait was controlled by a Met-off inducible promoter. Plates were incubated for 7 days at the permissive temperature of 24° C. and were subsequently replica plated onto inductive medium and incubated at the restrictive temperature of 36° C.

Immunoprecipitation and Western Blot

Cultured cells were washed with ice-cold phosphate-buffered saline (PBS) buffer and lysed in buffer containing 50 mM Tris, pH 7.5, 150 mM NaCl, 1 mM EDTA, and 1% NP-40. 400 µg of protein was immunoprecipitated with anti-Flag (Sigma-Aldrich), or IgG antibodies (negative control) and protein A/G agarose beads (Santa Cruz Biotechnology, Inc.) as described previously [Kehat I, et al., Modulation of chromatin position and gene expression by HDAC4 interaction with nucleoporins. *J Cell Biol* 2011, 193, 21-29]. Beads were washed three times with buffer and suspended in 30 µl of Laemmli buffer. Proteins were separated on an SDS gel, blotted, and detected with primary antibody recognizing HA (Santa Cruz Biotechnology, Inc. sc-805) or flag (Sigma-Aldrich).

Western Blot and Protein Fractionation

Cultured cells were washed with ice-cold phosphate-buffered saline (PBS) buffer and lysed in buffer containing 50 mM Tris, pH 7.5, 150 mM NaCl, 1 mM EDTA, and 1% NP-40. Proteins were separated on an SDS gel, blotted, and detected with primary antibodies recognizing HDAC4 (cell signaling 7628s) or Pdlim7 (ProteinTech #10221-1-AP).

For cytoplasmic and nuclear fractionation we used lysis buffer containing 10 mM Hepes, pH 7.9, 10 mM KCl, 1 mM EDTA, 1 mM DTT and 1% NP-40 for the cytoplasmic fraction and lysis buffer containing 20 mM Hepes, pH 7.9, 400 mM NaCl, 1 mM EDTA and 1 mM DTT for the nuclear fraction. Proteins were separated on an SDS gel, blotted, and detected with primary anti-Flag antibody (Sigma-Aldrich).

Chemicals (Inhibitors)

The pan-SIK, inhibitors: HG-9-91-01 (ApexBio #B1052), WH-4-023 (Sigma-Aldrich), MRT67307 (Sigma-Aldrich) and the pan-PKD and CamK inhibitors: CID-2011756 (Cayman #15317), KN-93 (Sigma-Aldrich K1285), were added to the HPM at final concentrations of 0.5, 1, 2, 5 and 10 µmol/L.

Immunofluorescence and Image Analysis

For localization and co-localization assays cell were transfected with pEGFP-HDAC4 plasmids, fixed with 4% formaldehyde in PBS, and blocked in 5% FBS in PBS. Staining for ENIGMA was done with overnight incubation of an antibody recognizing Pdlim7 (ProteinTech #10221-1-AP) in 2% FBS. Cy3-conjugated AffiniPure Donkey Anti-Rabbit IgG secondary antibody (Jackson ImmunoResearch) was used for detection. Nuclei were counterstained with DAPI 1 µg/ml. Cells were imaged using Zeiss Axio observer fluorescent microscope. Cytoplasmic and nuclear localization analysis was performed automatically on acquired images using CellProfiler cell image and analysis software [Carpenter A. E. et al., CellProfiler: image analysis software for identifying and quantifying cell phenotypes. *Genome Biol* 2006, 7, R100].

Adenoviral Vectors

The Gateway system (Invitrogen) was used to generate pEntry clones of for adenoviral vector production. Adenoviral vectors were generated as described previously [Kehat I, et al., 2011].

Statistical Analysis

Data were expressed as mean±SEM or mean±SD where indicated. Sample size was choses base on the size of similar studies in the literature. Comparisons between groups were performed using the student's t test where indicated. The Chi-square proportion test was used to compare percentages where indicated. At least two independent sets of experiments containing at least two biological replicated each were performed.

EXPERIMENTAL RESULTS

Example 1

HDAC4 is Upregulated During Vascular Calcification

Hyperphosphatemia promotes vascular calcification, and mouse aortic VSMCs were shown to reproducibly calcify in the presence of high phosphate culture medium (HPM) [Mackenzie N. C. W. et al., MOVAS-1 cell line: a new in vitro model of vascular calcification. *Int J Mol Med* 2011, 27, 663-668]. Under these conditions cultured VSMCs undergo a profound phenotypic transition with an upregulation of osteochondrogenic markers and calcification of the extracellular matrix, similar to those observed in pathological vascular calcification in vivo [Giachelli C. M. et al., Regulation of vascular calcification: roles of phosphate and osteopontin. *Circ Res* 2005, 96, 717-722]. To assess the involvement of HDACs we treated VSMCs with HPM and assessed calcification. As expected, we observed a significant elevation in osteochondrogenic genes: Alkaline phosphatase (Alkp), Osteocalcin (Bglap), Sox9, and Osteopontin (Sppl) after one week by qRT-PCR (FIG. 1A). We observed only a nonsignificant trend for upregulation of the transcription factor Runx2 by 1.27 fold. Matrix mineralization was evident by a significant increased matrix calcium by o-cresolphthalein colorimetric assay (FIG. 1B). We examined the expression of different HDACs upon induction of VSMCs calcification, and observed unchanged expression of HDACs 1, 2 and 7, a small but significant upregulation of the class I HDAC3 (1.16 fold), an upregulation of the class I HDAC8, the class IIb HDAC6, and a 2-fold up-regulation of the class IIa HDAC4 levels (FIG. 1C). The expression of the class IIa HDAC5 and HDAC9 was also significantly upregulated upon induction, but their absolute level was low (FIGS. 1H and 1I). We also analyzed HDAC4 protein level, and noted a similar significant 2-fold increase in its level (FIG. 1D). To further validate the culture findings we developed an ex-vivo aortic calcification model based on the mouse aortic ring angiogenesis assays [Nature protocols, Use of the mouse aortic ring assay to study angiogenesis.—PubMed—NCBI, Last updated January 2012, Accessed on January 2012]. In this model, adult mice aortas are dissected, cleaned, and cut into rings, embedded in collagen, and grown for two weeks in osteo-inductive high phosphate or control culture media. This aortic ring assay may be more physiologically relevant since the arterial wall remains intact and the different adult cells in the arterial wall and their anatomical relations are preserved. The high phosphate medium stimulated the rings to activate osteogenic pathways and elevate the expression of osteochondrogenic genes like Runx2 and Osteopontin (Sppl) (FIG. 1E). Osteopontin is not found in normal arteries, but is upregulated at sites of calcification in human atherosclerotic plaques and in calcified aortic valves [Giachelli C M, Speer M Y, Li X, Rajachar R M, Yang H (2005) Regulation of vascular calcification: roles of phosphate and osteopontin. Circ Res 96: 717-722]. Importantly, the expression of HDAC4 was also significantly up-regulated in this model by 1.6 fold (FIG. 1E). Matrix mineralization in the rings was evident by Von Kossa stain (FIG. 1F). Next, human aortic valves were collected during valve replacement surgery. Expression analysis using qRT-PCR revealed significant up-regulation of the valve calcification markers RUNX2 and Osteopontin (SPP1) as well as in HDAC4 by 7.16 fold in severely calcified valves, compared to controls (FIG. 1G).

Example 2

HDAC4 is a Positive Regulator of Vascular Calcification

The two models and the in vivo data from patients showed that HDAC4 was significantly up-regulated in vascular and valve calcification. To assess the significance of this upregulation we over-expressed HDAC4, without adding high phosphate media. The over-expression of human HDAC4 in cultured VSMCs resulted in the up-regulation of osteochondrogenic marker genes and a significant increase in matrix calcium by o-cresolphthalein colorimetric assay (FIGS. 2A and 2B and FIG. 2G). Similarly, the overexpression of HDAC4 in aortic rings without the addition of high phosphate media resulted in upregulation of osteochondrogenic marker genes and a significant increase in matrix calcium (FIG. 2H and FIGS. 2C and 2D). These data show that the upregulation of HDAC4 is sufficient to induce the expression of osteochondrogenic genes and drive matrix calcification. Overexpression of HDAC4 in HPM treated aortic rings did not result in additional markers upregulation (FIG. 2I). Conversely, the knockdown of HDAC4 using two different siRNAs by 75% and 74%, resulted in downregulation of the calcification marker Osteocalcin (0.21 and 0.3 fold respectively) (FIG. 2J and FIG. 2E). Importantly, the knockdown of HDAC4 significantly blunted the accumulation of matrix calcification induce by HPM (FIG. 2F). Interestingly Runx2 showed only a trend for reduction with knockdown of HDAC4 (FIG. 2E). Together, these data identify HDAC4 as a positive regulator of the vascular calcification process.

Example 3

Cytoplasmic localization of HDAC4 in VSMCs

Class IIa HDACs are Considered Nuclear Proteins that are Exported Out of the Nucleus in response to stimulus dependent kinase activation [Parra M. and Verdin E. Regulatory signal transduction pathways for class IIa histone deacetylases. Curr Opin Pharmacol 2010, 10, 454-460]. However, in certain cell types, in the absence of external signals, the class IIa HDAC4 can be found in both the nucleus and the cytoplasm [Parra M. Class IIa HDACs—new insights into their functions in physiology and pathology. FEBS J 2015, 282, 1736-1744]. To track the location of HDAC4 in VSMCs we used green fluorescent protein (GFP) tagged constructs of HDAC4 (FIG. 3E). Wild type HDAC4 was almost exclusively cytoplasmic in VSMCs and remained almost exclusively cytoplasmic even under treatment with HPM (FIG. 3A). The nuclear export signal (NES) in the C-terminal tail of HDAC4 allows its nuclear export, and the phosphorylation of three Serine residues in the N-terminal tail is known to mediate cytoplasmic retention through binding to 14-3-3 proteins. To further explore the nucleo-cytoplasmic shuttling of HDAC4 we used three different constructs: a truncated N-terminal construct containing only the first 625 amino acids of HDAC4 that includes the nuclear localization signal (NLS) but not the NES (HDAC4 3-625), a mutant in which the three Serine residues ($Ser^{246}$, $Ser^{467}$, and $Ser^{632}$) in the N-terminal tail were mutated to Alanine (3SA), or the wild type HDAC4. We performed a detailed quantitative analysis of localization in VSMCs and control HeLa epithelial cells using these constructs (FIG. 3B and FIG. 3F). To avoid any bias, the analysis was performed automatically using CellProfiler analysis software [Carpenter A E, Jones T R, Lamprecht M R, Clarke C, Kang I H, Friman O, Guertin D A, Chang J H, Lindquist R A, Moffat J, et al. (2006) CellProfiler: image analysis software for identifying and quantifying cell phenotypes. Genome Biol 7: R100]. This quantitative analysis showed that the wild type HDAC4 was indeed almost exclusively cytoplasmic in VSMCs (92.3% of cells exclusively cytoplasmic and 7.7% of cells both nuclear and cytoplasmic distribution), but not in control HeLa epithelial cells in which wild-type HDAC4 was exclusively cytoplasmic only in 23.7% of cells (FIG. 3B and FIG. 3F), indicating that shuttling of the GFP tagged constructs is intact and that the localization of HDAC4 in VSMCs is inherently different from epithelial cells. Both the truncated N-terminal 3-625 mutant and the 3SA mutants were predominantly nuclear in both VSMCs and Hela cells (FIG. 3B and FIG. 3F). These data suggest that nucleo-cytoplasmic shuttling and cytoplasmic retention of HDAC4 is intact in VSMCs and requires the NES and the phosphorylation of the N-terminal Serine residues respectively. The ability of HDAC4 to modify the calcification process despite its exclusive cytoplasmic localization, both before and after osteochondral differentiation, strongly suggest that HDAC4 functions in the cytoplasm to promote VSMCs calcification. To further test this point, we examined the ability of the nuclear 3SA mutant of HDAC4 to drive calcification. In contrast with the wild type HDAC4 which is exclusively cytoplasmic in 92.3% of the cells, the 3SA mutant is predominantly nuclear and can be found in an exclusive cytoplasmic location only in 17% of the VSMCs (FIG. 3B). We further confirmed the cytoplasmic localization of wild-type HDAC4 and the nuclear localization of 3SA HDAC4 using biochemical fractionation (FIG. 3G). When overexpressed in VSMCs, the wild type cytoplasmic HDAC4 drove the upregulation of osteochondrogenic genes and matrix calcification, while the over-expression of the 3SA nuclear mutant failed to induce calcification (FIGS. 3C and 3D). Taken together this data show that cytoplasmic but not nuclear HDAC4 drives the calcification process.

Example 4

SIK Activity Controls the Cytoplasmic Localization of HDAC4

The nuclear localization of the 3SA HDAC4 mutant in VSMCs shows that the cytoplasmic retention of wild type HDAC4 depends on the phosphorylation of the three Serine residues in the N-terminal tail of HDAC4. Several protein kinases, such as CamK, PKD, and SIK were reported to phosphorylate the N-terminal tail of HDAC4. We used chemical blockers of these kinases to investigate their possible role in the cytoplasmic retention of HDAC4 in VSMCs. We used the cell preamble pan-PKD inhibitor CID 2011756 that was reported to block PKD1, PKD2 and PKD3 [Sharlow E. R. et al., Discovery of diverse small molecule chemotypes with cell-based PKD1 inhibitory activity. *PLoS One* 2011, 6, e25134], and the CamK inhibitor KN-93 that inhibits CamK I, II and IV [Pellicena P. and Schulman H. CaMKII inhibitors: from research tools to therapeutic agents. *Front Pharmacol* 2014, 5, 21]. Both inhibitors did not significantly affect the location of HDAC4, which remained completely cytoplasmic even at doses as high as 10 μmol/L: 96.8%, 99.6%, 91.6% cytoplasmic localization of HDAC4 with vehicle, PKD inhibitor or CamK inhibitor respectively (FIGS. 4A and 4B). In contrast, the specific pan-SIK inhibitor HG-9-91-01 that can inhibit SIK1, SIK2, and SIK3 [Clark K. et al., 2012] induced nuclear import of HDAC4 in a dose dependent manner: 96.8%, 97.4%, 75.7% and 14.4% cytoplasmic localization of HDAC4 with vehicle, 0.5 μmol/L, 2 μmol/L, or 10 μmol/L of HG-9-91-01 respectively (FIGS. 4A and 4B). We also tested two other SIK inhibitors—WH-4-023 and MRT67307. Both of these agents induced the shuttling of HDAC4 to the nucleus (FIG. 4C). The similar activity of three independent small molecule inhibitors of SIK on HDAC4 localization strongly indicates that the effects on HDAC4 result specifically from the inhibition of SIK.

Example 5

SIK Activity Promotes Vascular Calcification

The data herein show that HDAC4 functions in the cytoplasm to promote the calcification of VSMCs. Therefore, the blockade of SIK kinase that phosphorylates HDAC4 to promote its association with cytoplasmic proteins and controls its cytoplasmic localization is expected to inhibit HDAC4 activity and blunt the calcification process. We therefore induced calcification in both cultured VSMCs and in the aortic ring model with HPM in the presence of the pan-SIK inhibitor HG-9-91-01 or vehicle. The inhibition of SIK blunted the upregulation of the osteochondrogenic genes and matrix calcification in VSMCs (FIGS. 5A and 5B), as well as in aortic rings (FIGS. 5C and 5D). SIK has three isoforms (SIK1, SIK2, and SIK3), and all three are expressed in VSMCs (FIG. 4D). This redundancy prevented us from knocking down SIK efficiently. LKB1 is a master kinase that directly phosphorylates the activation loop of SIK as well as other 5'-AMP-activated protein kinase (AMPK) related kinases [Patel K, Foretz M, Marion A, Campbell DG, Gourlay R, Boudaba N, Tournier E, Titchenell P, Peggie M, Deak M, et al. (2014) The LKB1-salt-inducible kinase pathway functions as a key gluconeogenic suppressor in the liver. *Nat Commun* 5: 4535]. Knockdown of LKB1 with siRNA blunted the upregulation of the osteochondrogenic genes (FIG. 4E), further showing the importance of the SIK pathway in vascular calcification.

Next, we tested the importance of SIK activity for vascular calcification in vivo. ApoE−/− mice were treated with high dose vitamin $D_3$ for 6 days as previously described [Idelevich A. et al., 2011]. We concomitantly treated the animals with the pan-SIK inhibitor HG-9-91-01 or vehicle for 3 weeks. Von Kossa staining of whole mount aortic slices (FIG. 6A) and Von Kossa and alizarin red staining of fixed and paraffin embedded thin aortic sections (FIGS. 6B and 6C) showed that vitamin $D_3$ treatment resulted in aortic medial calcification in the mice within 3 weeks, but concomitant treatment with a pan-SIK inhibitor markedly blunted the development of these calcifications.

Example 6

ENIGMA Binds HDAC4 in the Cytoplasm and Promotes Vascular Calcification

The cytoplasmic function of HDAC4 likely occurs in the context of a protein complex. To identify its members we searched for HDAC4 binding partners using the Ras Recruitment System (RRS) modified yeast-two-hybrid system [Broder YC, Katz S, Aronheim A (1998) The ras recruitment system, a novel approach to the study of protein-protein interactions. *Curr Biol* 8: 1121-1124]. In the RRS system the interaction between the bait and prey proteins allows the Cdc25-2 temperature sensitive yeast strain to grow at 36° C. Using the N-terminal tail of HDAC4 (amino acids 3-666) as bait we identified 3 independent clones of ANKRA2, a known binding partner of HDAC4 [Kinsey T. A. et al., Class II histone deacetylases confer signal responsiveness to the ankyrin-repeat proteins ANKRA2 and RFXANK. *Mol Biol Cell* 2006, 17, 438-447], and 3 independent clones of the protein ENIGMA (Pdlim7). ENIGMA is a cytoplasmic protein that localizes to actin-rich structures in vascular smooth muscle, heart, and platelets. Structurally, ENIGMA is composed of an N-terminal PDZ domain, a linker, and three LIM domains. We initially validated the screen results in yeast with the RRS system using the N-terminal HDAC4 fragment as bait and different fragments of ENIGMA or the homologous protein CYPHER (Ldb3) as prey (FIG. 7A). This analysis showed that constructs containing the three LIM domains of ENIGMA, with or without the linker domain, interacted with the N-terminal domain of HDAC4, and conferred yeast growth, while constructs containing the PDZ domain and linker, linker and first LIM domain, or the PDZ and LIM domains of the protein CYPHER did not (FIG. 7A). We also validated the results using co-immunoprecipitation in cultured cells with 3HA tagged ENIGMA fragments or with 3HA tagged ENIGMA family protein Enigma Homologue (ENH, Pdlim5) and CYPHER (Ldb3), and flag tagged full length HDAC4. In agreement with the yeast experiments, both the full length ENIGMA protein and a fragment containing only the three LIM domains interacted with full length flag-tagged HDAC4 (FIG. 7B), while the 3HA tagged ENIGMA fragments containing either the PDZ domain and linker or the linker and first LIM domain did not interact. The 3HA-tagged Enigma Homologue (ENH, Pdlim5) and CYPHER (Ldb3) showed very little binding (FIG. 7B). For more detailed mapping of the interacting domains in ENIGMA we co-immunoprecipitated constructs containing one, two or three of the LIM domains and various combination of two LIM domains of ENIGMA (1+2, 2+3, or 1+3) with the full length flag tagged HDAC4 (FIG. 7C). This analysis showed that two LIM domains of ENIGMA were required for the interaction with HDAC4, but any two of the three sufficed. We continued with a more detailed mapping of the interacting domains of HDAC4. We co-immunoprecipitated 3HA tagged full length ENIGMA, and assessed the interaction with 6×His tagged HDAC4 fragments. Initial mapping showed that both the whole N-terminal fragment of HDAC4 (aa 3-628), and a smaller fragment containing amino acids 3-222 of HDAC4 were able to bind ENIGMA (FIG. 7D). A finer mapping experiment again showed that an N-terminal fragment of amino acids 3-222 of HDAC4 was able to bind ENIGMA, but a fragment of amino acids 3-185 of HDAC4, or smaller fragments, showed very little binding (FIG. 7E). This mapping indicates that the N-terminal amino acids 185-222 of HDAC4 interact with two of the three LIM domain of ENIGMA. This domain of HDAC4 does not include any of the three phosphorylated Serine residues, and indicates that the phosphorylation of HDAC4 is not required for the interaction with ENIGMA.

To assess the location of ENIGMA and its relationship with HDAC4 immunofluorescence staining in VSMCs was used. The actin binding ENIGMA showed cytoplasmic staining, and the distribution of ENIGMA co-localized with that of HDAC4 (FIG. 8A). Since ENIGMA is an actin interacting cytoplasmic protein that binds HDAC4, we checked if the cytoplasmic retention of HDAC4 in VSMCs was dependent on ENIGMA. To this end, ENIGMA expression was knocked down using siRNAs and assessed the location of HDAC4. Despite achieving a high degree of ENIGMA knockdown (FIG. 5E), the location of HDAC4 was unchanged and remained cytoplasmic (FIG. 8B). We also show that over-expression of ENIGMA cannot force the cytoplasmic localization of 3SA HDAC4 (FIG. 5F). These observations are not surprising since the phosphorylation of HDAC4 is required for its cytoplasmic localization, and the mapping provided herein suggested that phosphorylation of HDAC4 was not required for its binding to ENIGMA.

ENIGMA was reported to promote bone formation [Liu H, et al., Osteoinductive LIM mineralization protein-1 suppresses activation of NF-kappaB and selectively regulates MAPK pathways in pre-osteoclasts. Bone 2010, 46, 1328-1335], and ENIGMA knockout mice displayed reduced trabecular bone density [Gary M. F., et al., Lim mineralization protein-1 knockout mice have reduced spine trabecular bone density on microcomputed tomography due to decreased bone morphogenetic protein responsiveness. Neurosurgery 2014, 61 Suppl 1, 182-186]. Therefore the role of ENIGMA was tested in VSMCs calcification. Indeed, knockdown of ENIGMA significantly impeded the osteochondral differentiation of VSMCs (FIG. 8C). Together these data indicate that proteins other than ENIGMA are required to retain HDAC4 in the cytoplasm, but that ENIGMA is required as part of the cytoplasmic complex that promotes calcification in VSMCs. To assess if HDAC4 and ENIGMA not only act in parallel but that they indeed depend on each other, ENIGMA was initially over-expressed and the effects on osteochondral genes were assessed. The overexpression of ENIGMA did not result in upregulation of osteochondral markers, and in fact resulted in a very modest, yet significant downregulation of Osteocalcin expression (FIG. 8D). This downregulation likely resulted from perturbation of the cytoskeleton-ENIGMA-HDAC4 cytoplasmic complex stoichiometry by ENIGMA overexpression. The requirement of ENIGMA together with the inability of ENIGMA overexpression to promote osteochondral differentiation on its own shows that ENIGMA depends on other proteins for this function. Next HDAC4 was overexpressed together with control or ENIGMA siRNA. While HDAC4 overexpression was sufficient to induce osteochondral differentiation, the concomitant knockdown of ENIGMA significantly blunted this ability (FIG. 8E). These data show that HDAC4 and ENIGMA depend on each other to drive vascular calcification.

To further understand the ENIGMA-HDAC4 cytoplasmic complex, and to understand how this cytoplasmic complex drives vascular calcification, a second RRS screen was performed with ENIGMA PDZ domain. This screen (FIGS. 6D, 6E and 6F) identified the cytoskeletal proteins alpha-actinin and palladin as ENIGMA PDZ-domain binding partners. The α-actinins are a family of spectrin-like actin-binding proteins with critical roles in cytoskeleton maintenance. Stiff substrates led to increased expression of focal adhesion components, including α-actinin [Engler A. J. et al., Matrix Elasticity Directs Stem Cell Lineage Specification. Cell 2006, 126, 677-689], and α-Actinin-3 deficiency is associated with reduced bone mass in human and mice [Yang N, et al., α-Actinin-3 deficiency is associated with reduced bone mass in human and mouse. Bone 2011, 49, 790-798]. Palladin is an actin filament binding protein that directly crosslinks actin filaments [Gurung R, et al., Actin polymerization is stimulated by actin cross-linking protein palladin. Biochem J 2016, 473, 383-396]. Mutations in palladin that interrupt actin binding result in disruption of the actin cytoskeleton [Beck M. R., et al., Structure and Function of Palladin's Actin Binding Domain. J Mol Biol 2013, 425, 3325-3337]. Palladin was shown to be upregulated in response to both cyclic tensile strain and osteogenic differentiation [Wall M. E., et al., Human adipose-derived adult stem cells upregulate palladin during osteogenesis and in response to cyclic tensile strain. Am J Physiol Cell Physiol 2007, 293, C1532-8]. These data show that Enigma binds cytoskeletal proteins with its PDZ domain, and HDAC4 with its 3-LIM domain, and suggest that this complex in involved in the cytoskeleton response to mechanical stress.

Multiple lines of evidence show that VSMCs respond to mechanical signals [Sage A. P., et al., Regulatory mechanisms in vascular calcification. Nat Rev Cardiol 2010, 7, 528-536], and it was shown that differentiation of cells to osteoblasts in response to biochemical cues can be modulated by matrix stiffness [Engler A. J. et al., 2006, Yip C. Y. Y., et al., Calcification by valve interstitial cells is regulated by the stiffness of the extracellular matrix. Arterioscler Thromb Vasc Biol 2009, 29, 936-942]. Data also suggests that mechanical stress can be channeled along cytoskeletal filaments and act directly on the nucleus to regulate gene expression (reviewed in [Wang N. et al., Mechanotransduction at a distance: mechanically coupling the extracellular matrix with the nucleus. Nat Rev Mol Cell Biol 2009, 10, 75-82]). The nucleus is physically connected to the cytoskeleton through the linker of nucleoskeleton and cytoskeleton (LINC) complex [Wang N. et al., 2009], that is composed of SUN and KASH family members. KASH proteins interact with cytoskeletal elements through their C-terminal extremity, whereas SUN proteins are connected to nuclear lamins. The LINC complex was shown to transfer mechanical stresses from the cytoskeleton to the genome and control gene expression [Alam S. G. et al., The mammalian LINC complex regulates genome transcriptional responses to substrate rigidity. Sci Rep 2016, 6, 38063]. To investigate the role of direct transmission of stress from the cytoskeleton to the nucleus, the members of the LINC complex were examined. Sun2, a member of the LINC complex, is an integral membrane protein of the inner nuclear membrane connecting the nuclear envelope to the cytoskeleton [Turgay Y. et al., A classical NLS and the SUN domain contribute to the targeting of SUN2 to the inner nuclear membrane. *EMBO J* 2010, 29, 2262-2275]. The knockdown of Sun2 using siRNA resulted in blunting of HPM induced upregulation of Osteocalcin (FIG. 6G), showing that the integrity of the LINC complex is required for osteogenic differentiation of VSMCs, and that Osteocalcin gene expression is controlled by the nuclear mechanosensing apparatus. It was proposed that during vascular calcification HDAC4 is upregulated and accumulates in the cytoplasm in response to phosphorylation by SIK. Cytoplasmic HDAC4 is recruited to the cytoskeleton (FIG. 6H) to associate with the protein Enigma. It was speculated that the ENIGMA-HDAC4 is part of the cytoskeletal mechanosensing apparatus. Enigma mediated recruitment of HDAC4 to the cytoskeleton, may modifies the response of the cytoskeleton to the extra-cellular matrix stiffness, and this modified stress is transmitted directly to the nucleus via the LINC complex to change gene expression.

In summary, it was shown that the expression of HDAC4 is upregulated during vascular calcification in cultured VSMCs, in aortic rings, and in patient calcifying valves. Using both loss- and gain of function approaches it was shown that HDAC4 promotes this calcification process. HDAC4 functions to promote calcification in the cytoplasm. It is almost exclusively cytoplasmic in VSMCs, and a nuclear mutant of HDAC4 does not promote calcification. The cytoplasmic location of HDAC4 and its role in calcification depends on the activity of the protein kinase SIK. The inhibition of SIK shuttles HDAC4 to the nucleus and impedes the calcification process. Mechanistically we showed that in the cytoplasm HDAC4 binds the cytoskeleton associated protein ENIGMA, which is required for vascular calcification (FIG. 9).

What is claimed is:

1. A method of treating, reducing or preventing vascular calcification, cardiovascular calcification, arterial calcification, or valve calcification in a subject in need comprising administering to the subject an effective amount of an agent that promotes nuclear accumulation of HDAC4, wherein the agent that promotes the nuclear accumulation of HDAC4 is a pan-SIK inhibitor.

2. The method of claim 1, wherein the vascular calcification, cardiovascular calcification, arterial calcification, or valve calcification is associated with diabetes, aging, renal disease, hyperphosphatemia, atherosclerosis.

3. The method of claim 1, wherein said SIK is SIK isoform SIK1, SIK2, SIK 3, or a combination thereof.

4. The method of claim 1, wherein the inhibitor of SIK is an agent that controls post-translational modification of SIK.

5. The method of claim 1, wherein the inhibitor of SIK blocks an upstream activator of SIK, wherein said upstream activator is an LKB1 inhibitor.

* * * * *

SEQUENCE LISTING

```
<160> NUMBER OF SEQ ID NOS: 44

<210> SEQ ID NO 1
<211> LENGTH: 19
<212> TYPE: DNA
<213> ORGANISM: Artificial Sequence
<220> FEATURE:
<223> OTHER INFORMATION: HDAC4

<400> SEQUENCE: 1
ggcccaccgg aatctgaac                                            19

<210> SEQ ID NO 2
<211> LENGTH: 24
<212> TYPE: DNA
<213> ORGANISM: Artificial Sequence
<220> FEATURE:
<223> OTHER INFORMATION: Actb

<400> SEQUENCE: 2
ctctggctcc tagcaccatg aaga                                      24

<210> SEQ ID NO 3
<211> LENGTH: 18
<212> TYPE: DNA
<213> ORGANISM: Artificial Sequence
<220> FEATURE:
<223> OTHER INFORMATION: Runx2

<400> SEQUENCE: 3
cggccctccc tgaactct                                             18

<210> SEQ ID NO 4
<211> LENGTH: 24
<212> TYPE: DNA
<213> ORGANISM: Artificial Sequence
<220> FEATURE:
<223> OTHER INFORMATION: Osteocalcin

<400> SEQUENCE: 4
gcaataaggt agtgaacaga ctcc                                      24
```

```
<210> SEQ ID NO 5
<211> LENGTH: 17
<212> TYPE: DNA
<213> ORGANISM: Artificial Sequence
<220> FEATURE:
<223> OTHER INFORMATION: Sox9

<400> SEQUENCE: 5
cgacccatga acgcctt                                                    17

<210> SEQ ID NO 6
<211> LENGTH: 21
<212> TYPE: DNA
<213> ORGANISM: Artificial Sequence
<220> FEATURE:
<223> OTHER INFORMATION: Alkp

<400> SEQUENCE: 6
ggctggagat ggacaaattc c                                               21

<210> SEQ ID NO 7
<211> LENGTH: 22
<212> TYPE: DNA
<213> ORGANISM: Artificial Sequence
<220> FEATURE:
<223> OTHER INFORMATION: Spp1

<400> SEQUENCE: 7
atctcaccat tcggatgagt ct                                              22

<210> SEQ ID NO 8
<211> LENGTH: 22
<212> TYPE: DNA
<213> ORGANISM: Artificial Sequence
<220> FEATURE:
<223> OTHER INFORMATION: Enigma

<400> SEQUENCE: 8
tgcaagaaga agatcactgg ag                                              22

<210> SEQ ID NO 9
<211> LENGTH: 22
<212> TYPE: DNA
<213> ORGANISM: Artificial Sequence
<220> FEATURE:
<223> OTHER INFORMATION: Hdac 1

<400> SEQUENCE: 9
agtctgttac tactacgacg gg                                              22

<210> SEQ ID NO 10
<211> LENGTH: 20
<212> TYPE: DNA
<213> ORGANISM: Artificial Sequence
<220> FEATURE:
<223> OTHER INFORMATION: Hdac 2

<400> SEQUENCE: 10
ggaggaggct acacaatccg                                                 20

<210> SEQ ID NO 11
<211> LENGTH: 21
<212> TYPE: DNA
<213> ORGANISM: Artificial Sequence
<220> FEATURE:
<223> OTHER INFORMATION: Hdac 3
```

```
<400> SEQUENCE: 11
accgtggcgt atttctacga c                                              21

<210> SEQ ID NO 12
<211> LENGTH: 20
<212> TYPE: DNA
<213> ORGANISM: Artificial Sequence
<220> FEATURE:
<223> OTHER INFORMATION: Hdac 4

<400> SEQUENCE: 12
cactgcattt ccagcgatcc                                                20

<210> SEQ ID NO 13
<211> LENGTH: 19
<212> TYPE: DNA
<213> ORGANISM: Artificial Sequence
<220> FEATURE:
<223> OTHER INFORMATION: Hdac 5

<400> SEQUENCE: 13
tgcagcacgt tttgctcct                                                 19

<210> SEQ ID NO 14
<211> LENGTH: 20
<212> TYPE: DNA
<213> ORGANISM: Artificial Sequence
<220> FEATURE:
<223> OTHER INFORMATION: Hdac 6

<400> SEQUENCE: 14
tccaccggcc aagattcttc                                                20

<210> SEQ ID NO 15
<211> LENGTH: 21
<212> TYPE: DNA
<213> ORGANISM: Artificial Sequence
<220> FEATURE:
<223> OTHER INFORMATION: Hdac 7

<400> SEQUENCE: 15
gaactcttga gcccttggac a                                              21

<210> SEQ ID NO 16
<211> LENGTH: 21
<212> TYPE: DNA
<213> ORGANISM: Artificial Sequence
<220> FEATURE:
<223> OTHER INFORMATION: Hdac 8

<400> SEQUENCE: 16
actattgcgg agatccaatg t                                              21

<210> SEQ ID NO 17
<211> LENGTH: 22
<212> TYPE: DNA
<213> ORGANISM: Artificial Sequence
<220> FEATURE:
<223> OTHER INFORMATION: Hdac 9

<400> SEQUENCE: 17
cagaagcagc acgagaattt ga                                             22
```

<210> SEQ ID NO 18
<211> LENGTH: 20
<212> TYPE: DNA
<213> ORGANISM: Artificial Sequence
<220> FEATURE:
<223> OTHER INFORMATION: Sik1

<400> SEQUENCE: 18
tcatgtcgga gttcagtgcg                    20

<210> SEQ ID NO 19
<211> LENGTH: 19
<212> TYPE: DNA
<213> ORGANISM: Artificial Sequence
<220> FEATURE:
<223> OTHER INFORMATION: Sik2

<400> SEQUENCE: 19
ctgctggcaa catggtgtg                     19

<210> SEQ ID NO 20
<211> LENGTH: 21
<212> TYPE: DNA
<213> ORGANISM: Artificial Sequence
<220> FEATURE:
<223> OTHER INFORMATION: Sik3

<400> SEQUENCE: 20
gccatccaca catcatcaga c                  21

<210> SEQ ID NO 21
<211> LENGTH: 19
<212> TYPE: DNA
<213> ORGANISM: Artificial Sequence
<220> FEATURE:
<223> OTHER INFORMATION: Lkb1

<400> SEQUENCE: 21
ttgggccttt tctccgagg                     19

<210> SEQ ID NO 22
<211> LENGTH: 23
<212> TYPE: DNA
<213> ORGANISM: Artificial Sequence
<220> FEATURE:
<223> OTHER INFORMATION: Sun2

<400> SEQUENCE: 22
atccagacct tctatttcca ggc                23

<210> SEQ ID NO 23
<211> LENGTH: 21
<212> TYPE: DNA
<213> ORGANISM: Artificial Sequence
<220> FEATURE:
<223> OTHER INFORMATION: HDAC4

<400> SEQUENCE: 23
gaactctggt caagggaact g                  21

<210> SEQ ID NO 24
<211> LENGTH: 26
<212> TYPE: DNA
<213> ORGANISM: Artificial Sequence
<220> FEATURE:
<223> OTHER INFORMATION: Actb

<400> SEQUENCE: 24
gtaaaacgca gctcagtaac agtccg 26

<210> SEQ ID NO 25
<211> LENGTH: 19
<212> TYPE: DNA
<213> ORGANISM: Artificial Sequence
<220> FEATURE:
<223> OTHER INFORMATION: Runx2

<400> SEQUENCE: 25
tgcctgcctg ggatctgta 19

<210> SEQ ID NO 26
<211> LENGTH: 21
<212> TYPE: DNA
<213> ORGANISM: Artificial Sequence
<220> FEATURE:
<223> OTHER INFORMATION: Osteocalcin

<400> SEQUENCE: 26
gtttgtaggc ggtcttcaag c 21

<210> SEQ ID NO 27
<211> LENGTH: 20
<212> TYPE: DNA
<213> ORGANISM: Artificial Sequence
<220> FEATURE:
<223> OTHER INFORMATION: Sox9

<400> SEQUENCE: 27
gtctcttctc gctctcgttc 20

<210> SEQ ID NO 28
<211> LENGTH: 21
<212> TYPE: DNA
<213> ORGANISM: Artificial Sequence
<220> FEATURE:
<223> OTHER INFORMATION: Alkp

<400> SEQUENCE: 28
ccgagtggta gtcacaatgc c 21

<210> SEQ ID NO 29
<211> LENGTH: 22
<212> TYPE: DNA
<213> ORGANISM: Artificial Sequence
<220> FEATURE:
<223> OTHER INFORMATION: Spp1

<400> SEQUENCE: 29
tgtagggacg attggagtga aa 22

<210> SEQ ID NO 30
<211> LENGTH: 20
<212> TYPE: DNA
<213> ORGANISM: Artificial Sequence
<220> FEATURE:
<223> OTHER INFORMATION: Enigma

<400> SEQUENCE: 30
cattgaagtc cttgcccct 20

<210> SEQ ID NO 31
<211> LENGTH: 22
<212> TYPE: DNA
<213> ORGANISM: Artificial Sequence
<220> FEATURE:
<223> OTHER INFORMATION: Hdac 1

<400> SEQUENCE: 31
tgagcagcaa attgtgagtc at                                              22

<210> SEQ ID NO 32
<211> LENGTH: 22
<212> TYPE: DNA
<213> ORGANISM: Artificial Sequence
<220> FEATURE:
<223> OTHER INFORMATION: Hdac 2

<400> SEQUENCE: 32
tctggagtgt tctggtttgt ca                                              22

<210> SEQ ID NO 33
<211> LENGTH: 21
<212> TYPE: DNA
<213> ORGANISM: Artificial Sequence
<220> FEATURE:
<223> OTHER INFORMATION: Hdac 3

<400> SEQUENCE: 33
caggcgatga ggtttcattg g                                               21

<210> SEQ ID NO 34
<211> LENGTH: 20
<212> TYPE: DNA
<213> ORGANISM: Artificial Sequence
<220> FEATURE:
<223> OTHER INFORMATION: Hdac 4

<400> SEQUENCE: 34
aagacggggt ggttgtagga                                                 20

<210> SEQ ID NO 35
<211> LENGTH: 20
<212> TYPE: DNA
<213> ORGANISM: Artificial Sequence
<220> FEATURE:
<223> OTHER INFORMATION: Hdac 5

<400> SEQUENCE: 35
gacagctccc cagttttggt                                                 20

<210> SEQ ID NO 36
<211> LENGTH: 21
<212> TYPE: DNA
<213> ORGANISM: Artificial Sequence
<220> FEATURE:
<223> OTHER INFORMATION: Hdac 6

<400> SEQUENCE: 36
cagcacactt ctttccacca c                                               21

<210> SEQ ID NO 37
<211> LENGTH: 20
<212> TYPE: DNA
<213> ORGANISM: Artificial Sequence
<220> FEATURE:
<223> OTHER INFORMATION: Hdac 7

<400> SEQUENCE: 37
ggtgtgctgc tactactggg                                          20

<210> SEQ ID NO 38
<211> LENGTH: 23
<212> TYPE: DNA
<213> ORGANISM: Artificial Sequence
<220> FEATURE:
<223> OTHER INFORMATION: Hdac 8

<400> SEQUENCE: 38
cctcctaaaa tcagagttgc cag                                      23

<210> SEQ ID NO 39
<211> LENGTH: 21
<212> TYPE: DNA
<213> ORGANISM: Artificial Sequence
<220> FEATURE:
<223> OTHER INFORMATION: Hdac 9

<400> SEQUENCE: 39
ctctctgcga tgcctctcta c                                        21

<210> SEQ ID NO 40
<211> LENGTH: 20
<212> TYPE: DNA
<213> ORGANISM: Artificial Sequence
<220> FEATURE:
<223> OTHER INFORMATION: Sik1

<400> SEQUENCE: 40
acctgcgttt tggtgactcg                                          20

<210> SEQ ID NO 41
<211> LENGTH: 22
<212> TYPE: DNA
<213> ORGANISM: Artificial Sequence
<220> FEATURE:
<223> OTHER INFORMATION: Sik2

<400> SEQUENCE: 41
gggagagttg gtccatcaaa ag                                       22

<210> SEQ ID NO 42
<211> LENGTH: 22
<212> TYPE: DNA
<213> ORGANISM: Artificial Sequence
<220> FEATURE:
<223> OTHER INFORMATION: Sik3

<400> SEQUENCE: 42
ccaagtggtc aaatatctcc cc                                       22

<210> SEQ ID NO 43
<211> LENGTH: 20
<212> TYPE: DNA
<213> ORGANISM: Artificial Sequence
<220> FEATURE:
<223> OTHER INFORMATION: Lkb1

<400> SEQUENCE: 43
caggtccccc atcaggtact                                          20

```
<210> SEQ ID NO 44
<211> LENGTH: 20
<212> TYPE: DNA
<213> ORGANISM: Artificial Sequence
<220> FEATURE:
<223> OTHER INFORMATION: Sun2

<400> SEQUENCE: 44
cccggaagcg gtagatacac                                              20
```